United States Patent
Ince et al.

(10) Patent No.: US 11,754,824 B2
(45) Date of Patent: Sep. 12, 2023

(54) METHOD AND APPARATUS FOR DIAGNOSTIC ANALYSIS OF THE FUNCTION AND MORPHOLOGY OF MICROCIRCULATION ALTERATIONS

(71) Applicant: Active Medical BV, Leiden (NL)

(72) Inventors: Can Ince, Leiden (NL); Matthias Peter Hilty, Illnau (CH); Yasin Ince, Leiden (NL); Yavuz Ahiska, Esher (GB)

(73) Assignee: Active Medical, BV, Leiden (NL)

( * ) Notice: Subject to any disclaimer, the term of this patent is extended or adjusted under 35 U.S.C. 154(b) by 0 days.

(21) Appl. No.: 16/830,450

(22) Filed: Mar. 26, 2020

(65) Prior Publication Data

US 2020/0310098 A1 Oct. 1, 2020

Related U.S. Application Data

(60) Provisional application No. 62/824,076, filed on Mar. 26, 2019.

(51) Int. Cl.
*G02B 21/36* (2006.01)
*G16H 50/20* (2018.01)
(Continued)

(52) U.S. Cl.
CPC ......... *G02B 21/36* (2013.01); *G02B 21/0012* (2013.01); *G06N 3/063* (2013.01);
(Continued)

(58) Field of Classification Search
CPC .... G02B 21/36; G02B 21/0012; G16H 50/20; G06N 3/063; G06N 3/08
See application file for complete search history.

(56) References Cited

U.S. PATENT DOCUMENTS 7,872,235 B2 * 1/2011 Rousso .................. A61B 6/037
250/363.04
2008/0058593 A1 * 3/2008 Gu ............................ G06T 5/40
600/109

(Continued)

FOREIGN PATENT DOCUMENTS

WO 2014/114814 A1 7/2014

OTHER PUBLICATIONS

Second consensus on the assessment of sublingual microcirculation in critically ill patients: results from a task force of the European Society of Intensive Care Medicine, Ence et al., Feb. 6, 2018, pubmed.ncbi.nlm.nih.gov/29411044/, retrieved on Oct. 18, 2021 (Year: 2018).*
McIlroy Stuart et al: "In vivo classification of inflammation in blood vessels with convolutional neural networks", 2017 International Joint Conference on Neural Networks (IJCNN), IEEE, May 14, 2017 (May 14, 2017), pp. 3022-3027, XP033112421, DOI: 10.1109/IJCNN.2017.7966231 [retrieved on Jun. 30, 2017] * p. 3022-p. 3023*.

(Continued)

*Primary Examiner* — Jonathan R Messmore
(74) *Attorney, Agent, or Firm* — Optimus Patents US, LLC

(57) ABSTRACT

An intelligent vital microscopy, IVM, device is described. The IVM device includes: a receiver configured to receive at least one IVM image of a human microcirculation, MC, of an organ surface; a learning processor coupled to the receiver and configured to: process the at least one IVM image and extract at least one MC variable therefrom, and identify from the extracted at least one MC variable of the at least one IVM image at least one of: an underlying cause for an observed abnormality, an intervention, a disease state, a disease diagnosis, a medical state of the human; a presence of a pathogen; and an output coupled to the learning processor and configured to output the identification.

21 Claims, 14 Drawing Sheets

(51) Int. Cl.
*G02B 21/00* (2006.01)
*G06N 3/063* (2023.01)
*G06N 3/08* (2023.01)
*G06T 7/00* (2017.01)

(52) U.S. Cl.
CPC .............. *G06N 3/08* (2013.01); *G06T 7/0012* (2013.01); *G16H 50/20* (2018.01); *G06T 2207/10016* (2013.01); *G06T 2207/10056* (2013.01)

(56) References Cited

U.S. PATENT DOCUMENTS

| | | | | |
|---|---|---|---|---|
| 2012/0053919 | A1* | 3/2012 | Taylor | A61B 5/02 703/9 |
| 2014/0018649 | A1* | 1/2014 | Jespersen | A61B 6/032 600/322 |
| 2015/0161330 | A1* | 6/2015 | Joao | G16H 15/00 705/3 |
| 2019/0005195 | A1* | 1/2019 | Peterson | G16H 50/30 |
| 2019/0073769 | A1* | 3/2019 | Watanabe | A61B 5/1459 |
| 2019/0131016 | A1* | 5/2019 | Cohen | G16H 70/60 |
| 2019/0139221 | A1* | 5/2019 | Castro-Gonzalez | A61B 5/0261 |
| 2020/0176114 | A1* | 6/2020 | Badawi | A61B 5/7275 |

OTHER PUBLICATIONS

Ocak Isik et al: "Monitoring microcirculation", Bailliere's Best Practice and Research, Clinical Anesthesiology, Bailliere Tindall, London, US, vo 1 • 30, No. 4, Nov. 3, 2016 (Nov. 3, 2016), pp. 407-418, XP029841306,ISSN: 1521-6896, DOI:10.1016/J.BPA. 2016.10.008* p. 409 *.

Favaron et al.; "Capillary Leukocytes, Microaggregates, and the Response to Hypoxemia in the Microcirculation of Coronavirus Disease 2019 Patients"; Critical Care Medicine Journal; www.ccmjournal.org; pp. 1-10; 2021.

Hutchings et al; "Microcirculatory, Endothelial, and Inflammatory Responses in Critically Ill Patients with COVID-19 are Distinct from Those Seen in Septic Shock: A Case Control Study"; Shock; vol. 55, No. 6, pp. 752-758, 2021.

Ince Can et al: "Second consensus on the assessment of sublingual microcirculation in critically ill patients: results from a task force of the European Society of Intensive Care Medicine", Intensive Care Medicine, Springer Berlin Heidelberg, Berlin/Heidelberg, vol. 44, No. 3, Feb. 6, 2018 (Feb. 6, 2018), pp. 281-299, XP036462528, ISSN: 0342-4642, DOI: 10.1007/S00134-018-5070-7 [retrieved on Feb. 6, 2018].

EPO Article 94 Communication; EPO Application No. 20 165 861.1-1210; dated Oct. 6, 2021.

* cited by examiner

METHOD AND APPARATUS FOR DIAGNOSTIC ANALYSIS OF THE FUNCTION AND MORPHOLOGY OF MICROCIRCULATION ALTERATIONS

FIELD OF THE INVENTION

The field of this invention relates to a method and apparatus for processing at least one or sequence of vital microscopy image(s) and performing a diagnostic analysis of a function and morphology of microcirculation alterations of humans related to health and disease, for example for identifying a disease of a subject and an associated therapeutic resolution

BACKGROUND OF THE INVENTION

Several types of clinical technologies have been described in the literature that purports to monitor the human microcirculation (MC). These have included laser Doppler imaging, laser speckle imaging, near-infrared spectroscopy, contrast enhanced ultrasound, spectrophotometry and oxygen electrodes. However, these clinical technologies, without exception, do not directly image but rather measure surrogates of microcirculatory flow and/or oxygenation. Most importantly none of these clinical technologies can image the capillaries of the microcirculation (main physiological compartment of the MC) where oxygen is transported to the tissues. Instead, these clinical techniques provide indexes or metrics expressed in arbitrary units, which is sub-optimal. This is a severe limitation of monitoring the microcirculation, since with these clinical techniques it is neither possible to measure quantitatively parameters, nor do they provide quantitative information regarding the function of the capillaries.

The inventors of the present invention have recognised and appreciated that this issue is key in adequately and correctly quantifying MC function, as the inability of these clinical techniques to image the capillaries makes it impossible to obtain quantitative parameters of the MC.

In recent years, it is known that observation of the microcirculation has been made possible under clinical conditions at the bedside using hand-held vital microscopes (HVM). HVMs consist of a pen-like light guide with a magnification lens at its end and which, with suitable illumination and image acquisition, is able to image the microcirculation within it to capture the flowing blood cells. HVM has provided much detailed information about the microcirculatory and cellular basis for diseases and therapy in patients. Since HVM provides microscopic images of the microcirculation, including all the various vessels combined with flowing cells, it allows quantitative measures to be made of the function of the microcirculation, and thus makes it a unique technology in the range of technologies present whose aim is to measure the microcirculation.

Measurements using HVM provide complex images of the (micro)vasculature with red and white blood cells moving therein. Measurements are performed on organ surfaces (e.g. during operations) but are most routinely used for measurement of the microcirculation sublingually. Functional parameters related to the function of the microcirculation have been shown to provide sensitive information regarding the cause and therapeutic resolution of a host of disease states in advance of conventional physiological parameters being measured.

FIG. 1 illustrates three known handheld microscope devices, each of which includes as its basic components a video or image capture sensor, a focus mechanism, a magnifying lens and an illumination source, such that surface reflections of the organ surfaces are avoided. The devices can be powered by either a battery or a mains supply. Images of the microcirculation (with therein moving blood cells) are saved either on computer memories or on video recorders, and are then analysed off-line using specialized software.

A first known handheld microscope device is an orthogonal polarization spectroscopy (OPS) imaging device 100. Orthogonal polarized spectral imaging OPS imaging (5) works by eliminating directly reflected green (550±70 nm) polarized light from tissue surface via an orthogonally placed analyzer allowing structures below the surface to be visualized. The known OPS imaging device 100 includes a light source 105 that is coupled to a polarizer 110 such that it transmits a polarized incident light into a beam splitter 115, Reflected (polarized) light 120 is input to a scatterer 125 that scatters the image of the target tissue and transmits the scattered (de-polarized) light to a charge coupled device (CCD) 135. The CCD is an integrated circuit etched onto a silicon surface forming light sensitive elements called pixels. Photons incident on this surface generate charge that can be read by an electronics device/element. The CCD 135 outputs a digital copy of the light patterns falling on the device to a video recorder/monitor 140 and off-line image analysis 145 may be subsequently performed.

A second known handheld microscope device is a sidestream dark field (SDF) imaging device 150. SDF imaging works by emitting green (540±150 nm) light from light-emitting diodes (LEDs) arranged in a ring formation optically isolated from the central core of the light guide directly illuminating the tissue microcirculation. A SDF imaging device comprises a stroboscopic LED 155 ring-based imaging modality, which was introduced for clinical observation of the microcirculation 160. The microcirculation 160 can be viewed through a magnifying lens 165 and still or moving images of the MC can be taken by camera 170. The camera 170 is able to output a digital copy of the microcirculation 160 image adjacent the SDF imaging device 150 to a video recorder/monitor 140 and off-line image analysis 145 may be subsequently performed.

A third known handheld microscope device is an incident dark field (IDF) imaging device 150. The illumination of IDF imaging, in contrast to SDF, is not optically isolated from the centre core and illuminates the entire field of view in a non-homogeneous fashion, according to darkfield microscopy. IDF imaging is a technique that, similar to OPS and SDF imaging, allows real-time visualisation of the microcirculation 160. Based upon the illumination of microvessels covered by a thin epithelial layer, it may be thought of as the successor to both orthogonal polarization spectroscopy (OPS), and more recently, sidestream dark field (SDF) imaging. An IDF imaging device comprises a light emitting diode (LED) 155 that also allows real-time clinical observation of the microcirculation 160. The microcirculation 160 can be viewed through a magnifying lens 165 and video images can be taken by image sensor 180, The image sensor 180 is able to output a digital copy of the microcirculation 160 image to a video recorder/monitor 140 and off-line image analysis 145 may be subsequently performed.

Each of the three types of known HVM device 100, 150, 175 is optically configured using three different types of optical configuration in order to eliminate surface reflections of incident light to allow observation of the microcirculation below the surface of the organ. Green light is used because it is absorbed by haemoglobin present in the red blood cells allowing visualization of these cells as they flow in the microcirculation. Vessels not containing red blood cells cannot be observed in this way and remain invisible to this type of HVM (as under rest conditions about 30% of microvessels are not filled with red blood cells). They can, however, be filled red blood cells by opening the microvessels by topical application of a vasodilator such as nitroglycerine.

It is known that segmentation of (micro) vascular structures can be performed on images taken by, for example, the HVMs of FIG. 1. Sublingually, these segmented vascular structures can be drawn manually to identify the various anatomic structures. Several types of hardware and software proposals have been put forward to identify the microcirculation and kinetics of the moving blood cells therein (see references [1]-[4]).

A known hardware implementation in this general field includes WO0122741 (A2), titled: 'Medical applications of orthogonal polarization spectral imaging'. WO2001022741A2 describes a use of an OPS imaging device in order to capture images of the microcirculation of organ surfaces, in order to derive information of states of disease. The device is configured to only capture the microcirculation image and does so using OPS imaging. However, the inventors of the present invention have recognised and appreciated that this has limited value in practical scenarios. A further known hardware implementation in this general field includes US2014369588 (A1), titled: Darkfield imaging system and methods for automated screening of cells. A further known hardware implementation in this general field includes EP1673007B/US2012089031: titled 'System and method for imaging the reflectance of a substrate'. In EP1673007B, the microcirculation is identified as an asset to, in addition to the macrocirculation, and in order to gain such pertinent clinical information regarding the state of the cardiovascular system, EP1673007B proposes to monitor the microcirculation, using a side-stream dark field microscopy device (see reference [5]). However, the suggested device only yields image sequences, and the inventors of the present invention have recognised and appreciated that this has limited value in practical scenarios where identification of MC abnormalities coupled to a specific disease state, advice on the optimal type therapy and the prognosis of the state of disease is required.

Known software implementations in this general field include: US2012269420 (A1), titled: 'Image processing and machine learning for diagnostic analysis of microcirculation'; GB2510176 (A), titled: 'Determining patient prognosis by microcirculation analysis'. US2012269420 describes a MC study approach that specifically mentions a calculation of only three parameters PPV, FCD and PVD. On the basis of this classification the authors of US2012269420 decide whether someone has a haemorrhage or is normal. The authors of US2012269420 focus their methodology on a decision as to whether (or not) to resuscitate a patient. The inventors of the present application have recognised and appreciated that calculation of these three parameters (FCD, PPV, FCD) provide very limited sensitivity and specificity to identify states of disease.

GB2510176A proposes to use changes in FCD, pericapillary bleeding and capillary flow in order to determine a prognosis of patients (see reference [6]). GB2510176A specifies technical details on the image capture (camera) setup and mentions that flow analysis and counting of the capillaries may be carried out manually.

The document titled: 'A software tool to quantify capillary blood volume and absolute red blood cell velocity in sublingual incident dark field microscopy video clips', authored by Hilty M P, Arend S, Van Assen M, Toraman F, Ince C., and published in the Intensive Care Medical Exposition 2018; No. 6: pp 172-173, describes an approach to allow an analysis and quantification of many variables of segmented vascular structures and blood flow to be measured instantaneously in an automatic manner (see reference [7]).

However, the inventors have recognised and appreciated that more relevant and more detailed information needs to be extracted from an MC in order to gain a deeper understanding of health, disease and therapy of these segmented microvascular structures. Furthermore, the inventors have recognised and appreciated that a speed of accessing, and accurate processing of, MC image data is needed in order to better advise clinicians of a health, disease and/or therapy of a patient.

SUMMARY OF THE INVENTION

Accordingly, the invention seeks to mitigate, alleviate or eliminate one or more of the above mentioned disadvantages, either singly or in any combination. Aspects of the invention provide an intelligent vital microscopy, IVM, device (which in some examples encompasses other microscopic configurations to image the microcirculation in humans for example including non-held microscopic devices, which can be placed or fixated on an organ surface for continuous monitoring and imaging of the microcirculation) and a method therefor, as described in the appended claims.

According to a first aspect of the invention, there is described an intelligent vital microscopy, IVM, device that includes: a receiver configured to receive at least one IVM image of a human microcirculation, MC, of an organ surface; and a learning processor coupled to the receiver and configured to: process the at least one IVM image and extract at least one MC variable therefrom, and identify from the extracted at least one MC variable of the at least one IVM image at least one of: an underlying cause for an observed abnormality, an intervention, a disease state, a disease diagnosis, a medical state of the human; a presence of a pathogen. An output is coupled to the learning processor and configured to output the identification.

In this manner, a significant problem with known handheld vital microscopy (HVM) devices is alleviated, in that the images being generated no longer need to be analysed off-line and are analysed real-time using a learning processor. Furthermore, the learning processor configured as above may facilitate obtaining clinical information from the diagnostic analysis, for example regarding an origin of the microcirculatory abnormalities, a presence of a pathogen, identification of the underlying disease or a type and amount of therapy that is deemed to be most effective in correcting, say, a pathogenic state.

According to an optional example, the identified extracted at least one MC variable may include at least one of: a quantification of a morphological parameter of the MC, at least one functional parameter of the MC. According to an optional example, the identified at least one functional parameter of the MC may include at least one of: functional capillary density, FCD, tissue red blood cell perfusion, tRBCp; total vessel density, TVD; MC hemodynamic values; capillary; a venule; arteriolar blood flow; blood volume; an identification of at least one type of vessel; a proportion of perfused vessel density, PVD; a proportion of FCD of flowing red blood cells. RBC, that carry oxygen; a vessel diameter, VD; a RBC and leucocyte velocity; a proportion of perfused vessels, PPV, a microvascular flow index of a flow heterogeneity, MFIhet; rolling and sticking leukocytes, microscopy or fluorescence spectroscopy for identification of numbers of platelets and leucocytes; microcirculatory RBC Hb saturation; a capillary tube and discharge haematocrit. According to an optional example, at least one functional parameter may be either: measured in steady state or for identification of a maximum present number of capillaries by application of a challenge, where the challenge is one of: metabolic, vasodilator, blood transfusion, exercise, focus quality, depth of focus, image movement and content of microcirculatory structures.

According to an optional example, such a MC variable may also include at least a portion or an entirety of the properties and structure of a trained neuronal network, incorporated in the IVM device trained for performing a specific task such as provide; output as feedback to a user as one or more of: (i) a quality of the at least one IVM image sequence of a human sublingual microcirculation, (ii) a classification of identified MC abnormality, (iii) an origin of a cause of the identified MC abnormality, (iv) a recommended therapeutic strategy to normalize the MC abnormalities and resolve a disease state.

In this manner, the claimed IVM device is able to enhance MC images and recognise patterns. In doing so the claimed IVM device may be able to identify and quantify abnormal red and white blood cell flow kinetics, and/or provide distribution of blood cell velocities. In addition, the claimed IVM device may be able to calculate capillary hematocrit, discharge hematocrit and tissue red blood cell perfusion. The latter may be used in some examples as a resuscitation end point. Monitoring of the MC parameters from the extraction may also be performed, say on a routine basis by nurses who use the IVM device, so that they can detect abnormalities that can be used to trigger a further examination of the patient or clinical examination. Similarly, use can be made in a personal-care environment as part of home care for patients having cardiovascular disease.

According to an optional example, the identified extracted at least one MC variable may include at least one of: a quantification of a morphological parameter of the MC, at least one functional parameter of the MC, and the identified at least one morphological parameter comprises at least one of: functional microcirculatory structure, a total vessel density, TVD; a tortuosity; one or more fractal dimension; bifurcations of MC vessels. According to an optional example, the functional microcirculatory structure may include at least one of: sputum glands, orifices, vessel loops, rectal crypts, cell to cell junctions, one or more cell dimensions, a functional state of mitochondria, properties of nuclei, microcirculatory units related to organ function, intestinal villi, renal tubular structures, liver lobule, alveoli, glycocalyx dimensions.

In this manner, an identified, extracted at least one MC variable enables a quantification of a morphological parameter of the MC, to analyse, say, morphological features of the vasculature (fractal dimensions, tortoisity) and to unexpected blood flow properties as well as the presence of abnormal microcirculatory structures. In addition, identified, extracted at least one MC variable may address a combination of various abnormalities, which may signify impending disease or an abnormal response to therapy. Analysis of such complex relationships would be very difficult in a supervised fashion, which is why unsupervised analysis using the claimed learning processor of such images as proposed herein provides a solution to alleviate this need, thereby providing superior diagnostic capacity of the IVM device.

According to an optional example, the identified disease may include a presence of sepsis and the learning processor may be configured to distinguish between inflammation and infection from early sepsis or septic shock based on the nature of a microcirculatory alteration. Currently it is very difficult to identify impending sepsis. Analysis of the microcirculation according to the claimed invention may provide a sensitive and specific methodology for showing the presence of sepsis. Since it is imperative that such a diagnostic tool be used for screening patients, and that there are possibly more sensitive microcirculatory alterations present in the microcirculation present than the current methodology can detect, the use of the claimed IVM device may provide a much more sensitive methodology to detect in a point-of-care setting the presence of sepsis and in extension to immediately start therapy and evaluate whether there is a suitable response.

According to an optional example, the learning processor may be configured to process the at least one IVM image sequence and identify a type of shock that a patient is suffering from, and identify at least one of: a resuscitation strategy based on a type of fluid or blood, a futility of resuscitation, an area of the MC that requires resuscitating: a target for titration of intravenous fluids and blood. Currently it is very difficult, and requires a high degree of skill, to be able to distinguish between the five categories of shock. This is important to be able to do since each type of shock requires a different type of therapy, and being able to correctly identify a lack of response of the patient is key for the clinician to be able to establish whether a suitable resuscitation end point has been reached. Current analysis of HVM images does not achieve this, whereas this is a clinical need since resuscitation is an on-going process requiring immediate feedback and diagnosis. This information currently lacking in existing technology may in some examples be achieved using the claimed IVM device. In some examples, the claimed IVM device may classify and distinguish between at least the following types of shock: cardiogenic, obstructive, distributive (septic shock), hypovolemic (haemhorragic) shock, anaemic shock (too few red blood cells caused by too much fluid administration or disease acquired such as in cancer). In some examples, the IVM device may include in this analysis other clinical variables, such as blood pressure, cardiac output, blood gasses, lactate and biomarkers of organ injury, etc. Having identified the type of shock the claimed IVM device may identify an optimal resuscitation strategy to given (e.g. cardiopulmonary resuscitation, vasopressor agents, fluid administration, blood transfusion, extracorporeal assist device). Thus, in this manner, the claimed IVM device may be able to identify that resuscitation from shock has been successful in correcting MC alterations induced by shock.

According to an optional example, the MC variable may also include a portion of an entirety of the properties and the structure of a trained neuronal network (e.g., supervised or unsupervised learning), incorporated in the IVM device and trained for performing a specific task.

According to an optional example, the learning processor may evaluate a severity of a patient's wounds based on the MC analysis and, in response thereto: identify a wound healing of scar formation; and output a recommended fluid resuscitation or drug strategy that reduces edema formation, promotes wound healing and reduces scar formation. In this manner, the claimed IVM device is able to analyse and identify a growth of the microcirculation, which is essential for normal wound healing since it transports oxygen to the growing tissue during wound repair. Furthermore, outputting this to, say, a clinician, may provide a real-time (patho) physiological state of the wound, as well as the patient's response to therapy. Wound healing is dependent upon the development of scar formation, such as occurs the healing of surgical wounds including sternites. Wounds can be infected or be present in deeper tissue structure. Diabetic ulcer wounds are indicative of such. The use of tissue regenerative therapies or wound dressings can enhance wound healing. Wounds as a result of burns can benefit from fluid resuscitation. Advantageously, such wounds and wound healing can be verified by the IVM device.

According to an optional example, the learning processor may, based on the MC analysis, identify heart failure of a patient, which carries with it a risk for myocardial infarction (MI). Currently, as well as being a risk for MI, there is no known mechanism for evaluating a success of therapy for the clinician or even in a home-care environment. Employing the IVM device herein described enables an observation sublingually on the MC image to identify if the heart is functioning well enough to achieve adequate microcirculatory perfusion. Abnormalities in blood flow kinetics might indicate myocardial instability. In addition analysis of microcirculatory patterns may also provide sensitive information regarding the functioning of the failing heart being supported either by extracorporeal assist device or using medication. Identifying the success of such therapy is very difficult, which is greatly eased by using the IVM device described herein, as it can provide a tool for evaluating heart function at the level of the microcirculation and identify a success (or failure) of therapeutic support of the failing heart.

According to an optional example, the learning processor may, based on the MC analysis, identify a presence of infectious disease and a potential burden of infectious agents, which can otherwise only be shown by blood withdrawal and analysis. There exists a real need for bloodless diagnostics especially when presented with potential harmful pathogens, such as viral and bacterial agents. In addition an inexpensive methodology, allowing easy measurement in large populations, is needed. This is especially needed in a setting of tropical disease, such as malaria and denge. The claimed IVM device has been shown to be sensitive in identifying microcirculatory alterations in malaria and denge. Furthermore, the inventors of the present invention have recognised and appreciated a need for a point-of-care methodology, for identifying infected people the infection itself and possibly then identify the infectious agent without having to withdraw blood.

There is a need in surgery for a surgical diagnostic hand tool that would allow precise examination needed for making surgical decisions (e.g. to resect or not). According to an optional example, the IVM device herein described may identify abnormal microvascular structures on tumour surfaces as well ischemic boundaries associated with surgical reconstructions, which may lead to anastomotic leakage with great precision. Thus, the IVM device can be used to identify boundaries of pathology and healthy tissue or the nature of pathology of tissues, such as a tumour (or absence thereof) or ischemia (or absence thereof). Thus, the IVM device may allow direct diagnosis and identification of abnormal tissue and provide the surgeon important information in support of clinical decision making during surgery.

There is a need to identify diabetes, which is presently predominantly performed by analysis of blood samples requiring blood withdrawal. One of the main targets of diabetes, however, are the blood vessels especially that of the microcirculation. HVM devices have proven successful in identifying morphological changes in vessel structures and subcellular components associated with the severity of diabetes. Differentiation and quantification of the severity of disease in diabetes may be achieved by the IVM device using, say, AI analysis of the different components of the microcirculation, such as the morphology, leucocytes kinetics, subcellular structures glycocalyx. In some examples, the IVM device may provide/output this information in a point-of-care manner, as well as potentially providing a self-care type of IVM device.

Hypovolemia is a condition where there is insufficient volume of blood in the circulation to allow the heart to sufficiently pump blood to perfuse the microcirculation with oxygen rich blood. It can occur as a result of blood loss or dehydration (which is the primary cause of death amongst children worldwide). Hypovolemia is difficult to diagnose. However, in accordance with some optional examples of the invention, the IVM device allows precise identification and also enables a distinguishing between blood loss and dehydration.

Currently there is no direct; non-invasive imaging modality for assessment of a vascular health of an individual. According to examples of the present invention, the IVM device described herein is able to image and interpret the properties of the vasculture that would allow an individual (and also across a population) to track as a vascular bioprint the development of the vasculuture. Since the microcirculation is that part of the cardiovascular system that is closest to the tissues, it can be regarded as the most relevant to follow in this respect. It can be visualized by the IVM device, but needs interpretation and quantification, which can also be provided by the described IVM device. Being able to measure the microcirculation and interpret its health and response to lifestyle would allow one to track ones vascular health over time. Since it is known that exercise benefits vascular health, the IVM device can allow an individual (or patient) to assess the benefit of exercise for the development of the (micro) vasculture needed for cardiovascular health.

Extracorporeal organ support (EOS) comprises a number of different technologies, whose aim is to mechanically support failing organ systems, such as can occur for the lung (mechanical ventilation, venous-venous extracorporeal membrane oxygenation (VVECMO), the heart (left ventricular assist devices, vaneous arterial extracorporeal membrane oxygenation (VA-ECMO), the liver (molecular adsorbent recirculating system MARS) and the kidney (hemodialysis and continuous renal replacement therapy (CRRT). EOS can also be supplemented by specific extra devices such as adsorbers meant to extract various toxin. However objective criteria for attachment of such additional devices and evaluation of their efficacy in terms of benefit remain unavailable, prior to the IVM device described herein. The mentioned EOS technologies also include artificial organs placed in patients, such as artificial heart, kidneys and livers. Currently the efficacy of these known devices in supporting the cardiovascular system is uncertain, as no real quantitative clinical parameters exist that allows determination of whether the EOS is effective in supporting organ function and their microcirculation. The interpretation of MC images requires time consuming analysis off line and there is no current known technology that allows bedside interpretation of changes in response to, and/or providing advice on, how to proceed with EOS. The IVM device described herein advantageously provides such a technology platform to solve these problems.

Currently there is no direct, non-invasive mechanism to detect whether (or not) kidney disease is chronic or is in its acute form (acute kidney injury AKI) as it is difficult to predict and also difficult to therapeutically treat successfully. Therapies for such diseases besides treatment with drugs also include a use of renal support or replacement devices, including hemodialysis and continuous renal replacement therapy (CRRT). Known devices can also be supplemented by specific extra devices, such as adsorbers (specialized filters) that are meant to extract various toxins from the blood. However, objective criteria for attachment of such additional devices and evaluation of their efficacy of therapeutic modalities in terms of benefits, remain unavailable. The herein described IVM device is able to provide diagnostic bedside technology which is able to show a presence of disease, severity of disease and response to therapy, with the needed sensitivity and specificity, and identify the progress of disease and response to therapy. The IVM device described herein has been able to show a presence of MC alterations associated with kidney disease and its therapies, indicating that the IVM device provides a window of diagnostic capacity. Furthermore, in contrast to the current state of the art, the IVM device provides an interpretation of images and provides advice for therapeutic success, therapeutic titration and/or advice on applying alternative therapeutic strategies.

It is also known and acknowledged that brain function is especially difficult to assess, for example to assess its function and or the presence of brain disease, due to its inaccessibility. It is known that brain disease, which can occur and includes brain tumour dementia and Alzheimer as well as strokes, have an important cardiovascular component. The IVM device herein is able to analyse the MC and examine the functional properties of the vascular network, both in and on the brain, as well as in distant locations, and may provide information regarding the risk, presence or response to therapy regarding brain disease. In optional examples, the IVM device is able to be applied sublingually (small and large vessel disease) or adapted to the retina as well as applied during neurosurgery in order to provide a window of diagnostic possibility.

It is widely understood that blood transfusions and anaemia are an important part of medicine, where the presence of anaemia and identification of a need for blood transfusion and verification of whether therapies to correct anaemia have been sufficiently met is lacking. In addition to blood transfusions, other measures aimed at improving the availability of sufficient red blood cell mass and haemoglobin concentration, such as iron and EPO administration, require non-invasive diagnostic support. In addition to a need for a medical use, such measures at increasing the oxygen carrying capacity are also used for doping in sports. There is also a need for a non-invasive diagnostic technology to measure the use of such procedures. A mechanism to identify a high blood cell concentration, where there are abnormally high amount of red and white blood cell count such as occurs in polycythemia and leukemia can be provided by the IVM device described herein, without a need for the current requirement to withdraw blood. Advantageously, a bloodless, non-invasive methodology by the IVM device enables a clinician to visualize red and white blood cells.

There exists a need for objective metrics for determining that an organ can be transplanted from a patient, for determining the quality of organs to be transplanted as well as for determining a success of the transplantation and a consequent risk for rejection (long and short term). Currently, an ability to obtain these objective metrics is still lacking particularly in a non-invasive manner. Measurement of the MC on organ surface by an HVM device, as well on distant locations, has advantageously shown MC alterations associated with organ transplantation. Since the condition of the cardiovascular system is key in the need for transplantation, as well as on the success of transplantation and that there is no analysis methodology related to organ transplantation, the IVM device analysis of the MC during procedures where direct information is required, in support of clinical decision making, meets these needs.

There also exists a need for real-time diagnostic information during emergency medicine and trauma situations. For example, immediate information regarding triage and the resuscitation procedures are expected to have most benefit. Relatively few diagnostic technologies exist that can be used in a point-of-care method in the site of trauma or in an ambulance. Often, in these situations, immediate diagnostic support and decision making is needed in order to implement procedures such as blood transfusion, fluid administration or the administration of vasoactive medication. The IVM device described herein has been shown to detect with a high degree of sensitivity MC alterations associated with emergency medicine and trauma and importantly whether (or not) the administration of a type and amount of therapy has been successful in, say, correcting a cardiovascular collapse associated with emergency medicine and trauma.

It is known that benign and oncological gynaecology are in need of point-of-care diagnostics, in order to be able to identify, say at a bedside, a presence of disease and evaluation of the success of therapy. For diagnosis of a presence of gynaecological cancer, such as cervical cancer, the current state of the art is use of staining techniques (acetate staining) followed by analysis of a biopsy. This approach requires invasive and time consuming diagnostics, which are difficult to perform, especially in resource-poor environments, such as the third world. The IVM device according to some examples of the invention provides an alternative approach, by observing abnormalities of the MC by IVM endoscopy, for example combined with AI for identification and gradation of tissue pathology. This IVM device approach can also advantageously be used during gynaecological oncosurgery, for identification of a presence of tumours and micrometasis associated with for example ovarian cancer. In some examples, AI analysis and identification may aid a surgeon to identify cancer, resection margins and or provide a decision for surgical resolution of such cancers and/or for initiating chemotherapy or radiation therapy for point-of-care of decision making. The IVM device described herein may also be applied to gynaecology and urogynaecological diseases, including identification for a success of therapy for treatment of prolapse surgery (e.g., laser or surgical), as well as other urogynaecological disorders such as vaginal atrophy and its treatment by oestrogen therapy. Here, the described IVM device is able to identify the severity of atrophy and the efficacy and timing of oestrogen therapy.

It is also known that the presence of sickle cell anaemia (SCA) and the occurrence of a crisis is difficult to predict. In addition it is difficult to predict a success of any therapy. Indeed there is currently no on-line non-invasive diagnostic methodology that is available, other than blood withdrawal and subsequent off-line analysis. Since the abnormalities associated with SCA concern abnormalities with red blood cells and the crisis associated with SCA directly related to MC dysfunction, MC analysis by the IVM device described herein, for example using AI, may meet this need in the diagnosis and therapeutic resolution of SCA.

According to a second aspect of the invention, there is described a medical method. The method includes: receiving at least one IVM image sequence of a human microcirculation, MC, of an organ surface; processing the at least one IVM image of a human MC by a learning processor; extracting at least one MC variable from the processed at least one IVM image; identifying from the extracted at least one MC variable of the at least one IVM image at least one of: an underlying cause for an observed abnormality, an intervention, a disease state, a disease diagnosis, a medical state of the human; a presence of a pathogen; and outputting the identification.

These and other aspects of the invention will be apparent from, and elucidated with reference to, the embodiments described hereinafter.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the FIGs are illustrated for simplicity and clarity and have not necessarily been drawn to scale.

A more detailed understanding of the invention can be obtained by reading the text in conjunction with the figures presented at the end of the document. These figures present an example process flow of data handling and processing of microcirculatory images and clinical data with the purpose of presenting the user detailed information regarding features related to the microcirculatory images and underlying states of disease and health.

These figures are examples and the inventive concepts herein described are not limited to the specific methods and processes disclosed therein.

Figure 1:
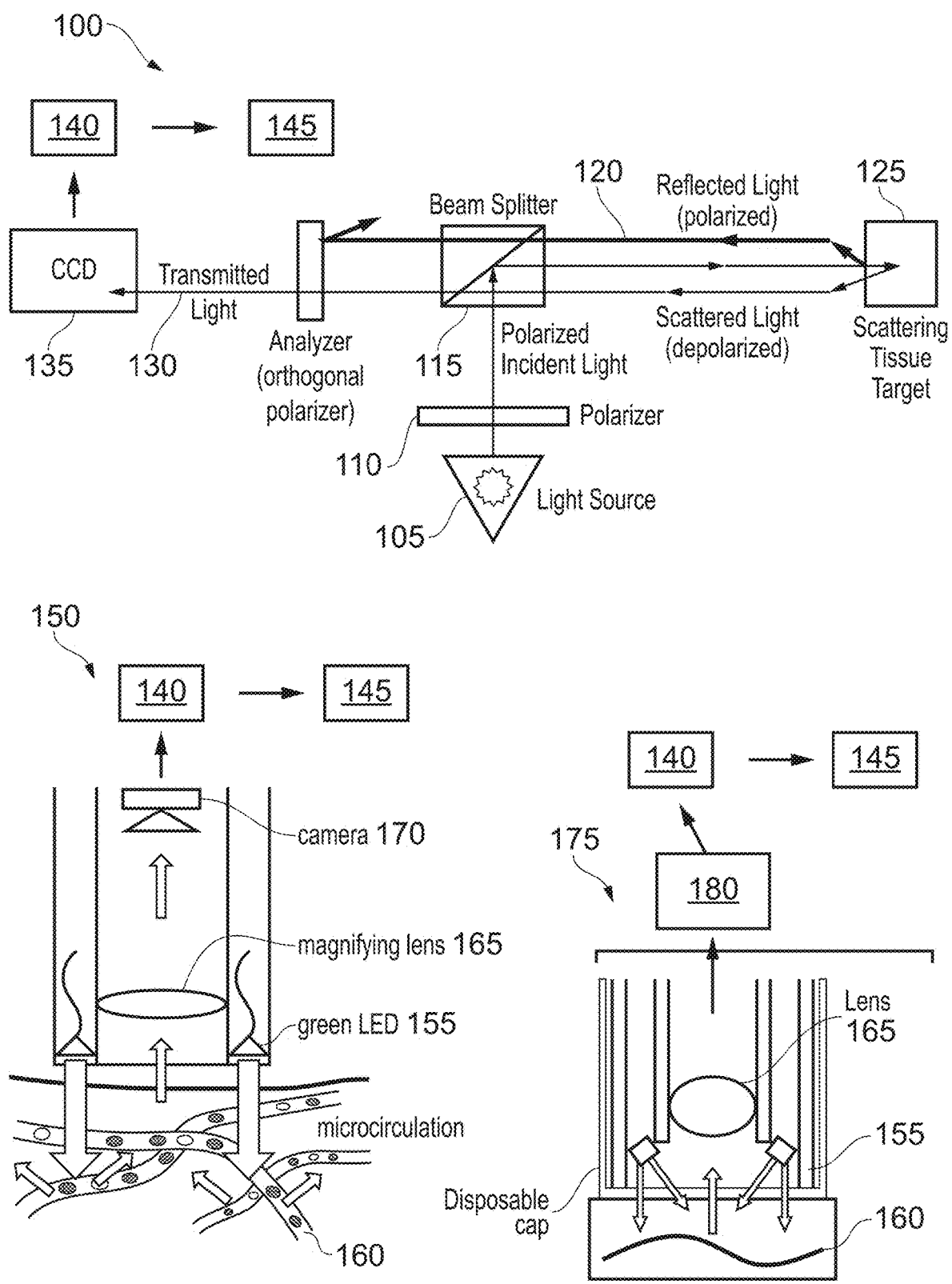

FIG. 1 illustrates the three main types of known handheld vital microscopy (HVM) devices currently available.

Figure 2:
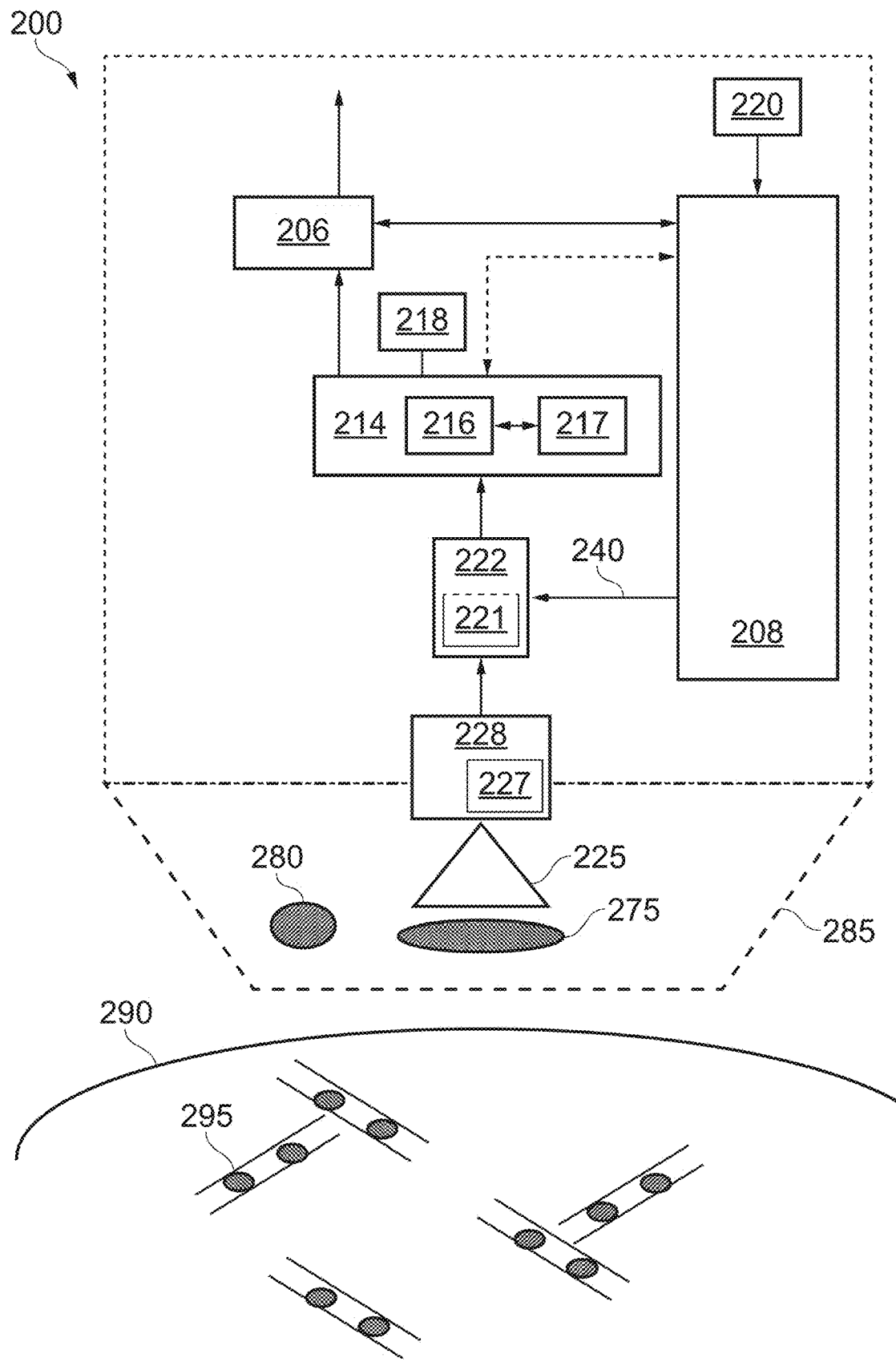

FIG. 2 illustrates an example block diagram of an intelligent vital microscopy, IVM, device for microcirculation analysis, for example to enable training and inference of neuronal networks for microcirculation analysis, in accordance with example embodiments of the invention.

Figure 3:
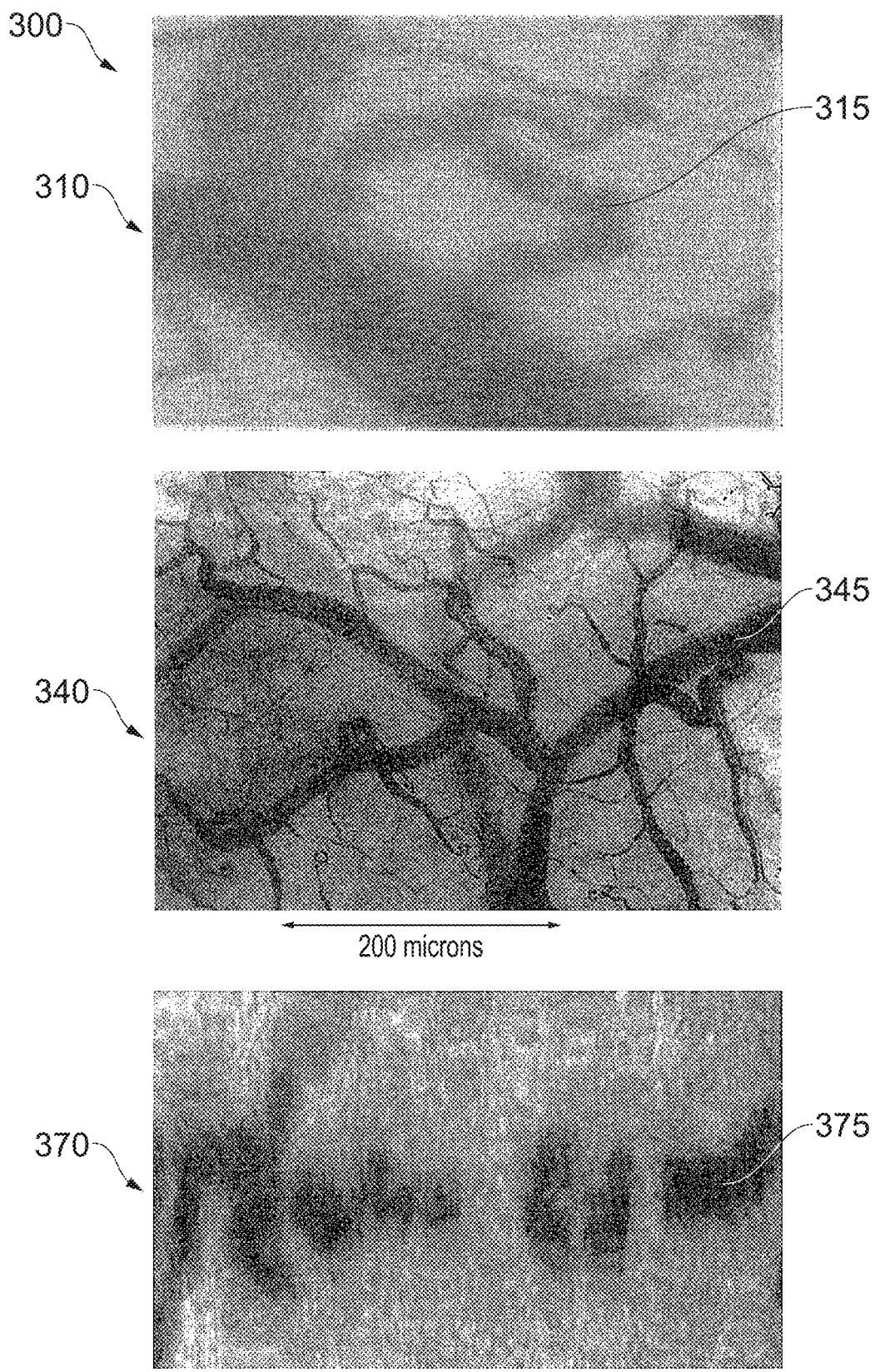

FIG. 3 illustrates a series of images of white and red blood cells obtained from an IVM image.

Figure 4:
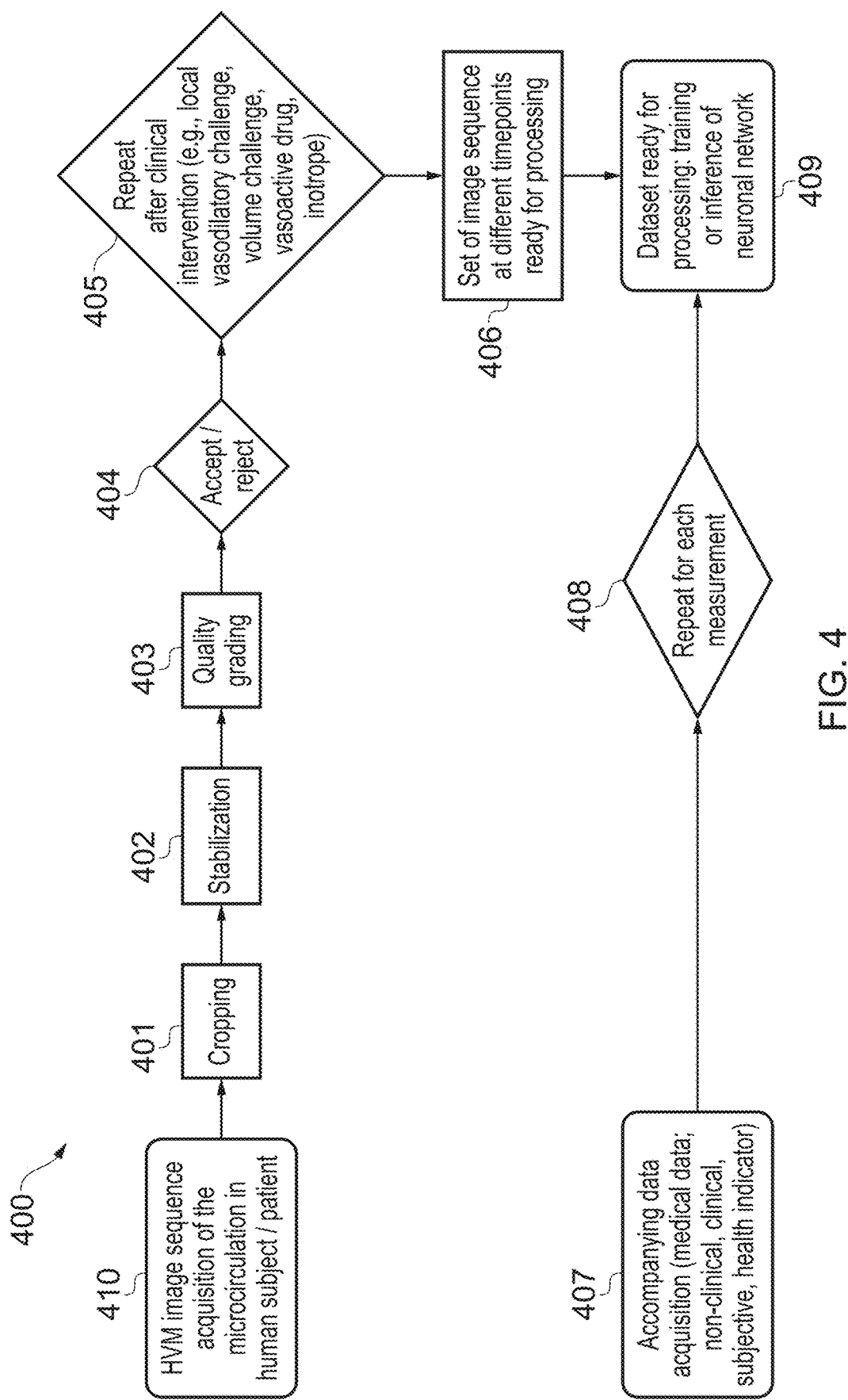

FIG. 4 illustrates an example of a flow diagram for an IVM device using artificial intelligence (AI), in accordance with example embodiments of the invention.

FIG. 5 illustrates an example of a neuronal network flow diagram for training and inference for classification (identification of features, e.g. disease states) or quantification (of relevant physiological microcirculatory parameters (RPMP)) of IVM image sequences of the MC and clinical data, in accordance with example embodiments of the invention. In particular, the example neuronal network may be employed for supervised learning (FIG. 5A) and unsupervised learning (FIG. 5B).

Figure 6:
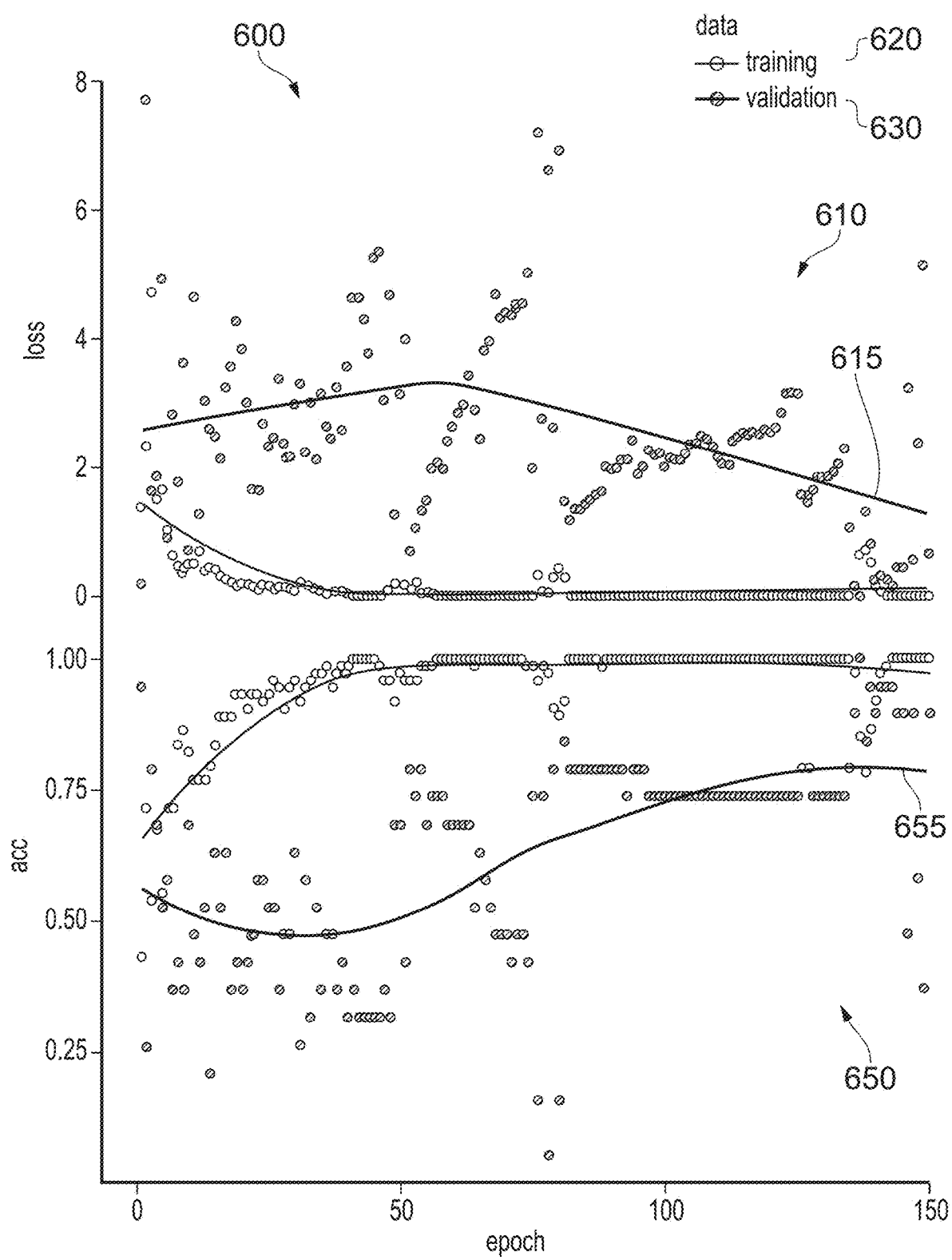

FIG. 6 illustrates an example of a training and validation of a two-dimensional convolutional neuronal network for identifying whether (or not) a sequence of microcirculation images is vasodilated; in accordance with some example embodiments of the invention.

Figure 7:
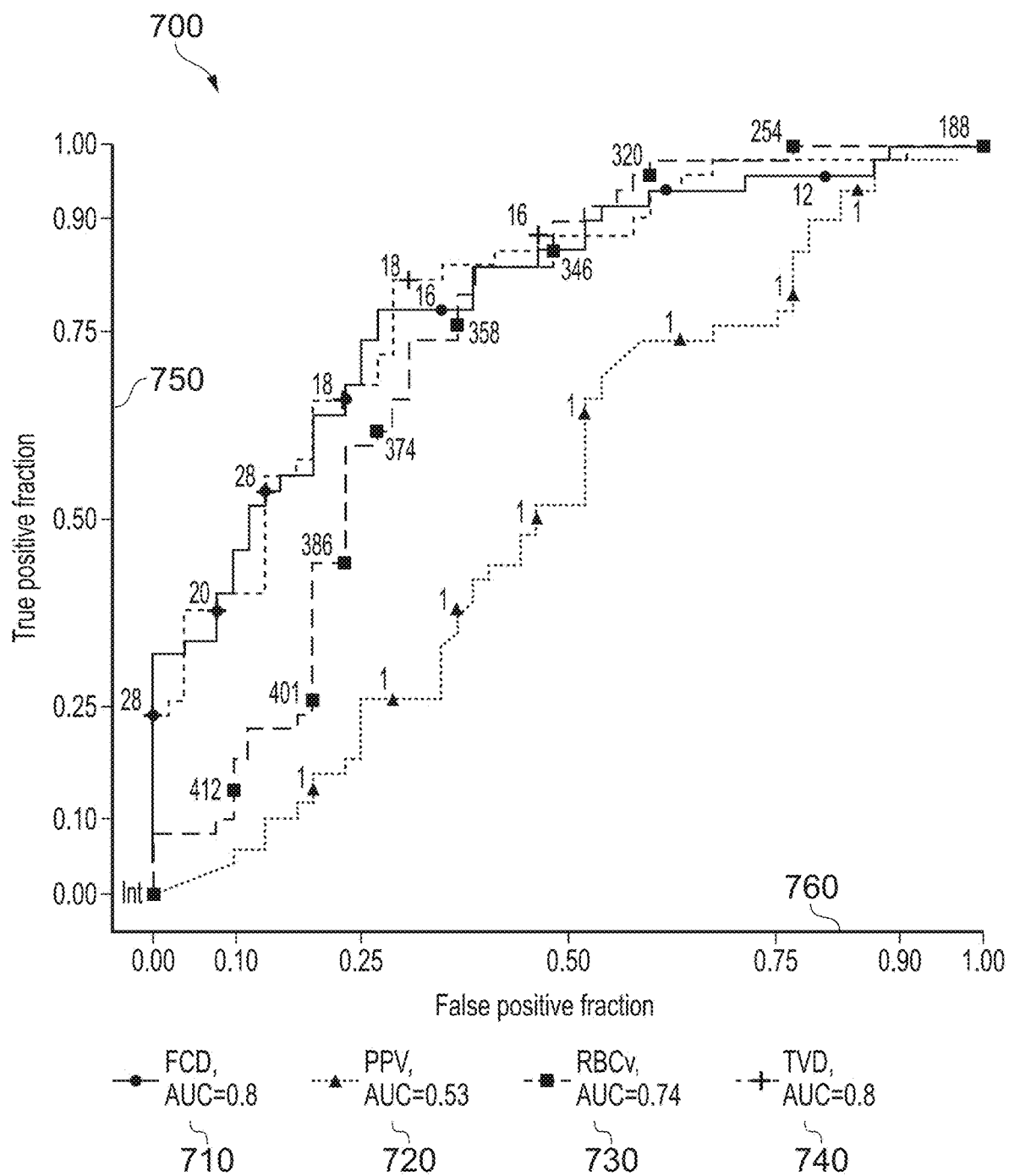

FIG. 7 illustrates a graphical identification example of microcirculatory vasodilation using standard analysis of intravital microscopy image sequences, in accordance with some example embodiments of the invention.

Figure 8:
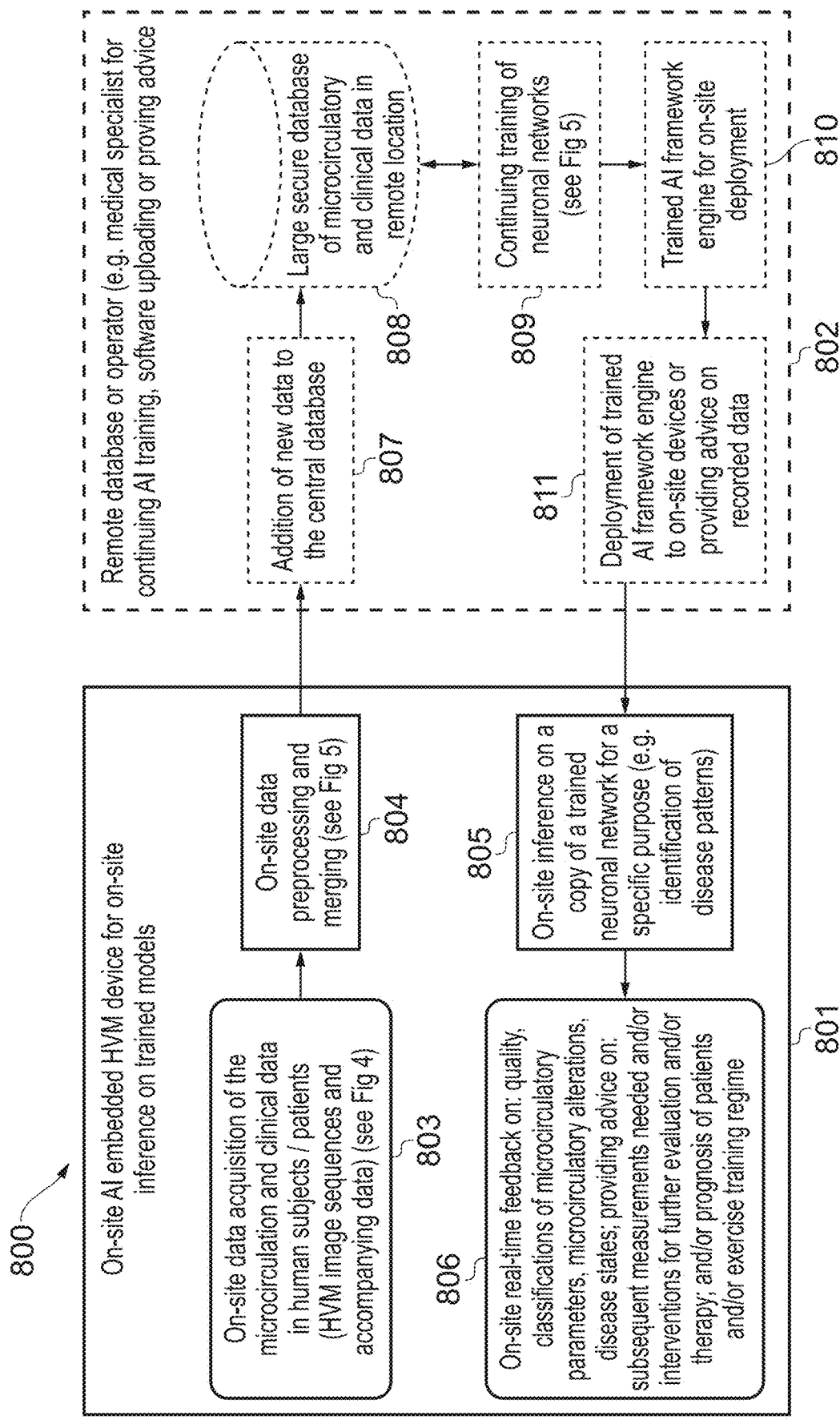

FIG. 8 illustrates an example of a flowchart or system diagram of on-site inference on a trained neuronal network for a specific purpose (e.g., identification of disease patterns in an IVM device of the microcirculation and clinical data), in accordance with some example embodiments of the invention.

Figure 9:
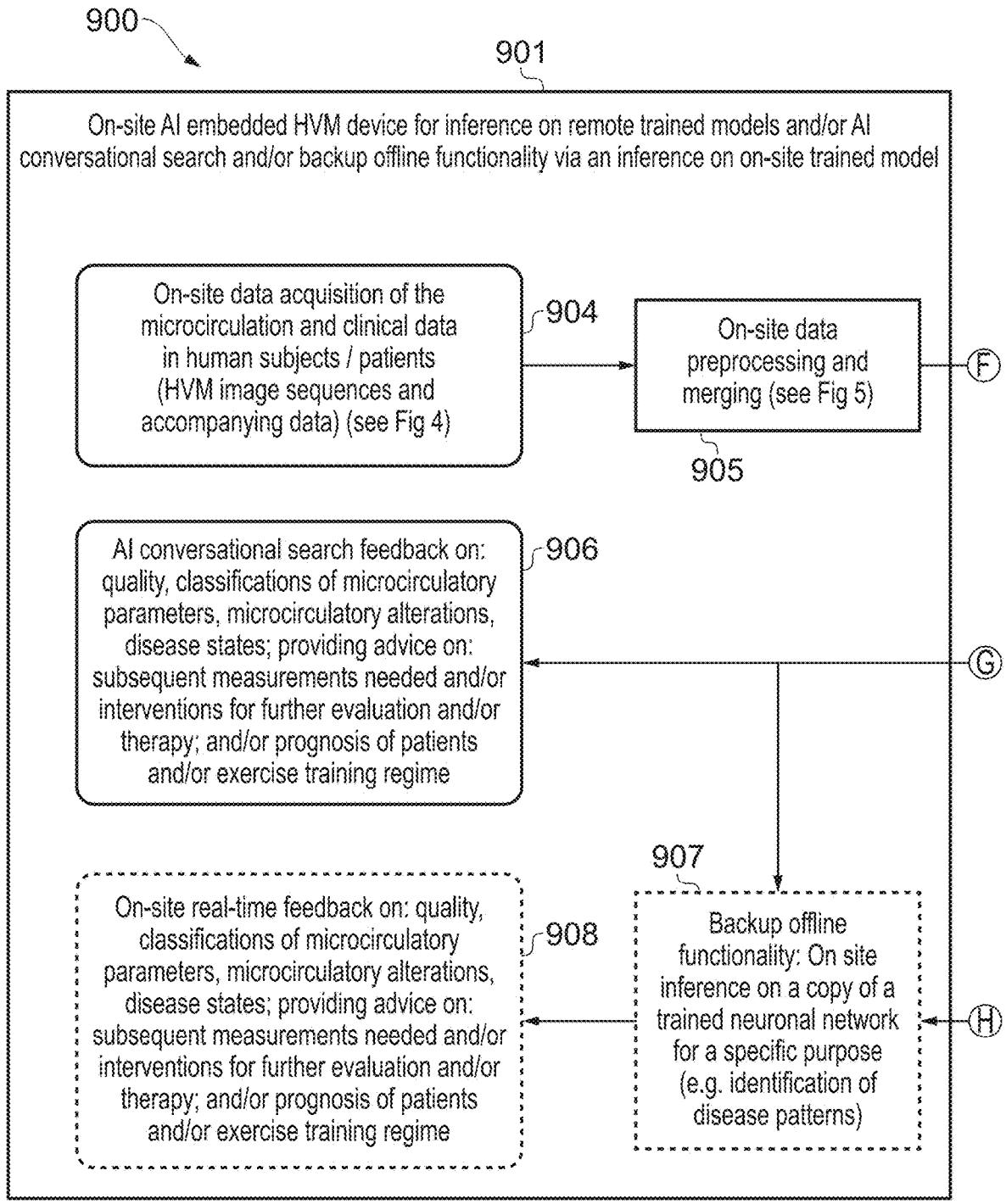
Figure 9:
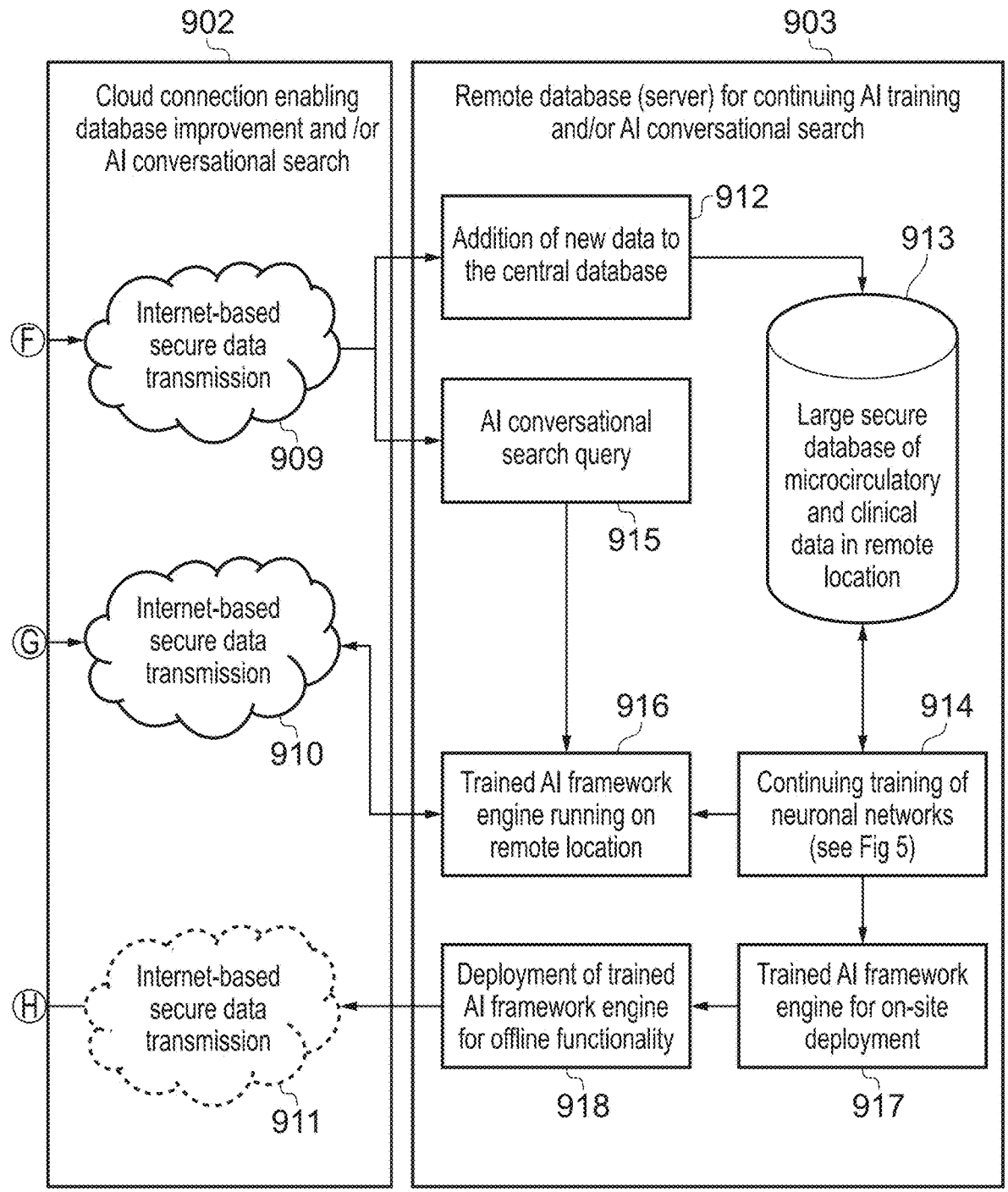

FIG. 9 illustrates an example of a flow process of a system for inference on a remote, cloud-based neuronal network for a specific purpose (e.g., identification of disease patterns in IVM images of the microcirculation and clinical data), AI conversational search, and data collection for continuing training of neuronal networks in remote location.

Figure 10:
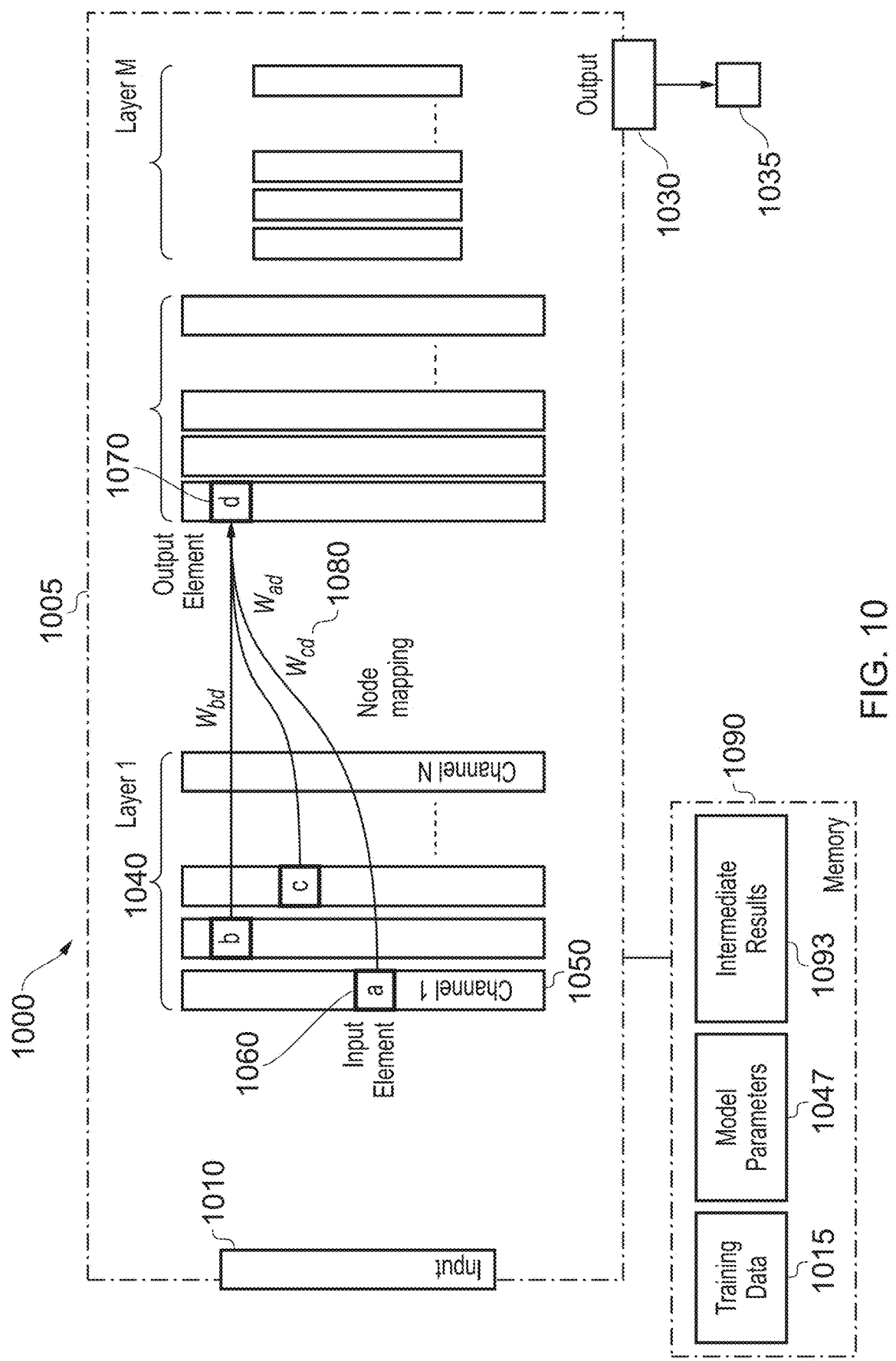

FIG. 10 illustrates an example of a neural network that may be employed as an artificial intelligence-based learning processor architecture to analyze the function and morphology of microcirculation according to some examples of the present invention.

DETAILED DESCRIPTION

Current algorithm-based image analysis of HVM images/movies, in order to extract microcirculatory functional parameters, is difficult and requires the application of time consuming off-line analysis of HVM movies. The inventors of the present invention have recognised and appreciated that there is no methodology that directly links, on-line, the microcirculatory alterations to their causes or underlying disease states. Furthermore, the inventors of the present invention have recognised and appreciated that, based thereon, there is no consequent advice for a therapeutic resolution of said disease states. Consequently, the inventors of the present invention have recognised and appreciated that this is the main obstacle restricting a much wider use of vital microscopy as a point-of-care for diagnostic modality.

Although examples of the invention are described with reference to an intelligent vital microscopy, IVM, device to observe microcirculation of a processed image or sequence of images, it is envisaged that the concepts described herein are equally applicable to hand-held vital microscope (HVM) device, non-held microscopic devices such as intra-vital microscopes, endoscopes, non-hand held miniature vital microscope fixated to an organ surface, fundus cameras and surgical microscopes equipped with suitable optics to image the microcirculation. Thus, hereafter, the term IVM device used herein is intended to encompass all such vital microscopes, which are embedded or placed on tissue surfaces for on-line visualization of the MC. These include microscopy embedded in operating microscopes, intravital microscopes or endoscopes. Fluorescence spectroscopy can be incorporated into the IVM device to obtain spectroscopic information about plasma and tissue molecular and particle constituents. Miniaturized non-held IVM devices can be fixed or implanted in the oral region or other locations in the body to enable continuous visualization of the microcirculation and assessment by the learning processor. Such miniaturized non-held IVM devices will benefit largely from the concepts described herein because continuous evaluation of an evolution of the MC will allow early therapy to be initiated in advance of clinical deterioration of the patient. Thus, examples of a IVM device described herein, as well as the term 'IVM device' used herein, is intended to additionally cover this range of devices. It is further envisaged that the concepts described herein may be embodied in any scenario, application or system where vital microscopy methodology of acquiring MC images of organ surfaces may be used.

Although examples of the invention are described with reference to an intelligent vital microscopy, IVM, device to observe sublingual microcirculation of a processed image or sequence of images, it is envisaged that the concepts described herein are equally applicable to observe sublingual microcirculation of a processed image or sequence of images of any organ surface. Thus, examples of an IVM device described herein to observe sublingual microcirculation from a processed image or sequence of images, is intended to cover an observation of microcirculation of any organ surface from a processed image or sequence of images.

Some examples of the invention described herein propose a use of a learning processor embedded in the IVM device in order to provide real-time, on-line analysis of images for identification of an underlying disease. In some examples, the real-time, on-line analysis of images for identification of an underlying disease may also include a suggestion for a use of therapy, for example both for clinical decision making at a bedside and needed for titrating therapy. These learning processor approaches may provide sensitive analysis of images in order to identify MC alterations and identify (for example in an unsupervised format) as yet uncovered information regarding the health and disease of patients, for example information obtained from one or more MC parameters extracted from a processed one or more IVM image.

For the aid of the reader, a number of definitions of medical terms are detailed at the end of the detailed description.

Figure 5A:
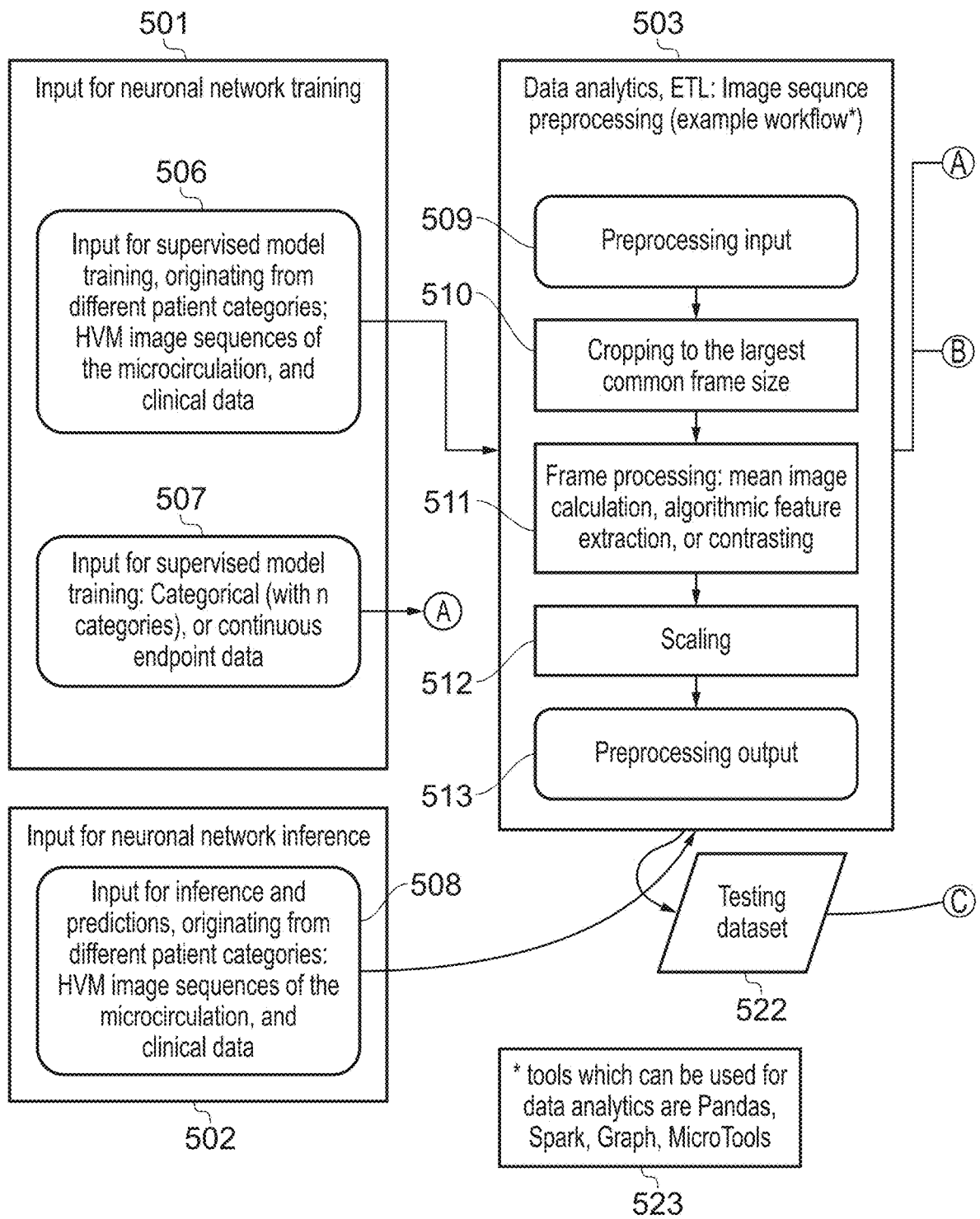
Figure 5A:
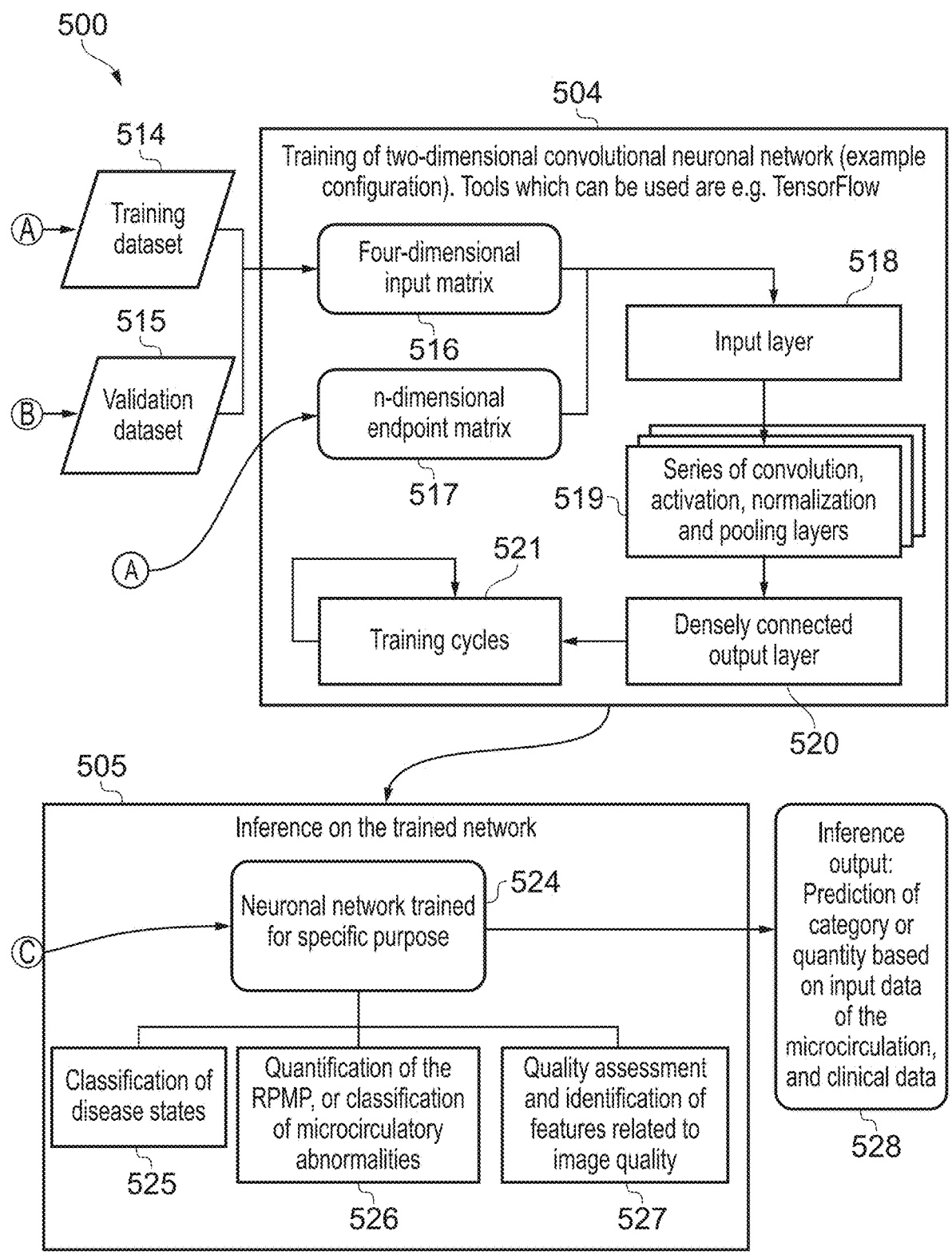
Figure 5B:
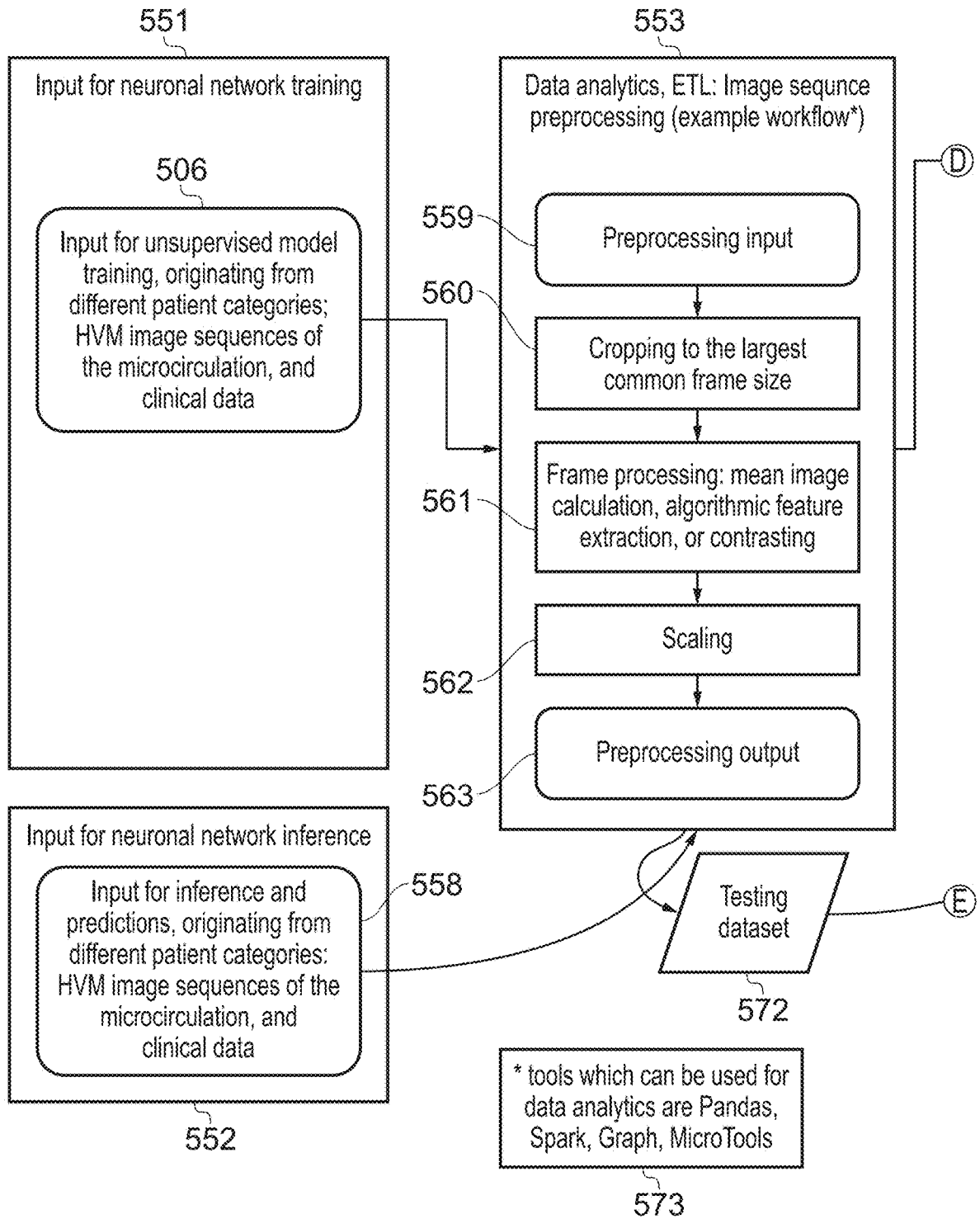
Figure 5B:
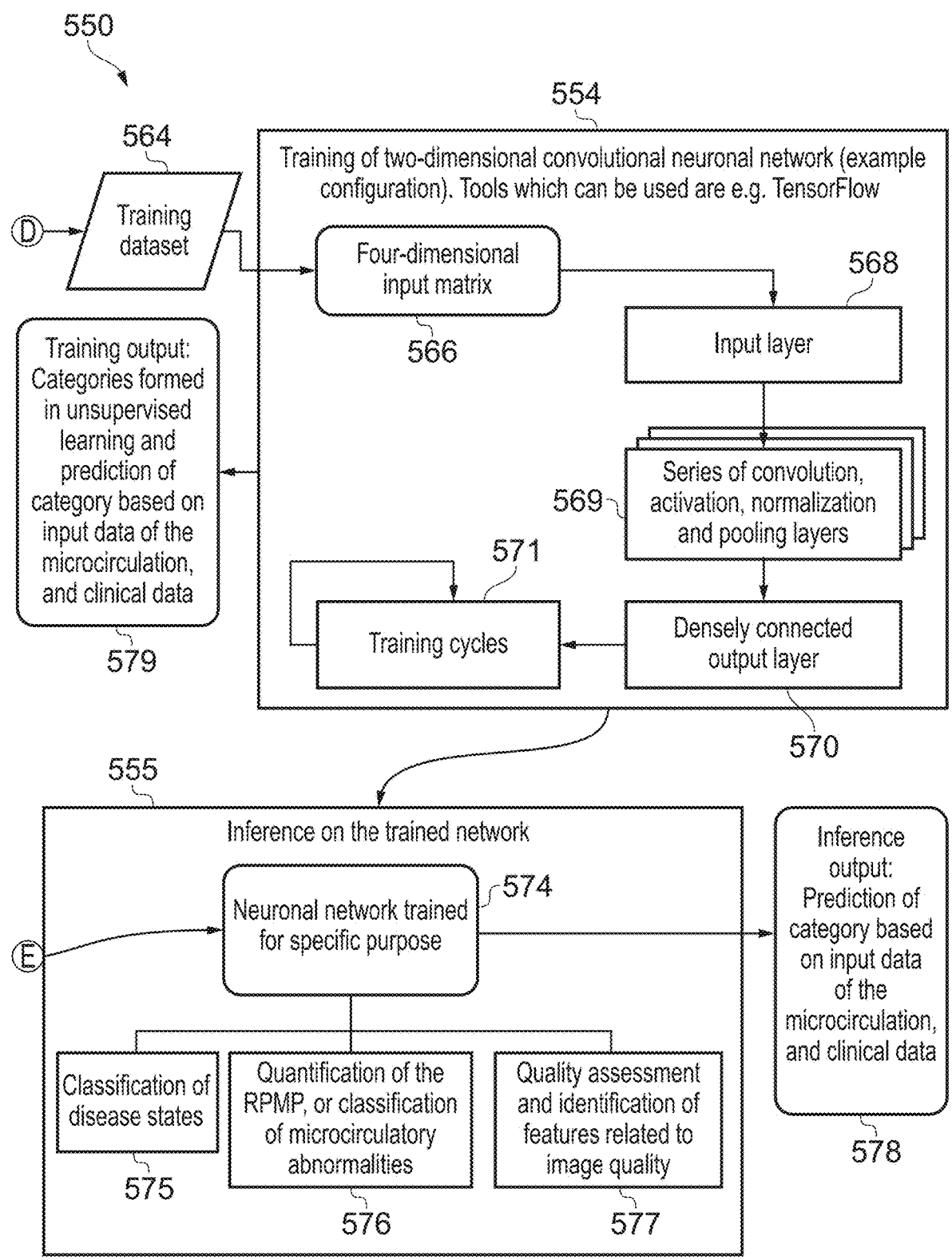

In some examples, it is envisaged that the concepts described herein can utilize an artificial neural network, which encompasses a network of artificial neurons and nodes designed for solving learning processor problems, such as those in artificial intelligence (AI). In some examples, the connections of the artificial neurons may be weighted to model excitatory or inhibitory connections, which may then be summed. In some examples, an activation process may be used to define an amplitude of the output. In some examples, the artificial neural networks may be used for predictive modelling and adaptive control. In this manner, such neural networks may also be trained via a dataset. In some examples, it is envisaged that self-learning or unsupervised learning resulting from analysis of data sets (as illustrated in FIG. 5A and FIG. 5B) of processed MC images may occur within the neural networks, which allows the neural network to derive conclusions from a seemingly unrelated information set. In some examples of the invention, such methodology may be integrated into the functionality of an IVM device, for example at a bedside in a point-of-care fashion, in order to provide direct information regarding an origin of a functional state of the MC, its related disease state, advice for therapy and identifying an outcome, etc. In some examples, the IVM device may be able to remotely obtain such information, if stored in a large database that the IVM device is connected to, for example in a wireless (or indeed wireline) configuration.

In some examples of the invention, when the term artificial intelligence is used herein, it is intended to encompass any form of supervised processor learning or unsupervised processor learning, as well as machine learning (ML). Examples of such processes are shown in FIG. 5A and FIG. 5B.

FIG. 2 illustrates an example block diagram of an intelligent vital microscopy, IVM, device 200 embodied with a learning processor to enable training and inference of neuronal networks for microcirculation analysis, in accordance with example embodiments of the invention.

In practice, purely for the purposes of explaining embodiments of the invention, the device to diagnostically analyze the function and morphology of the microcirculation of humans in order to evaluate a state of health of a subject is described in terms of an IVM device 200, although it is envisaged that other microscopy devices (such as conventional intra-vital microscope magnification embedded in an operational microscope or an endoscope), architecture, may be employed to utilise the inventive concepts described herein. The IVM device 200 includes a controller 214 that maintains overall operational control of the IVM device 200. The controller 214 is coupled to a signal processor 208, which is generally realized by a Digital Signal Processor (DSP). A skilled artisan will appreciate that the level of integration of receiver circuits or components may be, in some instances, implementation-dependent. In some examples, the signal processor 208 may include a health and clinical decision making circuit 221 or processor that is configured to analyse AI data related to at least one function and morphology of a microcirculation of humans, in order to evaluate a state of health of a subject. In some examples, the clinical decision making circuit 221 may exist external to the IVM device 200.

In some examples, the controller 214 is also coupled to a buffer module 217 and a memory device 216 that selectively stores data relating to operating functions of the IVM device 200. A timer 218 is operably coupled to the controller 214 to control the timing of operations (e.g. transmission or reception of time-dependent signals) within the IVM device 200.

The IVM device 200 includes a learning processor 222, which in some examples may be implemented as a neural network, as shown in FIG. 9. The learning processor 222 may be operationally responsive to the controller 214. In some examples, the signal processing module 208 and/or controller 214 may receive inputs from one or more input device or sensor modules 220, for example which may receive one or more clinical variables.

In example embodiments, the learning processor 222 may include (or be operably coupled to) an image acquisition and pre-processing circuit 221, which may be configured to organise the input data into a suitable format. In some examples herein described, the input image data received by the image acquisition and pre-processing circuit 221 may be provided by a camera 225 coupled to a receiver 228 comprising a video camera/image capture circuit 227. In some examples, the video camera/image capture circuit 227 may include or be operably coupled to a focusing circuit/mechanism to focus the image provided by the camera 225. In this example, the IVM device 200 includes a disposable, see-through cap 285, to allow unfettered access to the subject's tissue 290.

An HVM is usually housed in a tube consisting of a magnifying lens 275, focus mechanism, and image sensor/video camera and a data acquisition module (not shown). In this example, the IVM device 200 to analyze the function and morphology of the microcirculation of humans in order to evaluate a state of health of a subject may also consist of different coloured LEDs 280 allowing multiple wavelength analysis of the images to extract spectroscopic information regarding the oxygen saturation of the haemoglobin in the red blood cells 295 or spectroscopic information about the composition of the tissue 290 cells. In FIG. 2, the tissue surface 290 is shown with microcirculation microvessels embedded with flowing blood cells 295 visible.

In alternative examples of the IVM device, other microscopic modalities may be incorporated into the IVM device in order to enhance the imaging capacity of the IVM device to identify sub-cellular structures (e.g., endothelial glycocalyx, cell to cell junctions, mitochondria, nuclei) and platelets, as well identification of the type of blood cells present in the microcirculation. Furthermore, in some examples, it is envisaged that the IVM device may be used to observe microorganisms, such as viruses, parasites and bacteria. Furthermore, in some examples, it is envisaged that the IVM device may be adapted such that spectroscopy may be used, for example to allow composition of cells to be determinants, such as an amount of collagen in cells obtained by polarization spectroscopy and the redox state of the mitochondria obtained by NADH fluorescence. Additionally, in some examples, it is envisaged that the IVM device may be configured to analysing more than just a single instance in time, in that it may be configured to also analyse changes occurring over time, in order to identify progress of health or disease or response to therapy.

In some examples, the IVM device 200 is a handheld-microscope that is able to image moving blood cells in the microcirculation, as well as imaging the structure of the microvessels (as shown in FIG. 3). In operation, the IVM device 200 may be held on or above an organ surface or a subject's/patient's tissue, in order to provide an on-line, real-time visualization of the microcirculation and their cellular constituents embedded within flowing blood cells and observed through the microvessels. In some examples, the IVM device 200 is a miniaturized non-held IVM device, which can be fixed or implanted in the oral region or other locations in the body to enable continuous visualization of the microcirculation and assessment by the learning processor. Such a miniaturized non-held IVM device will benefit largely from the concepts described herein because continuous evaluation of an evolution of the MC will allow early therapy to be initiated in advance of clinical deterioration of the patient. In accordance with some examples of the invention, the use of real-time AI techniques in this process may assist immediate processing and classification of microcirculation microvessels images and enable interpretation of the image data for an accurate diagnosis, choice of therapy and/or assist clinical decision making.

The IVM device 200 also includes a power supply (not shown), a light guide with a magnifying lens 275 at its tip and suitable illumination modality for illuminating an organ surface. Acquired images are routed to an image acquisition circuit, which can be a video camera or an image acquisition sensor. In other examples, the IVM device 200 may also include a conventional intra-vital microscope, or a hands free vital microscope fixated on to a tissue surface, or an operation microscope or endoscope, equipped with suitable magnification to view the microcirculation in organ surfaces.

In the IVM device 200 described herein, the learning processor 222, which in some instances may be implemented as an artificial intelligence (AI) processor, may be integrated in the IVM device 200 in order to allow identification, quantification, optimization, classification and interpretation of the images as well as identifying a health care strategy based on AI insight. The learning processor 222 is configured to extract at least one MC variable from a processed MC image or sequence of MC images, and identify from the extracted at least one MC variable of the at least one IVM image at least one of: an underlying cause for an observed abnormality, an intervention, a disease state, a disease diagnosis, a medical state of the human; a presence of a pathogen. In some alternative examples of a system configured to analyze the function and morphology of the microcirculation of humans in order to evaluate a state of health of a subject, it is envisaged that the AI circuit can be physically integrated into an IVM device (or system) or be placed off-line in a PC, mobile telephone or in the cloud, for example. The IVM device 200 includes an output 206 coupled to the learning processor 222, for example via the controller 214, and configured to output from the learning processor 222, an identification of the extracted at least one MC variable from the MC image or sequence of MC images.

Thus, an intelligent vital microscopy, IVM, device 200 is described that comprises: a receiver 228 configured to receive at least one IVM image of a human microcirculation, MC, of an organ surface; a learning processor 222 coupled to the receiver and configured to: process the at least one IVM image and extract at least one MC variable therefrom, and identify from the extracted at least one MC variable of the at least one IVM image at least one of: an underlying cause for an observed abnormality, an intervention, a disease state, a disease diagnosis, a medical state of the human; a presence of a pathogen; and an output 206 coupled to the learning processor 222, for example via the controller 214, and configured to output the identification.

Clearly, a number of the various components within the IVM device 200 can be realized in discrete or integrated component form, with an ultimate structure therefore being application-specific or design-based.

Referring now to FIG. 3, a series of pictures 300 of white and red blood cells in microcirculation analysis is illustrated, which can be analysed using AI techniques according to examples of the invention. In a first illustration 310, white blood cells are shown as white cells 315 in the arched capillary in the middle of the picture. In a second illustration 340, microcirculation vessels 345 are shown with blood flow therein, as seen in moving cells. In a third illustration 370, flowing single red blood cells are illustrated 375 in sublingual in magnified microcirculation recorded by an HVM device. Red blood cells have a diameter of about 5 micrometers in this example. For clarity purposes only, note that the dimensions of the field of view in these illustrations are approximately 200 microns.

Referring now to Table 1 below, a composition of the neuronal network used for identification of microcirculatory vasodilation is illustrated.

| layer type | kernel size/pool size/units | activation | remarks |
| --- | --- | --- | --- |
| input -> 2D conv | 3, 3 | RELU | 32 filters |
| batch normalization | | | |
| 2D max pooling | 3, 3 | | |
| dropout | | | rate = 0.25 |
| 2D conv | 3, 3 | RELU | 64 filters |
| batch normalization | | | |
| 2D conv | 3, 3 | RELU | 64 filters |
| batch normalization | | | |
| 2D max pooling | 2, 2 | | |
| dropout | | | rate = 0.25 |
| 2D conv | 3, 3 | RELU | 128 filters |
| batch normalization | | | |
| 2D conv | 3, 3 | RELU | 128 fitters |
| batch normalization | | | |
| 2D max pooling | 2, 2 | | |
| dropout | | | rate = 0.25 |
| flatten | | | |
| dense | 1024 units | RELU | |
| batch normalization | | | |
| dropout | | | rate = 0.5 |
| dense -> output | 2 units | softmax | |

The output size of each module is the input size of the next one, where the acronym RELU refers to a rectifier linear unit. Table 1 describes the composition of the convolutional neuronal network used for prediction of microcirculatory vasodilation. In short, the input layer is connected via a rectified linear units activation functions (RELU) to a module consisting of a two-dimensional convolution layer (2D cony) followed by batch normalization to reduce covariance shift, sample-based discretization via two-dimensional max pooling, and coadaptation prevention via a 25% dropout layer (module A). The output is then routed via RELU to a module consisting of a two-dimensional convolution layer followed by batch normalization (module B) followed by a module A using an increasing number of filters to reduce the matrix size. After another sequence of module B→module A with an increasing number of filters, the output is routed via RELU to a dense layer, again batch normalized and routed to a 50% dropout layer to a final dense layer that produces the two-category output via a softmax activation function.

The Microcirculation

The main function of the microcirculation is to deliver oxygen to the tissues by oxygen carrying red blood cells (RBC) to meet their metabolic needs for optimal cellular function required to enable them to support organ function. It is also the main compartment involved in the immune system where leucocytes interact with vessels and tissue cells to exert their functional activity. In states of infection and inflammation leucocytes and endothelial cells become activated and leucocytes will stick and roll along the endothelial wall and eventually extravagate into the tissues. The activity of the leucocytes can be observed and quantified using IVM device observations and indicate the presence of inflammation (see reference [9]). In shock, variables related to MC function become compromised and precedes all forms of cardiovascular compromise associated with the different forms of shock, as well as a large range of disease states, which is a condition referred to as a loss of hemodynamic coherence (see reference [10]). One problem associated with states of shock is that it is very difficult to identify which type of shock is occurring in the patient, and therefore as a consequence which therapy is expected to have most benefit to the patient in terms of response and outcome. This is especially difficult in sepsis, where other parameters may seem normal (loss of hemodynamic coherence see reference [10]).

The alterations seen in the microcirculation during sepsis and septic shock are very specific including heterogeneous perfusion of the microcirculation with plugged vessels next to ones where there is flow. Alterations in the MC represent the most sensitive and specific hemodynamic alteration seen in the cardiovascular system more so than systemic hemodynamic variables. Such sepsis associated alterations detected under the tongue can be associated with severe organ dysfunction and lack of responsiveness to therapy whereas systemic variables do not show such discrimination. It is envisaged that the ability to distinguish between infection and sepsis and its response to therapy, which currently is an important clinical problem, may be possible using IVM analysis of the MC.

In cancer the functional state of the microcirculation is key in the interaction between the metabolic requirements of the tumour and its microcirculation. The inventors have recognised and appreciated that knowledge relating to the microcirculation, either on the tumour or at a distant location, would be beneficial in identifying the stage of the tumour and the optimal therapy and therapeutic target that needs to be applied. Other chronic disease states, such as diabetes, kidney disease, heart failure and hypertension can also be identified by known HVM observations, although there is no known HVM methodology that presently distinguishes between these different disease states. In some examples of the invention herein described, all functional and anatomical information regarding blood vessels are considered and encompassed by the concepts described herein, from the largest (aorta) to the smallest vessels (capillaries), despite the examples being primarily described with reference to the microcirculation.

In some examples of the invention, the learning processor is configured to process and extract at least one MC variable from a processed MC image or sequence of MC images. In some examples of the invention, the extracted at least one MC variable may include at least one of: a quantification of a morphological parameter of the MC, at least one functional parameter of the MC. In some examples of the invention, the extracted at least one MC variable may be the Functional Capillary Density (FCD) or tissue red blood cell perfusion (tRBCp) or Total vessel density (TVD) or leucocyte kinetics. In some examples of the invention, the extracted, identified at least one functional parameter of the MC may include at least one of: MC hemodynamic values; capillary; a venule; arteriolar blood flow; blood volume; an identification of at least one type of vessel; a proportion of perfused vessel density, PVD; a proportion of functional capillary density, FCD, of flowing red blood cells, RBC, that carry oxygen; tissue RBC perfusion; a vessel diameter, VD; a RBC and leucocyte velocity; a proportion of perfused vessels, PPV, a microvascular flow index of a flow heterogeneity, MFIhet; rolling and sticking leukocytes, fluorescence spectroscopy of a number of platelets and leucocytes; microcirculatory RBC haemoglobin (Hb) saturation; a capillary tube and discharge haematocrit.

In examples of the invention, a distinction is made between the macro-vasculature (blood vessels >100 μm including arteries and veins) and the microcirculation (blood vessels <100 μm) consisting of capillaries, arterioles and venules. The former vessels can be detected by MRI, angiography, echo, optical coherence tomography, fluorescence angiography of such organs as heart, brain and retinal vascular structures. In examples of the invention, the microcirculation can be detected by the IVM device, intravital microscopy (including fluorescence and capillaroscopy). Although other techniques are used to indicate information regarding the function of the microcirculation, such as: spectrophotometry, laser speckle imaging, contrast enhanced echo, oxygen electrodes, CO2 tonometry and near infrared spectroscopy and lactate measurements, only the IVM device can directly image the capillaries and the movement of single blood cells in them, thereby allowing uniquely the ability to provide quantitative information regarding the functionality of the MC. In examples of the invention, the term IVM is used to also include non-handheld vital microscopes, which are embedded or placed on tissue surfaces for on-line visualization of the MC, such as being embedded in operating microscopes, intravital microscopes or endoscopes. Fluorescence spectroscopy can be incorporated into the IVM device in order to obtain spectroscopic information about plasma and tissue molecular and particle constituents. In addition, histological information concerning microcirculatory morphology can be obtained from biopsy analysis and optical coherence tomography. These can also be used as input variables for AI. Miniature devices implanted in the oral region or other locations in the body will enable continuous visualization of the microcirculation. These will benefit greatly from the examples described herein because continuous evaluation of the evolution of the MC will allow early therapy to be initiated in advance of clinical deterioration of the patient. In some examples, AI will follow changes the functional state of the MC and identify the state of health and disease and response to therapy. Some examples of the invention described herein propose to analyze these variables using AI to gain a deeper understanding and identification of the state of health, disease and response to therapy.

The microcirculation has until now been most studied using hand-held vital microscopes (HVM). These devices (as illustrated in FIG. 1) include OPS imaging (see reference [5]) SDF imaging (see reference [6]) and IDF imaging devices (see reference [8]) as stand-alone (i.e. non hand-held but placed at a location in the body for continuous monitoring) or in combination with other techniques. These cameras have been used extensively to observe sublingual and oral microvascular structures and function in disease and health (see reference [11]). These techniques have also been used to observe microcirculatory structure in other human orifices as well as on human organ surfaces during surgery. Structures that are observed include flowing red and white blood cells, vessel structures and morphology, parenchymal cells as well as subcellular structures such as endothelial glycocalyx, platelets, cell and vascular and cell junctions as well as nuclei.

The extensive description of the IVM device enables a skilled person to replicate the various concepts herein described including the HVM components as well as AI and ML components of the IVM device. For completeness for the description of the HVM and its use, the reference [11], namely 'Second consensus on the assessment of sublingual microcirculation in critically ill patients: Results from a task force of the European Society of Intensive CareMedicine', authored by: Ince C, Boerma E C, Cecconi M, De Backer D, Shapiro N I, Duranteau J, Pinsky M R, Artigas A, Teboul J L, Reiss I K M, Aldecoa C, Hutchings S D, Donati A, Maggiorini M, Taccone F S, Hernandez G, Payen D, Tibboel D, Martin D S, Zarbock A, Monnet X, Dubin A, Bakker J, Vincent J L, Scheeren T W L and published in the Intensive Care Medicine, 2018 March; 44(3):281-299, is incorporated in its entirety herein by reference.

Spectrophotometry can be used to evaluate the state of oxygenation of the microcirculation and can be used in combination with the IVM device as well as spectroscopy (e.g. Raman spectroscopy) to obtain molecular information about plasma and tissue molecule information providing additive integrative information about microcirculatory hemodynamic and oxygenation variables together. Similarly, oxygen electrodes or BOLD can be used to measure the tissue oxygenation as well the assessment of mitochondrial oxygen tension using the decay of delayed fluorescence of mitochondrial protoporphyrin. An IVM can also be implemented as a stand-alone device where a microscope sensor placed on an organ surface independently monitoring continuously to obtain microscopic images of the MC. Such one-spot measurements would allow AI analysis of the behaviour of blood cells in single micro vessels. Such images could be analyzed locally in a point-of-care setting or be analyzed in a remote location (e.g. telemetrically to a mobile cell phone), Addition of spectrophotometry or other spectroscopic techniques can be used to obtain even more detailed MC and tissue information, Other techniques which can be used to observe the MC include fluorescence or con focal microscopy which can be incorporated into such IVM devices. Such microscopic information can also be obtained by microscopic endoscopy where a magnifying lens is attached to the end of an endoscopy and imaging of the MC is achieved either by optical fibers or by placement of a high definition camera placed at the tip of the endoscope. Alternatively, imaging capsules introduced intra-gastrically can also be used observe (micro)vascular structures. All of the above measurements are considered to provide information regarding the MC.

Artificial Intelligence (AI)

In some examples of the invention described herein any reference to AI encompasses a mathematical methodology to extract information from signals and images that may be similar to that used in cognitive functions in humans associated with learning or pattern recognition, in a supervised or unsupervised deep learning setting (see FIG. 5A and FIG. 5B). Here, flexible adaption is able to extract information previously not necessarily recognized or hypothesized or based on manually derived algorithms specific to the measurement of defined parameters. In the former case, AI in the setting of unsupervised learning is able to exploit serendipity in much the same way as scientific discoveries are made by chance.

Machine Learning (ML)

In some examples of the invention described herein, any reference to ML, as distinct from AI, may be used as a mathematical methodology that refers to mathematical and statistical methods, which can without supervision, analyze and identify a specific outcome related to in the case of this paper health and disease. It applies to algorithms and iterative methodologies to arrive at an optimal identification of a set task. It is used for data mining. Some examples of the invention described herein propose ML to be used to quantify morphological and functional aspects of the microcirculation being used as input variables with the aim of identifying health disease or outcome of therapy. For simplicity of terminology, however, any reference to AI examples of the invention described herein encompass supervised and unsupervised learning, as well as Machine Language.

Neural Networks

An artificial neural network is a network of artificial neurons and nodes meant for solving learning processor-type problems, such as artificial intelligence (AI) problems. The connections of the neuron are weighted to model excitatory or inhibitory connections and summed. An activation function defines the amplitude of the output. It is envisaged in some applications of the invention that such artificial neural networks may be used for predictive modelling and adaptive control. In some examples, these neural networks may also be trained via a dataset, such as the examples described herein. Self-learning or unsupervised learning, resulting from analysis of datasets, can occur within the network, which allows the network to derive conclusions from a seemingly unrelated information set.

Dataset

The dataset which the AI algorithms will use as a learning platform will include, but not limited to, data from patients and healthy individuals including all ages from new born and onwards. Data will consist primarily of microcirculatory images (still and moving images) obtained mainly, but not limited to, sublingual and oral microcirculation as well images from all other internal and external body and organ surfaces. These microcirculatory images are obtained from various types of vital microscopes described above. Still histological images of the microcirculation as obtained from biopsies are also to be included in the data set. Movies or images of the subjects can either be obtained at a single time point or be followed over the course of time either short time (e.g. continuous, intermittent) or over longer periods of times (such as months or years throughout life) to be used to evaluate the progress of disease or health. These images will be coupled to other variables related to demographics and clinical data regarding the health and disease state of the subject as well as medication and other therapeutic modalities the subject is receiving (included is also exercise regime coupled to microcirculatory variables). The data set will include detailed information concerning single individuals as well as databases of categories of healthy subjects as well patients suffering from particular disease states or undergoing specific therapeutic interventions.

The microcirculatory variables derived from the various MC techniques discussed can be derived using conventional analysis or derived using AI methodologies. These MC functional parameters will be then used as a learning set for AI to evaluate the various example embodiments described herein. MC functional parameters which will be used as input variables AI learning set will include but not limited to: Microcirculatory hemodynamic values: capillary, venule and arteriolar blood flow and capillary blood volume and haematocrit (see reference [11]), identification of types of vessels (e.g. capillaries, capillary loops, arterioles, venules), Proportion of perfused vessel density or functional capillary density (PVD [mm/mm2]. FCD (density of functional capillaries where flowing red blood cells (RBC) carrying oxygen are measured}; Vessel diameters (VD [µm]); RBC velocity (RBCv [µm/sec] or arbitrary units such as obtained from Laser Speckle Imaging; Leucocyte velocity (µm/sec) and number; proportion of perfused vessels (PPV [%]); Microvascular flow index; Flow heterogeneity (MFlhet (see reference [11]) or MC expressed as a function of a histogram of MC variables); Rolling and sticking leukocytes (µm/sec), number of leucocytes, microcirculatory RBC Hb saturation, capillary tube and discharge haematocrit. In some examples, the metric describing the number and/or density of functionally flowing red blood cell in a field of view may be referred to as the parameter tissue red blood cell perfusion (tRBCp), and can be calculated using MicroTools or the IVM device and is used as target value for resuscitation following a state of shock. In some examples, a microcirculatory functional parameter can be measured in steady state, but also as a result of a challenge. These challenges can identify the reserve microcirculation which can be therapeutically targeted for recruitment with the aim of improving the capacity of the tissues to extract oxygen from the capillaries due to the shorter diffusion distances. Such challenges to the microcirculation include the administration either topically or systemically of a vasodilator such as nitro glycerine or other challenges such as a metabolic challenge (a meal), blood transfusion and exercise.

Morphological parameters including but not limited to total vessel density (TVD [mm/mm2]); functional microcirculatory structures (sputum glands, orifices, vessel loops, rectal crypts, microcirculatory units related to organ function, intestinal villi, renal tubular structures, liver lobule, alveoli, glycocalyx dimensions (e.g. measured using the IVM device and/or RBC perfused boundary region as a measure of glycocalyx dimensions), tortuosity, fractal dimensions, bifurcations of MC vessels. AI identification of mean values but also of histograms of the distributions of said parameters within a population or within a single measurement of the microcirculation (field of view), or within a single capillary. In addition to these values histological parameters extracted from biopsies, spectroscopic measurements measuring tissue and plasma molecular and particular constituents as well morphometric information about the MC obtained from optical coherence tomography and confocal microscopy are included as input variables in the assessment of the MC.

In addition, MC variables extracted from such techniques such as intravital microscopy (including fluorescence and capillaroscopy), spectrophotometry, laser speckle imaging, near infrared spectroscopy, fluorescence vital microscopy (see reference [11]). Fluorescence spectroscopy can be incorporated into the IVM device to obtain spectroscopic information about plasma and tissue molecular and particle constituents. In addition, histological information concerning microcirculatory morphology can be obtained from biopsy analysis and optical coherence tomography. All MC variables extracted from these techniques either by AI or conventional methodologies can be used as input variables for the data set required for AI learning.

Other measures of organ perfusion are also used to identify microcirculatory alterations including capillary refill time, peripheral temperature, arterial venous CO2 gap, contrast enhanced ultra sound derived microcirculatory flow measures (intra-renal microcirculatory transit time, laser speckle imaging, laser Doppler flow measurements, gastric tonometry, near infrared spectroscopy. Although these measures do not image the MC, in some examples of the invention they may be used as input variables to AI analysis, providing extra information related to states of health, disease, indications for therapy and outcome.

AI analysis will also analyze the quality of the IVM device's obtained measurements during a measurement session, prior to being accepted for analysis and for being included into the data set. Clinical and health related data set: Included as part of the data set and paired with the above microcirculatory variables associated with each patient and subject are the demographics of the subjects and patients, information about the presence of co morbidities (e.g. hypertension, diabetes, heart failure, COPD, obesity, fragility, mental disease, cancer) and clinical information relating to these conditions (imaging, pathological information, clinical chemistry, functional tests, genomic analysis of genes related to states of disease) with the microcirculatory variables listed above. In conditions of intensive care, surgery or trauma where multiple parameters are monitored and known, the full range of conventional clinical parameters including, but not limited to, the measurements of hemodynamic variables, field potentials (e.g. ECG, EEG), ultrasound and other variables related to the measurement of organ function and identification of disease are included as input variables. Also, as input variables for the data set and output parameters to show AI related benefit are considered scoring systems related to health and disease. These include but are not limited to, the number of DALYs (Disability-Adjusted Life Year (DALY) a metric quantifying the burden of disease from mortality and morbidity; defined as the gap between current health status and an ideal health situation where the entire population lives to an advanced age, free of disease and disability), the APACHE score (the "Acute Physiology, Age, Chronic Health Evaluation score is a severity-of-disease classification system used in the ICU and the SOFA (Sequential Organ Failure Assessment) score also focused more on organ function. Other measures relating to organ function (e.g. renal failure see reference [18], heart failure) liver failure and brain function is included as well as biomarkers related to several disease states such as cancer, sepsis kidney disease heart failure and diabetes.

These clinical health related data set, besides being used as input for the learning set, are also used in the Embodiments outlined below as methodologies for quantifying the benefit of AI based microcirculatory analysis gives regarding advice, identifications, analysis and interventions.

Clinical and Health Related Data Set:

This section is a brief outline of the type of input parameters which can be given to an IVM device in support clinical decision making procedures. Physical examination is a corner stone of input variables for clinical decision making and is well described in the medical literature (age, blood pressure, BMI, co-morbidities, sex, lacatate and acid base disorder and arterial venous CO2 gap, etc.). Measurements made in association with such examinations include blood chemistry analysis where among other variables indicators of organ function in terms of biomarkers are assessed (e.g., liver, kidney and heart function), humoral, metabolic immunological and electrolyte biochemical variables as well as haematological variables (blood gas, blood components, haemostasis, immunological variables) can be assessed as and used as input parameter. Similar measurements can be made in the analysis of urine and faeces. Besides such measurements invasive measurements can provide a range of hemodynamic variables related to the function of the cardiovascular system (blood gas, heart function, blood pressure, blood flow). Field potentials can give important information regarding organ function and include ECG, EEG and EMG. Imaging modalities used in clinical medicine include angiograms, MRI, CT and echo scans. Further information can be obtained by histological examination of biopsy material as well by endoscopic examination. Included here is also genetic information obtained by gene sequencing. Besides these specific indicators of health and disease clinical scores such as are also considered as input data set including but not limited to the Frailty Index For Elders (FIFE), Paediatric Risk of Mortality (PRISM) score and the Glasgow coma scale (GCS) and such compiled indicator scores relating to the health and severity of disease in patients.

Importance of the Microcirculation

The microcirculation refers to that part of the cardiovascular system that embodies the smallest vessels of the body, which vascularizes the tissue cells of the various organ systems. Its main function is to transport oxygen carrying red blood cells and nutrients to the tissue cells to support their respiratory needs. In addition, it is the interface between circulating blood and tissues cells where immunological and humoral actions occurs. The microcirculation contains blood vessels with flowing blood cells in plasma with vascular diameters less than 100 µm. Blood flows from arterioles (emanating from the arteries and surrounded by smooth muscle cells able to modulate vascular tone and thereby blood flow through the microcirculation), to capillaries (the smallest vessels in the microcirculation where red and white blood cells flow in single file and red blood cells release their oxygen to the surrounding tissue (parenchymal) cells) which then enter the venules (these collecting vessels eventually connect to the veins). The arterioles, capillaries and venules, their flowing cells including the fluid in which they are in (plasma) and the tissue cells surrounding the blood vessels (endothelial cells, smooth muscle cells and neighbouring parenchymal cells) are collectively referred to as the microcirculation. Their physical diameters, density, morphology and function (e.g. flow of red and white blood cells) are closely related to the state of health of the individual. Abnormal structures and/or abnormal flow kinetics identify in advance of alterations of other hemodynamic variables impending adverse health and form an early identification of outcome (see references [11]). Vascular re-modelling and microcirculatory alterations occurs as a result of chronic disease states (e.g. diabetes, cancer, hypertension, sepsis, cardiovascular compromise, heart and kidney failure, arteriosclerosis, intestinal ischemia, venous insufficiency, pre-eclampsia, small and large vessel disease, eye disease, Alzheimer's) affecting morphology and blood flow kinetics often as a result of a vascular or metabolic challenge as well acute disease states such as stroke, surgery, myocardial infarction, cardiac arrest, trauma and states of shock (see reference [11]). Some examples of the invention described herein propose relating abnormal variables related to the blood flow kinetics and morphology of the microcirculation to other physiological properties of individuals and analyzing these using AI and assessing and identifying health and disease advising on therapy and identifying their outcome.

The term microcirculatory abnormalities or alterations refer to changes in the parameters with respect to their values in normal healthy individuals and signal a presence of disease. These alterations have been described in reference [10] and [11]. In these references a differentiation of microcirculatory abnormalities have been distinguished into four types of abnormalities:

Type 1; Heterogeneous RBC flow caused by RBC and endothelial cell injury induced for example by sepsis or tropical diseases (malaria, dengue) results in RBC stagnant capillaries next to perfused capillaries resulting in microcirculatory shunts and a reduction of tissue oxygen extraction capacity.

Type 2: A reduction in the functional capillary density of the MC which can be caused by a dilution of the blood induced by excessive administration of fluids resulting in hemodilution induced anaemia or anaemia due to other causes.

Type 3; A stasis in the RBC flow can be caused by increased vascular resistance and/or elevated venous pressure due such conditions as hypertension, pulmonary hypertension, a tamponade (obstructive shock), excessive administration of fluids or vasopressors agents.

Type 4: abnormality where there is an increase in distance between the vessels and an increase in the focal depth can be cause results in an increased oxygen diffusion distances due to oedema caused by capillary leak syndrome caused by burns, tropical disease.

Examples of therapies based on these observations of MC abnormalities include, for Type 1 abnormality; antibiotics, anti-inflammatories, blood transfusions, fluid therapy; for Type 2 abnormality: a reduction in the type or amount of fluid being administered, the administration of blood or RBC enhancing therapy (iron or EPO); for Type 3 abnormality: a reduction in the vasopressor agent, administration of a vasodilatory agent, treatment of a tamponade by relieving an obstruction; for Type 4 abnormality: a resolution of the capillary leak removal of excessive fluid by diuretic therapy and or haemodialysis.

Other main types of microcirculatory abnormalities consist of a slowing of the velocity of blood cells. This defect is associated with either a failing heart (heart failure) or the presence of insufficient volume (hypovolemic shock). Associated therapies can be, respectively, the administration of volume (fluids or blood) or of cardiotonics in support of heart contractility (such as inotropics) or for the attachment of a left ventricular assist device. Second type of abnormality consists of a decrease in functional vascular density. Such a condition can be associated with a disease state where vasodilator therapy is indicated or blood transfusion.

The presence of an abnormal kinetics of leucocytes, such as leucocyte count be up, or leucocyte rolling and sticking are observed are associated with the presence of inflammation and or haematological disorder. Appropriate therapies which are indicated include chemo/radio therapy, blood transfusions and anti-inflammatory drugs. In extension of this it will also be possible to identify using a suitable NM modality to identify pathogens in the MC such as the presence of microorganism such as bacteria, viruses, fungi and parasites underlying disease states.

The IVM device described herein may be trained by an appropriate learning set including a multitude of clinical and microcirculatory parameters mentioned in our patent, will provide a much more sensitive and specific methodology to identify specific states of disease and advice specific therapeutic strategies, which will improve outcome much more readily than available diagnostic strategies.

Since the 1990s hand-held vital microscopes (HVM) have been introduced for the clinical observation of the microcirculation with the aim of obtaining information about this important physiological compartment during various health and disease states, and therapeutic interventions. Abnormalities in microcirculatory blood flow and morphological alterations as well as the success or failure of therapy have been reported. These abnormalities have been classified into different categories of alterations and these have been linked to various disease states and have been shown to be more sensitive than conventional indices of disease indicating that analysis of microcirculatory alterations can be used to gain information about health and disease with more sensitivity and specificity than conventional parameters and opening the way to perform differential diagnosis (see reference [11]).

How to Measure the Microcirculation

Examples of the invention described herein discuss the measurement of the microcirculation (MC) and its cellular constituents, for example at a patient's bedside and describe the methodologies that can be used. The microcirculation can be measured in several ways in humans. The methodology to directly observe the microcirculation with its flowing blood cells, and capillary venules and arterioles as well as their cellular (red blood cells, leucocytes, parenchymal cells (including endothelial cells, and tissue cells such as squamous cells, renal tubular cells), hepatocytes as well as sub-cellular structure (e.g. glycocalyx, platelets, microparticles, circulating tumour cells, cell membranes, mitochondria, cell junctions, nucleus can be accomplished by intelligent vital microscopy (IVM). Conventional intra-vital microscopy using visible or fluorescent light, as well as images obtained by endoscopy, can also be used for this purpose allowing visualization and quantification of these MC structures as well as physiological and physical variables. HVM encompasses orthogonal spectral imaging (OPS), side stream dark field (SDF) and incident dark field (IDF) imaging or a combination of these techniques often light of specific wavelengths but also white light embodied in a hand-held (or intra-vital) microscope as optical contrast for specific features of the MC and described in detail elsewhere (see reference [11]).

Visible light can be used but also fluorescent imaging as a consequence of in vivo labelling of cells using in vivo methodologies (e.g. Na-fluorescein, indocyanine green and other fluorophores which can adhere to cells, plasma or particles allowing detection by fluorescence spectroscopy). Other techniques for monitoring the microcirculation include Laser Speckle Imaging and Laser Doppler Imaging which are also covered in this document when referring to the measurement of the MC.

Different functional tissue variables related to the MC can be measured using different wave length of light. The most obvious one in this respect is the use of different wavelengths of light to measure the oxygen saturation of Hb in the flowing red blood cells. Different wavelengths of light can also be used to identify the presence of leucocytes.

Information regarding the functional and anatomical properties of the MC structures are used as input variables to AI algorithms to relate them to health, disease and response to therapy. Currently MC images can be analyzed and functional variables extricated from images of moving cells in the MC by analysis of moving cells in the images using advanced image processing methodology. Several software methodologies have been introduced to analyze microcirculatory images in this manner (see references [2], [3], [4], [12]) but as yet no one has used AI to analyze such MC images. A proof of concept study is demonstrated herein wherein the application of AI methodology for the analysis and classification (the presence of vasodilation or not) of microcirculatory images are comprehensively presented. Currently such analysis is carried out by manual or semi-quantitative analysis having no intelligence and requiring much time and having no aspect of self-learning or AI (see references [7], [13]).

Examples herein described disclose in sufficient detail, the method and system for analysis of MC variables as input learning for development of an IVM device in combination with other markers of health and disease to identify the state of health and response to therapy.

In some embodiments the AI based analysis method described here is used to identify disease states and indicators of health previously not known by analysis of (micro) vascular morphology and function in combination with other physiological medical or clinical parameters. In other embodiments such functional parameters can be obtained by different techniques including invasive and non-invasive monitoring using echo, (f)mri and endoscopy, hemodynamic and biochemical biomarkers (blood chemistry, biomarkers related to the function of various organ systems) as well as analysis of gene sequence analysis related to the evaluation of health and disease. Hemodynamic parameters included can be such variables as systolic, mean and diastolic blood pressure (BP); stroke volume; cardiac output; lung water, total peripheral resistance (TPR); whole blood viscosity (BV); plasma viscosity; haematocrit; RBC aggregation and deformability; blood chemistry levels including but not limited to haemoglobin (Hb), electrolytes, lactate, glucose, insulin, albumin, biomarkers of organ dysfunction (e.g. creatinine, troponin, NGAL, etc.), leucocyte and platelet count. Similar analyses are made of other bodily fluids such as urine, sweat, tears, sputum, ascites and Broncho-alveolar lavage fluids.

In some example embodiments, the learning sets for the establishment of AI network can be obtained by analysis of databases of populations of humans in health and disease where microcirculatory measurements ("Datasets") are included. Said Datasets can be generated from populations of patients being supported by various therapeutic modalities including but not limited to exercise and extracorporeal organ support (ECOS) devices (including ECMO (extracorporeal membrane oxygenation), LVAD (left ventricular assist devices), mechanical ventilation, haemodialysis and cardiopulmonary bypass devices). In particular environments where AI methods disclosed herein are used to optimize these ECOS devices in a feedback servo type of setting controlling ECOS settings with MC as a target for optimizing settings. In other embodiments the learning sets for AI are obtained by the continuous evaluation of physiological multi parameters of a single patient and/or individual.

In the above described environments the example IVM device and method of analysis described herein of the microcirculation is performed in a point-of-care setting for personalized medicine continuously evolving in time and/or in response to therapy in the short term but also in the long term over years. The example IVM device and method described herein are also used to analyze the epidemiology of large data sets of information where microcirculation analysis forms a part of the data sets to evaluate the evolution of health and disease.

Functional Parameters of the MC that can be Distilled by AI Analysis of the MC

There are various functional parameters which can be measured which relate and identify acute as well as chronic states of health and disease. Kinetic information relating to the hemodynamic of the microcirculation includes the velocity profile of the various blood cells, but also includes the sticking and rolling of leucocytes as they interact with the endothelial cells as a consequence of inflammation. The IVM device will identify states of inflammation and infection related to disease by analysis of red and white blood flow kinetics. Not all blood vessels of the MC are filled with red blood cells carrying oxygen at rest (about 30% unfilled capillaries). They remain invisible to the IVM device according to examples of the invention, because there are no Hb filled RBCs needed for IVM detection. These as yet unfilled vessels constitute the physiological reserve of the MC which can be recruited during stress or exercise. These recruitable vessels can be identified by use of fluorophore labelled platelets which pass into these capillaries (either flowing or stagnant plasma). Their presence can also be identified by giving a challenge by topical application of a vasodilatory compound (e.g. nitro-glycerine, lidocaine or acetylcholine) which then opens all the vessels allowing evaluation of the maximal available functional vessels, which can be functionally recruited for enhancing oxygen availability during states of stress or disease. These manoeuvres allow the quantification of the maximum recruit able vessels in the microcirculation. This quantity is important to determine since if resuscitation manoeuvres results in the maximum filling of vessels then further resuscitation is futile since no more vessels can be recruited and a maximum oxygen transport capacity has at that moment been established.

Knowledge of this recruitability parameter also defines a target for achieving optimal resuscitation This condition could be important for AI to determine at the bedside since over use of medication such as fluids and vasopressors in so-called unresponsive patients is a serious problem resulting in increased morbidity and an AI analysis of the microcirculation applied at the bedside would prevent such over medication. The herein described examples of an IVM device and method therefor thus provide an important diagnostic target for a point-of-care methodology in emergency and critical care medicine where currently resuscitation targets are wanting.

The herein described examples of an IVM device and method therefor also provide an important diagnostic target for a point-of-care methodology in emergency and critical care medicine where currently resuscitation targets are wanting.

Microcirculatory parameters involving metrics of convection (red blood cell flow, tube and discharge haematocrit) and diffusion (TVD, functional capillary density) are parameters related to the oxygen transport capacity function of the microcirculation. These kinetic parameters are determined either at steady state or as a result of a challenge or therapeutic intervention. Evaluation of morphometric parameters such as tortuosity, fractal dimension, number of bifurcations, presence of twisting structures allows identification various forms of chronic condition, such as cardiovascular disease e.g. hypertension, diabetes and cancer. Such input variables can be obtained by the techniques described above. Integrative evaluation of the above microcirculatory values in addition to other physiological parameters related to health, disease and therapy will increase the sensitivity of the AI analysis of MC parameters to identify severity of disease and response to therapy and be used as a health metric and which can be followed and evaluated over years in combination with other indicators of health and physiology. Their integrative evaluation will provide a medical finger print as to the state of health of an individual. Some examples of the invention described herein propose a use of AI applied to microcirculatory values with and without other conventional clinical parameters to identify the state of health, disease and efficacy of therapy in various clinical settings as well as in the setting of personal health care (e.g. coupled to a mobile phone).

Microcirculation as an Indicator of Health.

It is known that the functional state of sublingual microcirculation (density of functional capillaries, flow, red and white blood cell kinetics) and reactivity (the change in microvascular properties as a result of a challenge which can be in the form of a pharmacological challenge (e.g. nitroglycerine) or a functional challenge (e.g. exercise, a meal, therapy) is related to the ability of a person to perform tasks as well as being associated with disease as well as being a marker of frailty in the elderly or in healthy individuals wanting to undertake extreme tasks (mountain climbing, jet pilot, combat). In some examples of the invention described herein, a mapping of the microvascular structures intraorally (e.g. sublingually, in the cheeks, inside of the lip, in skin as well as MC structures in other parts of the body to be analyzed by AI) may be expected and provide a finger print of (cardio)vascular health for either personal or medical or clinical use.

Example of the Application of a Learning Processor Algorithm to the Analysis of the Microcirculation:

The aim of this example is to provide a proof-of-concept for the application of a deep learning processor algorithm to identify interventions or disease states from intelligent vital microscopy, IVM, device image sequences recorded of the human sublingual microcirculation.

This example provides an application of an AI algorithm as described in FIG. 4 and FIG. 5A and FIG. 5B to the analysis of the microcirculation in a two-dimensional convolutional neuronal network as a system and a method for detection of whether there is local microcirculatory vasodilation.

FIG. 4 illustrates an example of a neuronal network flow diagram for an intelligent vital microscopy, IVM, device using AI, in accordance with example embodiments of the invention. In the neuronal network flow diagram 400, the image sequences of the microcirculation and clinical data are acquired and input 410 from an output of the IVM device camera (such as camera 250 of IVM device 200 of FIG. 2), and are then pre-processed by cropping 401 and stabilization of movements 402 in the images and are then assessed to allocate a quality grade of the pre-processed images 403. A decision is made at 404 as to whether (or not) the quality of the graded, pre-processed images at 403 is acceptable. If the quality of the graded, pre-processed images at 403 is not acceptable, the user may be advised to make a new recording (such a decision can also be made on an AI platform) and the neuronal network flow diagram 400 loops back to the start with new image sequences of the microcirculation and clinical data being acquired and input 410.

However, if the quality of the graded, pre-processed images at 403 is not acceptable, as determined at 404, then further processing of the images is performed and further time points can be collected during the course of a clinical intervention, thereby allowing a sequential assessment of the changes in the MC to be evaluated 405. In some examples, the evaluation at 405 may entail repeated analysis after clinical intervention, e.g. a local vasodilatory challenge, a volume challenge, a vasoactive drug inotrope, etc. These analysed image sequences are then collected ready for processing at 406 as part of an inference or training data set of an AI algorithm at 409. Parallel to the acquisition of sequence of images, clinical or other data related to the health or disease of the patient may be acquired and attached to each image sequence at 407, 408.

Referring now to FIG. 5A, an example flow chart 500 of a neuronal network for training and inference for classification (identification of features, e.g. disease states) or quantification (of relevant physiological microcirculatory parameters (RPMP)) of intelligent vital microscopy, IVM, device image sequences of the microcirculation and clinical data in a supervised leaning model is illustrated.

The process starts with the input for neural network training 501, obtained for example from the output of FIG. 4 (for example step 409). In one example, these can include inputs for model training, originating from different patient categories: IVM image sequences of the microcirculation, and/or clinical data at 506. In one example, the endpoint input data for supervised model training may additionally or alternatively consist of categorical (with n categories), or continuous endpoint data 507. In some examples, the input for neuronal network inference and identifications 501 may also originate from different patient categories 502, for example including, but not limited to, IVM image sequences of the microcirculation, and clinical data 508.

This input 508 or that of 506 can form as input to a Data analytics circuit or process 503, where image sequence pre-processing (example workflow) can occur. In this manner, the image sequence pre-processing may take the form of image acquisition and pre-processing circuit 221 of FIG. 2, for example consisting of pre-processing 509, cropping (e.g. to a largest common frame size) 510, frame processing (e.g. to a mean image, as well as calculation, algorithmic feature extraction and/or contrasting) 511 and scaling 512 operations, resulting in a pre-processing output 513 that forms the training 514 or validation 515 data set.

It is envisaged that for some example applications, tools 523 that can be used for data analytics may include but not restricted to are Pandas™, Spark™, Graph™ and Microtools™' own developed data analytics software (see reference [7]). In some examples, it is envisaged that the output of data analytics process 503 may also be used as a testing data set 522, which can serve as an input to a neural network training for specific purposes 524. The input for the training of two-dimensional convolutional neural network (example configuration) where tools such as TensorFlow can be used 504 include the training dataset 514 and data validation dataset 515, set as well as categorical or continuous endpoint data 507.

It is envisaged that for some example applications, the training network process 504 may consist of different dimensional matrices 516, 517, which can serve as input layers 518 to a series of convolution, activation, normalization and/or pooling layers 519, resulting in output layer 520, which together are used in a series of repeated, iterative, training cycles 521.

The result of this training network process 504 may then be used as an input to the inference circuit or process 505, which consists of a trained neuronal network designed for processing specific tasks 524. For example, the trained neuronal network designed for processing specific tasks 524 may be used for inference and identifications, originating from different patient categories, including but not limited to IVM image sequences of the microcirculation, and clinical data 508 processed as a testing data set 522. The inference circuit or process 505 can include classification of disease states 525, quantification of relevant physiological microcirculatory parameters (RPMP) 526 or (but not limited to) quality assessment and identification of features related to image quality 527. It is envisaged that the output of the inference circuit or process 505 may also be used for identification of category or quantity based on input data of the microcirculation, and clinical data from a new data set 528.

In some examples of the invention, it is envisaged that by training a two-dimensional convolutional neuronal network with IVM image sequences of healthy volunteers, recorded either before or after local vasodilation, using topical application of nitro-glycerine, the fitted model is then able to identify vasodilation status of the human sublingual microcirculation.

In FIG. 5B an example flow chart 555 of a neuronal network block diagram for unsupervised training and inference for classification (identification of features, e.g. disease states) of intelligent vital microscopy, IVM, device image sequences of the microcirculation and clinical data is shown.

The process starts with the input for neural network training 551, obtained for example from the output of FIG. 4 (for example step 409). In one example, these can include inputs for model training, originating from different patient categories: IVM image sequences of the microcirculation, and/or clinical data at 556. In some examples, the input for neuronal network inference and identifications 551 may also originate from different patient categories 552, for example including, but not limited to, IVM image sequences of the microcirculation, and clinical data 558.

This input 558 or that of 556 can form as input to a Data analytics circuit or process 553, where image sequence pre-processing (example workflow) can occur. In this manner, the image sequence pre-processing may take the form of image acquisition and pre-processing circuit 221 of FIG. 2, for example consisting of pre-processing 559, cropping (e.g. to a largest common frame size) 560, frame processing (e.g. to a mean image, as well as calculation, algorithmic feature extraction and/or contrasting) 561 and scaling 562 operations, resulting in a pre-processing output 563 that forms the training 564 or a training output of categories formed in unsupervised learning and prediction category 565 based on input data of the MC and clinical data.

It is envisaged that for some example applications, tools 573 that can be used for data analytics may include but not restricted to are Pandas™, Spark™, Graph™ and Microtools™' own developed data analytics software (see reference [7]). In some examples, it is envisaged that the output of data analytics process 553 may also be used as a testing data set 572, which can serve as an input to a neural network training for specific purposes 574. The input for the training of two-dimensional convolutional neuronal network (example configuration) where tools such as TensorFlow can be used 554 include the training dataset 564 and data validation dataset 565, set as well as categorical or continuous endpoint data 557.

It is envisaged that for some example applications, the training network process 554 may consist of different dimensional matrices 566, which can serve as input layers 568 to a series of convolution, activation, normalization and/or pooling layers 569, resulting in output layer 570, which together are used in a series of repeated, iterative, training cycles 571.

The result of this training network process 554 may then be used as an input to the inference circuit or process 555, which consists of a trained neuronal network designed for processing specific tasks 574. For example, the trained neuronal network designed for processing specific tasks 574 may be used for inference and identifications, originating from different patient categories, including but not limited to IVM image sequences of the microcirculation, and clinical data 558 processed as a testing data set 572. The inference circuit or process 555 can include classification of disease states 575, quantification of relevant physiological microcirculatory parameters (RPMP) 576 or (but not limited to) quality assessment and identification of features related to image quality 577. It is envisaged that the output of the inference circuit or process 555 may also be used for identification of category based on input data of the microcirculation, and clinical data from a new data set 578.

In some examples of the invention, it is envisaged that by training a two-dimensional convolutional neuronal network with IVM image sequences of healthy volunteers, recorded either before or after local vasodilation, using topical application of nitro-glycerine, the fitted model is then able to identify vasodilation status of the human sublingual microcirculation.

Referring now to FIG. 6 an example of a training and validation of a two-dimensional convolutional neuronal network for identifying of microcirculatory vasodilation is illustrated, in accordance with some example embodiments of the invention. In particular, FIG. 6 Illustrates the results 600 of an example of the training 620 and validation 630 of a two dimensional convolutional neuronal network for identifying whether (or not) in a MC data set microcirculatory vasodilation has occurred. Images were obtained from volunteers before and after a challenge with a vasodilator. Part of the data set was used for training 620 and part for inference. Results and methods are discussed in more detail in the text below relating to a description of the worked example of how IVM (for example where the AI may be performed off-line) obtained microcirculatory image sequences can be AI analyzed and the ability of the AI methodology to accurately identify changes in microcirculatory variables associated with vasodilation validated with receiver operating characteristics of the identification in FIG. 7.

Study Design and Dataset

In 40 healthy human volunteers (age 45.8±1.9 years, 22/41(54%) male, weight 69.0±1.8 kg, height 174±1 cm, BMI 23.1±0.8 kg m−2), 103 IVM image sequences of the sublingual microcirculation were obtained. Multiple examinations were performed at baseline (n=53) and 30 seconds after topical application of nitro-glycerine solution to the sublingual area in order to induce MC vasodilation (n=50). 5 µg of nitro-glycerine (2.2·10-2 µmol of nitro-glycerine as 0.05 ml of 1% (4.4·10-2 M) nitro-glycerine solution (Perlinganit isotonic infusion solution, UBC Pharma, Bulle, Switzerland) diluted 1:102 with 0.9% sodium chloride) were applied to the sublingual area. This intervention has previously been demonstrated as intended to consistently vasodilate the local microcirculation but not the systemic circulation. The study was conducted with permission from the institutional Ethics Board of the University of Bern (KEK 226/12, ClinicalTrials.gov identifier NCT01953198) and after obtaining informed consent preoperatively from each volunteer. The IVM image sequences were then analyzed according to international consensus on examination of the sublingual microcirculation see reference [11], measuring capillary total vessel density (TVD), functional capillary density (FCD), proportion of perfused vessels (PPV) and red blood cell velocity (RBCv). At the same time, the images sequences were used to train a two-dimensional convolutional neuronal network with the intention to discern image sequences recoded at baseline versus those recorded after topical application of nitro-glycerine.

Analysis of the Microscopy Image Sequences According to Current Standard

The IVM image sequences were recorded and stabilized using the CCtools 1.7.12 software (Braedius Medical, Huizen, The Netherlands) associated with the IDF imaging IVM device 175 shown in FIG. 1 (Cytocam, Braedius Medical). Thereafter, they were analyzed using an advanced computer vision algorithm called MicroTools version 63, which was specifically developed for analysis of the sublingual microcirculation. One example of an algorithm and software are described elsewhere (see reference [7]).

Application of Deep Learning Techniques to the Microscopy Image Sequences

Computing Environment and Structure of the Neural Network

The neuronal network used in this study was developed and applied using the R environment for statistical computing, version 3.5.1 (see reference [14]) with the Keras package version 2.2.0 and the TensorFlow package version 1.9 (see reference [15]). A fully scripted and reproducible data management pathway was created for pre-processing of training 620, validation 630 and testing data and for training and application of the neuronal network. The neuronal network consists of sequential blocks of two-dimensional convolution using rectifier linear units (RELU) for activation, batch normalization and two-dimensional maximum pooling. The first two-dimensional convolution layer serves as input layer. The output layer is a dense layer utilizing a SoftMax activation function for categorical output. See Table 1 for a detailed description of the neuronal network.

Pre-Processing of the Datasets for Neural Network Application

IVM image sequences stabilized by CCtools contain moving black borders whose size corresponds to the translation vector used for image stabilization. In the first step of dataset pre-processing, the maximum size of these stabilization artefacts was detected on each border of the image and the frames cropped by that amount. Thereafter, cropping of the right and lower border to the maximum common frame size across all image sequences was performed, resulting in equally-sized frames of maximized size with respect to the amount of necessary stabilization within the dataset, Thereafter, a mean image was created out of all frames within an IVM image sequence, containing the mean grey scale values of the corresponding pixels across all frames. The mean images were then scaled to a width of 100 pixels to generate the input matrix for the neural network.

The entire dataset was randomly sampled for a subset consisting of 90% of the data points, with weighting applied for vasodilation status. The resulting subset was used as the training and validation dataset, whereas during fitting of the neuronal network model, a randomly sampled 20% subset of the training dataset was used for continual validation. The remaining 10% of the original dataset was used for testing of the neuronal network model after completion of fitting.

Statistical Analysis

Referring now to FIG. 7, a graphical identification example 700 of microcirculatory vasodilation using standard analysis of intravital microscopy image sequences is illustrated, in accordance with some example embodiments of the invention Predictions made by the neuronal network of the vasodilation state of the sublingual microcirculation were assessed using their true-positive rate 750 in a testing dataset (versus a false positive rate 760) that is entirely separate from the training and validation datasets. The predictive value of the vasodilation state of the sublingual microcirculation according to parameters such as TVD 740, FCD 710, PPV 720 and RBCv 730 was examined using receiver operating characteristics analysis and calculation of the area under the curve across the entire dataset. For all statistical analyses a fully scripted and reproducible data management pathway was created within the R environment for statistical computing, version 3.5.1. Receiver operating characteristics analysis was performed using the R library plotROC version 2.2.1 [16]. Graphical output was generated using the R library ggplot2, version 2.2.1, see reference [17] as shown in FIG. 6.

Results of this Example

The dataset contained $28.9 \times 10^9$ pixels of image data, which were pre-processed as described above, yielding a $93 \times 100 \times 80 \times 1$ matrix that was used to train and validate the neuronal network. During 150 epochs of training, a steady decrease in loss (as illustrated at 615 of the loss graph 610 of FIG. 6) and an increase in accuracy (as illustrated at 655 of the accuracy graph 650 of FIG. 6) were observed, without occurrence of overfitting according to validation.

Applied to the testing dataset, an accuracy of 80% for identification of vasodilation status was revealed for the fitted model.

Thus, the graphs 600 of FIG. 6 illustrate the results of an example of the training 620 and validation 630 of a two dimensional convolutional neuronal network for identification of microcirculatory vasodilation. Images were obtained from volunteers before and after a challenge with a vasodilator. Part of the data set was used for training and part for inference. Results and methods are discussed in more detail in the text below relating to a description of the worked example of how IVM obtained microcirculatory image sequences can be AI analyzed.

Receiver operating characteristics analysis for identification of vasodilation status by current standard parameters for microcirculatory analysis yielded an area under the curve of 0.8 for TVD, 0.8 for FCD, 0.5 for PPV and 0.7 for RBCv (FIG. 4 400).

The graphical example 700 of on-site inference on a trained neuronal network for a specific purpose FIG. 7 illustrates receiver operating characteristics AI analysis for identification of vasodilation status by current standard parameters for microcirculatory analysis. As can be seen from the area under the curve an excellent identification of physiological microcirculatory parameters of 0.8 for TVD (total vessel density), 0.8 for FCD (functional capillary density), 0.5 for PPV and 0.7 for RBCvel was obtained By training a two-dimensional neuronal network with IVM image sequences obtained before and after vasodilation of the sublingual microcirculation, a model is fitted that allows for identification of maximal vasodilation of the microcirculation versus healthy volunteers in IVM image sequences of the sublingual microcirculation, or indeed, in some examples of the invention, the model may be compared with identified diseased volunteers/humans. In this way, examples of the present invention propose a generic learning processor algorithm that achieves a similar result as did a complex algorithm that was specifically designed to analyze the sublingual microcirculation.

Referring now to FIG. 8, an example flowchart 800 or system diagram of on-site inference on a trained neuronal network for a specific purpose (e.g., identification of disease patterns in an IVM device of the microcirculation and clinical data, AI conversational search, and data collection for continuing training of neuronal networks in remote locations is illustrated, in accordance with some example embodiments of the invention. In particular, the example flowchart 800 Illustrates a flow process of an AI circuit (such as learning processor 222 of the IVM device 200 of FIG. 2) embedded as part of (but not limited to) an IVM device for imaging and analyzing AI aided MC features. The flowchart 800 or system diagram of on-site inference is shown on a trained neuronal network for a specific purpose (e.g., identification of disease patterns in intelligent vital microscopy, IVM, device images of the microcirculation and clinical and/or health related data of a specific patient or volunteer).

The flow process of AI embedded in the IVM devices for on-site inference on trained models is shown in 801. In this circuit or process flow, on-site data acquisition of the microcirculation and clinical data in human subjects/patients (IVM image sequences and accompanying clinical and health related data) is accomplished at 803, and as shown in FIG. 4. Following this step, on site data pre-processing and merging can occur at 804, and as shown in FIG. 5. Then, on-site inference on a copy of a trained neuronal network (which can be periodically updated) for a specific purpose (e.g., identification of disease patterns) is performed at 805. This modality can then provide on-site real-time feedback on such features as: quality, classifications of microcirculatory parameters, microcirculatory alterations, disease states; providing advice on: subsequent measurements needed and/ or interventions for further evaluation and/or therapy; and/or prognosis of patients and/or exercise training regime, as shown at 806.

Optionally (as illustrated by the dashed line) the output of this embedded IVM device can communicate with a remote person (i.e. medical specialist) or an operating modality (i.e. the cloud) for downloading relevant information or engaging in a conversation or for training, as at 802. Data can in this way be added, as shown at 807, to a large secure remote database of microcirculatory and clinical data at 808. Therefore, in some examples, this may make the training set even more complete, as illustrated at 809. In this example, the updated trained AI network for on-site deployment at 810 can then be download to the on site IVM device 811. A more comprehensive description of such a modality is shown in FIG. 9.

FIG. 9 Illustrates an example of a flow process 900 of an AI system for inference on a remote, cloud-based neuronal network for a specific purpose (e.g., identification of disease patterns in intelligent vital microscopy, IVM, device images of the microcirculation and clinical data); AI conversational search; and data collection for continuing training of neuronal networks in remote location. On-site AI embedded IVM device for inference on remote trained models and/or AI conversational search and/or backup offline functionality via an inference on an on-site trained model is shown in flow process or circuit 901. The flow process or circuit 901 consists of a data acquisition of the microcirculation and clinical data processing at 904, and as described in FIG. 4, followed by data pre-processing and merging at 905 and as described in FIG. 5. In some examples, this functionality may then be followed by an offline functionality for on-site inference on a copy of a trained neuronal network for a specific purpose at 907, thereby providing real time feedback on quality of recording and advice on how to improve, classifications of microcirculatory parameters, microcirculatory alterations, disease states; and providing advice on: subsequent measurements needed and/or interventions for further evaluation and/or therapy; and/or prognosis of patients and/or exercise training regimes, as illustrated at 908.

Subsequently in some examples, it is envisaged that secure contacts at 909, 910, 911 may be made from the onsite IVM device 906 to a Cloud connection 902, thereby enabling database improvement 911 and/or AI conversational search 906.

The cloud connection 902 (example) can then interact with a remote database 903 for continuing AI training 912 (as shown in FIG. 5) and/or AI conversational search. In this manner, it is envisaged that new data can be added to the central database 912 augmenting the larger MC and clinical data in a database 913 in a remote location. In this manner, further continued training of the neuronal network at 914 and/or the trained AI framework for on-site deployment at 917 can be performed. These then can be transferred to the on-site device at 916, 918. This functionality will also allow AI conversational search queries to be made 915.

Referring now to FIG. 10, an example of a neural network 1000 that may be employed as a learning processor, such as an artificial intelligence (AD-based architecture to analyze the function and morphology of microcirculation is illustrated according to some examples of the present invention. In some examples, the example neural network 1000 may comprise a convolutional neural network 1000, which applies a series of node mappings 1080 to an input 1010, which ultimately resolves into an output 1030 consisting of one or more values; from which at least one of the values is used by the a neural network 1000, for example the AI-based architecture of FIG. 2. The example convolutional neural network 1000 comprises a consecutive sequence of network layers (e.g. layers 1040), each of which consists of a series of channels 1050. The channels are further divided into input elements 1060. In this example, each input element 1060 may store a single value. Some (or all) input elements 1060 in an earlier layer are connected to the elements in a later layer by node mappings 1080, each with an associated weight. The collection of weights in the node mappings 1080, together, form the neural network model parameters 1047. For each node mapping 1080, the elements in the earlier layer are referred to as input elements 1060 and the elements in the output layer are referred to as the output elements 1070. An element may be an input element to more than one node mapping, but an element is only ever the output of one node mapping function 1020.

In order to calculate the output 1030 of the convolutional neural network 1000 the system first considers the input layer as the earlier layer. The layer(s) to which the earlier layer is connected by a node mapping function 1020 are considered in turn as the later layer. The value for each element in later layers is calculated using the node mapping function 1020 in equation [1], where the values in the input elements 1060 are multiplied by their associated weight in the node mapping function 1020 and summed together.

Node mapping function 1020: $d=$
$$A(w_{ad} \times a + w_{bd} \times b + w_{cd} \times c) \quad [1]$$

The result of the summing operation is transformed by an activation function. 'A' and stored in the output element 1070. The convolutional neural network 1000 now treats the previously considered later layer(s) as the earlier layer, and the layers to which they are connected as the later layers. In this manner the convolutional neural network 1000 proceeds from the input layer 1040 until the value(s) in the output 1030 have been computed.

In examples of the invention, the convolutional neural network 1000 may be trained. In some examples of the invention, the training of the convolutional neural network 1000 may entail repeatedly presenting medical data as the input 1010 of the convolutional neural network 1000, in order to analyze the function and morphology of microcirculation. In some examples of the invention, an optimisation algorithm may be used to reduce a loss function, for example by measuring how much each node mapping 1080 weight contributed to the loss, and using this to modify the node mapping functions 1020 in such a way as to reduce the loss. Each such modification is referred to as an iteration. After a sufficient number of iterations the convolutional neural network 1000 can be used to analyze the function and morphology of microcirculation from an input of medical data.

In some examples of the invention, the large number of model parameters 1047 used in the convolutional neural network may require the device to include a memory 1090. The memory 1090 may be used to store the training data 1015, the model parameters 1047, and any intermediate results 1093 of the node mappings.

Thus; in the IVM device input data (a training dataset, clinical dataset; model parameters or intermediate results) is fed to the learning processor neuronal network in a format that fits the input matrix. Nodes are mapped in a specific way that is adapted to the purpose of the device (forming e.g. a convolutional neuronal network). The information is gradually reduced through a series of interconnected input/output elements to generate the final output The Following Embodiments Demonstrate Additional Aspects of the Disclosed Subject Matter A first embodiment is the method wherein IVM analysis of the MC and quantification of morphological and functional parameters of the microcirculation and changes therein over time is used to evaluate health, disease and in response to therapy. The input variable parameters in this AI analysis include but not limited to movie clips and images of the MC and derived parameters including visual inspection obtained by IVM and variables using other MC techniques described in the Date Set section of all organ surfaces including but not limited to the sublingual and oral region. Examples of the Input variable parameters include but are not limited functional parameters of the MC including: Microcirculatory hemodynamic values: capillary, venule and arteriolar blood flow and blood volume, identification of types of vessels (e.g. capillaries, capillary loops, arterioles, venules), Proportion of perfused vessel density or functional capillary density (PVD [mm/mm2]. FCD (density of functional capillaries where flowing red blood cells (RBC) carrying oxygen are measured); Vessel diameters (VD

[μm]); RBC and Leucocyte velocity (μm/sec) and number; proportion of perfused vessels (PPV [o]): Microvascular flow index; Flow heterogeneity (MFIhet or MC velocity and flow or other parameters listed here expressed as a function of a histogram of MC variables); number of non-sticking; rolling and sticking leukocytes (μm/sec), number of leucocytes, microcirculatory RBC Hb saturation, capillary tube and discharge haematocrit. The latter (tube and discharge) haematocrit values are integrated into a single parameter that describes the oxygen carrying capacity of the microcirculation and is called tissue red blood cell perfusion (tRBCp). The above parameters are measured in steady state but also as a result of a challenge (e.g. metabolic, vasodilator, blood transfusion, exercise). Microcirculatory parameters obtained from other techniques than IVM such as laser speckle imaging, laser Doppler, echo, contrast enhanced ultrasound.

Morphological and spectroscopic parameters including but not limited to total vessel density (TVD [mm/mm2]); functional microcirculatory structures (sputum glands; orifices, vessel loops, rectal crypts, microcirculatory units related to organ function, intestinal villi, renal tubular structures, liver lobule, alveoli, glycocalyx dimensions (e.g. measured using IVM and/or RBC perfused boundary region, tortuosity, fractal dimensions; bifurcations of MC vessels. AI identification of mean values but also of histograms of the distributions of said parameters within a population or within a single measurement of the microcirculation (field of view), or within a single capillary. Morphometric information can be obtained from IVM imaging but also from histological analysis of tissue samples such as obtained from biopsies. In addition to these values, spectroscopic measurements concerning tissue and plasma constituents as well morphometric information regarding the MC obtained from optical coherence tomography and confocal microscopy are included as input variables in the assessment of the MC.

Surrogates of organ perfusion are also used to identify microcirculatory alterations. These types of parameters include among other capillary refill time, peripheral temperature, arterial venous CO2 gap, gastric tonometry, near infrared spectroscopy. Also included are the listed in the Clinical and health related data set section. The classified output parameters of this AI analysis include biometric finger print of health classifying risk of a morbidity and mortality (e.g. scores from the use of DALY, or SOFA, or APACHE. The input parameters described herein this first embodiment are also used as the input parameters listed in all embodiments from the second embodiment to the sixty-eighth described below in addition to the specific additional input parameters specified in each of the said embodiments.

A second embodiment is the method wherein AI is used to allow classification and identification of various classes of microcirculatory alterations (as discussed in reference [11]) and relate them to various disease states. In doing so AI algorithms will analyze and search for microvascular properties which relates to health and disease. IVM analysis will identify best therapy and evaluate the success of therapy in terms of an identification of the outcome. Quantification of various functional parameters has been achieved in prior art by the use of either manual or semi automatic image analysis software (e.g. as discussed in reference [13]). Hilty (as discussed in reference [7]) discloses an automatic analysis software platform, but not based on self-learning or AI, of the various functional parameters related to the microcirculation as required by a recent international guide lines on formulated by task force of the European Society of Intensive Care Medicine [11]. These studies have shown that analysis of the microcirculation forms an independent sensitive and early diagnostic measure to identify various cardiovascular disease states. When combined with conventional evaluation of the systemic circulation parameters such as heart rate their sensitivity and specificity as a diagnostic platform to predict mortality and morbidity improves even further. MC values can be presented as mean values but also as histograms of the distributions of said parameters. AI based analysis of the various microcirculation alterations allows a differential diagnosis to be made of the underlying disease, guide therapy as well as indicating the success (or failure) of the various therapeutic intervention affecting the cardiovascular system. The input variable parameters in this IVM analysis include but not limited to those microcirculatory parameters listed in the first embodiment and discussed in reference [11]. Conventional clinical data are added to the IVM system to further support the output of AI analysis. The classified output parameters of this IVM analysis include but not limited to are those associated with quantification of the state of health and disease as listed in the section on Clinical and health related data set found above.

A third embodiment is the method wherein IVM analysis of microcirculation plus other clinical parameters disclosed herein is used to identify the functional state of the patient (e.g. states of cardiogenic, traumatic, obstructive or septic/distributive shock (11) and identify which resuscitation strategy will be most effective during resuscitation of the MC and when further resuscitation is futile and identify what aspect of the microcirculation needs resuscitating. The input variable parameters in this IVM analysis include but not limited to those outlined in the first embodiment; the values needed to make such categorization are described in detail this consensus paper. Additional clinical input variable parameters as well as settings of ECOS are added to this IVM analysis include but not limited to classification of the state of shock (as described in reference [11], classification of the severity of organ dysfunction (as quantified by SOFA scores, identification of length of ICU and hospital stay, quantification of DALY.

A fourth embodiment is the method wherein IVM analysis of MC alterations is used to identify organs at risk of failure, including identification of heart, liver, brain failure. The input variable MC parameters in this IVM analysis include but not limited to those outlined in and include input parameters such as MC blood flow, TVD, FCD, PVD including those outlined in the First Embodiment. Other parameters which can be included are values derived from contrast enhanced ultrasound, speckle imaging, laser Doppler, cardiac ultra sound, MRI, X-ray, systemic variables blood pressure and cardiac output, venous pressures, creatine clearance, fluid balance and lactate. The classified output parameters of this IVM analysis include but not limited to classification of the state of shock (as described in reference [10,11]), classification of the severity of organ dysfunction (as quantified by SOFA scores, identification of length of ICU and hospital stay, quantification of DALY following discharge).

A fifth embodiment is the method wherein IVM alterations are used to identify the need for continuous renal replacement therapy (see for the input variable parameters in this IVM analysis include but not limited to the same as the fourth embodiment}. Also, for indication of attachment of an adsorber filter for removal of endotoxin, viruses, inflammatory mediators, unwanted drugs or toxins and/or free haemoglobin. The input variable parameters in this IVM analysis include all conventional parameters related to assessment of kidney function, including laser speckle, echo and IVM derived MC parameters. The classified output parameters of this AI analysis include but not limited to quantification of renal dysfunction, need for haemodialysis, classification of the state of shock, classification of the severity of organ dysfunction (as quantified by SOFA scores and Apache score).

A sixth embodiment is the method wherein IVM analysis of MC is used to identify which type of intravenous fluids or a blood transfusion will best resuscitate patients and provide a target for titration of intravenous fluids and blood needed during ICU and cardiac and general surgery and identify when further fluid resuscitation is futile. To distinguish between the different types of fluids required and identify which compartment fluids are accumulating (e.g. intravascular, interstitial and intracellular), The latter two can be identified by use of tissue bio-impedance. The input variable parameters in this IVM analysis include those parameters outlined in the first embodiment. Also included are systemic variables include haemoglobin concentration, blood gas measurement, weight of patient, cardiac output (stroke volume) mean arterial pressure (MAP) and venous pressure and other values described elsewhere. Amount and type of fluid already administered, use of diuretics, fluid overload are also regarded as input parameters. In examples of the invention, tissue water content is also measured as determined by bioimpedance measurements able to discriminate between extra and intracellular water. Inflammatory and markers and markers of oxidative and nitrosative stress are also included. The classified output parameters of this IVM analysis include but not limited to improvement of kidney function as quantified by the KDIGO score (as described in reference 18), Morbidity, the presence of inflammation, atrial fibrillation, ECG, mortality, need for fluid and toxin removal by haemodialysis, need for initiation of diuretics, improvement of organ function as quantified by SOFA scores, identification of length of ICU and hospital stay, quantification of DALY, if chronic kidney disease persists following ICU, length of ICU and hospital stay, DALY following discharge.

A seventh embodiment is the method wherein IVM analysis of MC is used to show changes in microcirculatory function and morphological improvement related to health as a result of exercise and therapy. It has been reported that exercise (>150 min/week) in hypertension patients results in improved functional capillary density and red blood cell flow.

Improvement of the MC can also be achieved by therapy, for example, by use of cardiac assist devices. It has been shown that sustained improvement of the MC using such Impella technology can be used for bridge to treat following myocardial infarction. Following session of the Impella treatment MC function which had improved during Impella therapy remained improved following withdrawal of the Impella device. Similarly, it has been shown that weaning from an ECOS can be judged as a result of sustained improved sublingual red blood cell flow upon reduction of ECOS pump flow. It has been shown that such devices or cardiotonics in heart failure increased MC function and cardiac output and that such improvement resulted in improved survival or not following cardiac arrest. These devices also include cardiac assist devices, pacemakers and cardiac resynchronization devices. Thus, in this embodiment, the IVM analysis of MC predicts an improvement of cardiovascular function and improvement of heart function. The input variable parameters in this IVM analysis include RBC flow, TVD, FCD plus the other parameters listed in the first embodiment. The classified output parameters of this IVM analysis include improved microcirculatory function as quantified by the variables (see first embodiment), heart function, reduction in SOFA score (quantification of organ function), improvement in DALY following ICU discharge, Morbidity, mortality, improvement of heart function (measured by echo, left ventricular function and ECG analysis, less need for heart support devices (ECOS), reduction in length of ICU stay and hospital stay.

An eighth embodiment is the method wherein IVM analysis of tumours local or distant undergoing treatment is used to provide a target for therapy such as surgery (resection borders) or chemo/photodynamic/radiotherapy. It has been shown that shrinkage of the oral tumour microcirculation (total vessel density, red blood cell flow and functional capillary density) occurs following local treatment by photodynamic therapy. Measurement of microcirculatory RBC flow increased in leukaemia patients following chemotherapy due to reduced blood viscosity associated with reduced leucocytes in the microcirculation. This MC measurement can show maximum therapeutic outcome (e.g. determine improvement by sensing reduction of leucocytes in leukaemia). In another study, the effects of bevacizumab (angiogenic inhibitor a potent vasoconstrictor; too much of this drug can cause dangerous myocardial infarction) has been shown to reduce FCD during the treatment and returns to baseline when stopping administration. IVM analysis during administration can predict either beneficial or deleterious effects of drugs thereby identifying whether the drug is effective, and identify its dose and time to stop avoiding complications. The input variable parameters in this AI analysis include but not limited to RBC flow, TVD, FCD plus the other parameters listed in the first embodiment. The classified output parameters of this IVM analysis include tumour regression as quantified by imaging and/or biomarkers, need for surgery, further tumour therapy, morbidity, mortality, quantification of DALY, resolution of tumour resection, recurrence of tumour.

A ninth embodiment is the method wherein IVM analysis of MC is used to identify dehydration in patients such as occurs in perioperative and ICU patient and in children (infectious diseases, diarrhoea) and elderly in need of fluid resuscitation and or hydration. Dehydration is very difficult to diagnose, however and advantageously, dehydration can be diagnosed effectively by IVM analysis, as described herein. The input variable parameters in this AI analysis include RBC flow, tissue RBC perfusion, TVD, FCD, capillary Ht plus the other parameters listed in the first embodiment. Dehydration can result in an increase or decrease in capillary haematocrit, a reduction in the functional capillary density and a slowing down of the red blood cell velocity; input clinical variables include body weight changes, skin properties, blood pressure, mouth dryness. The classified output parameters of this AI analysis include normalization of MC parameters back to base line, increase of body weight, normalization of urine production, biochemical composition and colour, strength, frailty, morbidity, mortality, DALY, weight, skin turgor and dryness, oral dryness.

A tenth embodiment is the method wherein IVM analysis of changes in MC of patient suffering from hypertension and diabetes are used to identify progress to organ damage such as heart or kidney failure and/or stroke. The input variable parameters in this IVM analysis include MC tortuosity, RBC flow, TVD, FCD plus the other parameters listed in the first embodiment. The classified output parameters of this IVM analysis include but not limited to classification of morbidity prediction, mortality prediction, decreased chance of heart failure reduced chance of stroke, improvement of heart function as quantified by heart function variables, kidney function, a need for heart support devices, length of ICU and hospital stay, morbidity as quantified by DALY.

An eleventh embodiment is the method wherein IVM analysis of MC is used for evaluating how long organs have been ischemic and identify the usability of organs harvested from non-heart beating donors to be accepted by the recipient. The input variable parameters in this AI analysis include but not limited to red blood cell velocity and FCD of donor and of the organ surface in steady state while attached to the donor and in the recipient plus those parameters outlined in the first embodiment. IVM analysis of MC as a result of organ placement or a regional challenge resulting in restoration of microcirculatory red blood flow and FCD. In addition, the presence and activity of leucocyte in the MC is analyzed as input variables. The classified output parameters of this IVM analysis include the duration which transplanted organs would be tolerated after transplantation.

A twelfth embodiment, aligned to the ninth example embodiment, is the method wherein IVM analysis of MC will distinguish between dehydration and hypovolemia and suggest which type of fluid will best resuscitate the patient (those listed in the first embodiment input variables). Input variables: various well-established parameters related to the hemodynamic assessment related to hypovolemia; including fluid responsiveness, skin turgor and dryness, oral dryness, cardiac output, body weight, MC variables in the first embodiment The classified output parameters of this AI analysis include but not limited to classification of improvement of kidney function.

A thirteenth embodiment, aligned to the twelfth example embodiment as they are both related to organ transplants, is the method wherein IVM analysis of MC of an organ and of the organ recipient is used to determine whether therapeutic support is needed to improve the success of organ transplantation. Input variables: various well-established parameters related to the hemodynamic assessment related to hypovolemia; including fluid responsiveness, skin turgor and dryness, oral dryness, cardiac output, body weight, MC variables in the first embodiment. The classified output parameters of this AI analysis include classification of improvement of organ function especially that of the kidney.

A fourteenth embodiment, aligned to the twelfth example embodiment as they are both related to organ transplants, is the method wherein IVM analysis of MC is used to monitor and identify if an organ will be rejected or acceptance over time (short and long term). The input variable parameters in this IVM analysis include microcirculatory parameters listed in the first embodiment. The classified output parameters of this AI analysis include those associated with quantification of the state of health and disease as listed in the section on clinical and health related data set found above.

A fifteenth embodiment, aligned to the sixth example embodiment as they are both related to treatment of shock, is the method wherein IVM analysis of MC is used to allow optimal dosing of therapeutic drugs (fluids, vasopressor agents, vasodilators) to obtain optimal hemodynamic response. The input variable parameters in this AI analysis include but not limited to include as MC parameters FCD, red blood cell velocity including those listed in the first embodiment. The classified output parameters of this AI analysis include classification of improvement of organ function as quantified by SOFA KDIGO (18) and APACHE scores, classification of morbidity prediction, mortality prediction, need for extracorporeal organ support (ECOS).

A sixteenth embodiment, aligned to the twelfth example embodiment as they are both related to organ transplants, is the method wherein IVM analysis of MC is used to identify impending death and allow identification of the time to death to allow decisions to be made for organ removal or family contact (FCD, RBC flow (with and without a challenge (e.g. passive leg raising), nitro-glycerine regional challenge, leucocytes) in addition to clinical variables blood pressure body temperature, EEG, ECG). The input variable parameters in this IVM analysis include RBC flow, TVD, FCD plus the other parameters listed in the first embodiment. The classified output parameters of this AI analysis include but not limited to classification of mortality prediction and organ acceptance by the recipient A seventeenth example embodiment focused on the identification and treatment of cancer is the method wherein IVM analysis of MC is used to identify when tumour therapy (e.g., angiogenic inhibitors such as Bevacizumab, chemoi-radio/photodynamic therapy) should be indicated and when maximum doses is reached in advanced of the occurrence of complication such as myocardial infarction (input parameter FCD and RBC velocity in addition to blood pressure, ECG). The input variable parameters in this IVM analysis include those listed in the first embodiment. The classified output parameters of this IVM analysis include but not limited to classification of tumour regression as indicated by imaging and biomarkers and DALY as measure of outcome.

An eighteenth example embodiment focused on the identification and treatment of heart disease is the method wherein IVM analysis of MC is used to identify placement of leads for treatment of arrhythmia associated heart failure using cardiac resynchronization therapy. Here it is uncertain where the optimal placement of leads should be made. Looking at the response of this therapy to the AI analyzed MC will identify optimal placement of leads to avoid arrhythmias and progress of heart failure. The output variable parameters in this IVM analysis include successful classified placement of leads for treatment of arrhythmia and associated improvement of heart function, and DALY as measure of long-term outcome.

A nineteenth example embodiment, aligned to the nineteenth example embodiment as they are both focused on the identification and treatment of heart disease is the method wherein HVM analysis of MC is used to identify the presence of diabetes and the identification of the presence or development to heart failure and identify which medication or treatment (Input variables: indication for cardiac assist devices) will be most effective. The input variable parameters in this AI analysis include those listed in the first embodiment. The classified output parameters of this AI analysis include identification of reduction of occurrence of diabetes as quantified by measures of diabetes and identification of reduction in the prevalence of heart failure.

A twentieth example embodiment which may be aligned with the fifth example embodiment, is the method wherein IVM analysis of MC is used to identify the progress and severity of kidney disease including but not limited to chronic and acute kidney failure. The input variable parameters in this AI analysis include but not limited to those listed in the first embodiment. The classified output parameters of this IVM analysis include but not limited to creatinine clearance, BUN (blood urea nitrogen), oliguria and other variables outlined KDIGO guidelines.

A twenty-first example embodiment focused on a concept of providing a challenge to identify properties of the MC, as described earlier, which may also be optionally included as being part of an IVM measurement. Thus, this example method wherein AI analysis of MC is used to evaluate the properties of the microcirculation in relation to health and disease upon providing a regional or systemic challenge e.g.

a pharmacological challenge (e.g. Acetylcholine, nitro-glycerine), therapeutic challenge (e.g. fluid, vasopressor, inotropic, leg raised challenge) or exercise. The classified output parameters of this AI analysis include microcirculatory variables as a result of a challenge correlated with improved organ functions (SOFA).

A twenty-second example embodiment, which may be aligned with the eighteenth example embodiment focused on the identification and treatment of cancer, is the method wherein AI analysis of MC of organ surfaces is used to identify the presence of micro metastasis by identification of abnormalities in vessel structures seen during surgery also on organ surfaces or externally (oral cancers, melanoma) for intraoperative treatment. AI based decision can be made for choosing a resection plane. The input variable parameters in this AI analysis include those listed in the first embodiment. The classified output parameters of this AI analysis include but not limited to reduction of cancer variables (those listed in the eighth embodiment), reduction in DALY.

A twenty-third example embodiment focused on a general concept of applying IVM applications during surgery on, for example, intestinal resections, cardiac surgery, liver resections and in ovarian, oral and brain cancer. AI analysis of MC of the lungs (alveoli) can be used to evaluate the ventilation perfusion matching and other lung pathologies during surgery and for clinical decision making in relation to lung surgery. The input variable parameters in this AI analysis include but not limited to those listed in the first embodiment. The classified output parameters of this AI analysis includes, but is not limited to, improvement of lung related function and tumour markers as well as x-ray analysis and DALY related output variables.

A twenty-fourth example embodiment, which may be aligned with the seventh and tenth example embodiments, is the method wherein AI analysis of MC is used as a lifetime finger print starting at birth (including MC of the prenatal mother and father) and/or neonatal ICU skin and/or of other organ surface identifying disease later in life or of congenital defect or of impending disease of the mother (e.g. pre-eclampsia, smoking, body weight) or of the father (similar risk factors). Such measurements can be added to the health parameters of patients of large databases of patients currently being followed long term (e.g. diabetic and/or arteriosclerosis patients), see clinical variables listed in the data set section. Also, different MC variables at birth can be different depending on genetics and environmental factors. The input variable parameters in this AI analysis include but not limited to first embodiment including genetic markers related to risk of acquiring disease later on in life. The classified output parameters of this AI analysis include but not limited to early identification of clinical symptoms allowing therapeutic window in advance of morbidity and mortality as well as quality of life. The output parameter classification of this embodiment is optionally done in terms of the assessment of DALY, and reduction in the variables listed in the section "Clinical and health related data set".

A twenty-fifth example embodiment, which may be aligned with the twenty-fifth example embodiment, is the method wherein AI analysis of MC alterations and other biomarkers of health for AI based decision making allowing reduction in health care costs by smarter allocation of resources. The input variable parameters in this AI analysis found in the first embodiment including genetic markers related to risk of acquiring disease later on in life as well as costs of health care resources spent on the patient and expected costs. Can determine life insurance or other health related insurance policy coverage. Input variable parameters in this AI also include those listed in the first embodiment. The classified output parameters of this AI analysis include but not limited to reduction in health care costs due to early discharge, early resolution of disease, prognosis of DALY.

A twenty-sixth example embodiment, which may be aligned with the twenty-fifth example embodiment, is the method wherein AI analysis of MC is used as an indicator of health which can be trained as a result of exercise. Improvement of the MC (e.g. total vessel density) can be used as an AI targeted MC improvement exercise program. The input variable parameters in this AI analysis include those listed in the first embodiment. The classified output parameters of this AI analysis include improved health indicators of longevity, fitness, less morbidity, less frailty (multimorbidity score quantified by frailty score), improved DALY.

A twenty-seventh example embodiment, which may be aligned with the twenty-fifth example embodiment, is the method wherein AI analysis of MC is used as an indicator of health as a result of senescence therapy for dosing and showing improvement as age related deterioration of MC function is halted related to improved life span and health. The input variable parameters in this AI analysis include but not limited to in the first embodiment. The classified output parameters of this AI analysis include but not limited to improved health indicators of longevity quantified by DALY.

A twenty-eighth embodiment is the method wherein IVM analysis is used to identify if an intended therapeutic intervention will provide a positive result, Input variable parameters in this AI include those listed in the first embodiment. The classified output parameters of this AI analysis include but not limited to assessment of multimorbidity and DALY.

A twenty-ninth embodiment is the method wherein IVM analysis of wounds, such as decubitus, burns venous ulcers, radiotherapy, dermatological disorders, melanoma, urogynaecology surgical wounds, surgical wounds (sternitis) in the cervix (tumour resection) pelvic and vaginal related to surgical treatment placement of mesh mat) is used to identify severity of disease (including vaginal vault prolapse, surgical treatment of prolapse and wound healing and the success of mesh implantation). Input variables: regional vaginal microcirculatory parameters as well as those near the surgical area obtained by NM and endoscopy and biopsy. Focus of vaginal MC focus depth as a measure of vaginal atrophy. Especially relevant parameters are related to morphological variable characterizing microcirculatory formations. Input variable parameters in this AI include those listed in the first embodiment. The classified output parameters of this IVM analysis include but not limited to recurrence of tumour and or resolution of wound healing following surgery and or recurrence of prolapse improvement in the microvasculature surrounding the wound.

A thirtieth example embodiment, which may be aligned with the eighteenth example embodiment focused on the identification and treatment of cancer, is the method wherein AI analysis of MC response to therapy as well as early detection of cancerous tissue is described (e.g. cancer (brain and abdominal tumours, lung, leucocytes), osteo radio necrosis, squamish cell carcinoma, decubitus, peripheral vascular disease). It has been shown using HVM that it takes about seven days for the microvasculature to develop to base line after a surgical wound has been made growth (Input variables: FDC, TVD) in oral wound healing following therapy which can be improved to a time of 3 days upon application of platelet enriched gel. Reduction of microvascular TVD following angiogenic inhibitor and following photodynamic therapy has been shown. The input variable parameters in this AI analysis include but not limited to parameters in the first embodiment plus histological microcirculation variables obtained from biopsies. The classified output parameters of this AI analysis include but not limited to identification of reduction of vascular growth on tumour, successful resolution of surface tumours, reduction of tumour biomarkers (see output variables listed in the eighth embodiment).

A thirty-first example embodiment, which may be aligned with the eighteenth example embodiment focused on the identification and treatment of cancer, is the method wherein AI analysis of MC is used to identify success of radio/photodynamic/chemotherapy/surgery and identify if there is a need for adjuvant therapy (e.g. vasodilatory therapy, hypothermia, hyperbaric oxygenation, further surgery), See input and output variable in the previous embodiment thirtieth. Input variable parameters in this AI include those listed in the first embodiment. The classified output parameters of this AI analysis include but not limited to those listed in the eighth embodiment.

A thirty-second example embodiment, which may be aligned with the twenty-fifth example embodiment, is the method wherein AI analysis of MC is used to provide a finger print of the state of (micro-)vascular health which can be followed over years either in health (e.g. change in age) or as a result of exercise program. Impending disease based on risk. Besides for personal health this could also be used for pre-operative boosting of cardiovascular health (input parameters TVD/PVD/FCD/tRBCp and functional MC reserve identified by a challenge (e.g., nitro-glycerine) with the aim (outcome parameters) of reducing post-operative or therapeutic complications (e.g. chemo/photodynamic/radiotherapy, cardiac surgery). Input variable parameters in this Analysis include but not limited to those listed in the first embodiment. The classified output parameters of this IVM analysis include but not limited to improvement in DALY, frailty score, multimorbidity free days.

A thirty-third embodiment is the method wherein IVM analysis of MC is used to identify if a patient is at risk for developing myocardial infarction, a stroke). In some examples of the invention, a presence of emboli is observed either by itself or as a result of over medication (e.g. protamine during cardiac surgery) as well as long term effects of microvascular alterations following hypertension. Input variable parameters are outlined in the first embodiment. The classified output parameters of this IVM analysis include improved DALY, multi-morbidity score, avoidance of MI or stroke, reduced thrombosis medication, improved exercise capacity.

A thirty-fourth embodiment is the method wherein IVM analysis of the MC is used to identify development from diabetes to heart failure. The input variable parameters in this IVM analysis include those listed in the First Embodiment. The classified output parameters of this IVM analysis include but not limited to the classification and diagnosis of diabetes as recommended by the American Diabetes Association and improvement of parameters related to organ dysfunction.

A thirty-fifth embodiment is the method wherein IVM analysis is used to identify development of dementia and Alzheimer and success of therapies (e.g. exercise). The input variable parameters in this IVM analysis include those in the first embodiment including tests related to measurement of brain and neurological function. The classified output parameters of this IVM analysis include but not limited to improved mental health and brain function, organ dysfunction, DALY indicators.

A thirty-sixth example embodiment focused on the identification and treatment of heart disease and may additionally or alternatively be used for kidney disease is the method wherein IVM analysis of MC is used to allow the identification of the use of attaching ECOS devices such as cardiac and renal assist devices such as artificial kidney, Left Ventricular Assist Device, ECMO, home mechanical ventilation, but also implantable assist or organ replacement devices such as an artificial heart, valves, kidneys and such like.

Here not only will IVM allow determination of the optimal settings of said devices, but will indicate whether extra devices or therapy are needed and identify the presence of complications in advance of clinical symptoms (e.g. the identification of tamponade in addition of clinical symptoms). Also, in this embodiment IVM analysis of self-made IVM images at home can allow a subject to self-diagnose if there is any indication of need to contact health provider or if all is well. Information regarding IVM analysis can be transmitted to a health care provider via telemetry for continuous monitoring or gsm. The input variable parameters in this IVM analysis include those listed in the first embodiment. In addition, variables derived from wearable sensors being currently developed providing home care medical (heart rate, blood glucose, ECG, blood pressure) can be added. The classified output parameters of this IVM analysis include early detection of impending organ failure {e.g. cardiac tamponade), reduction in the occurrence of ECOS related complications, early identification of the need to re-adjust intra or extracorporeal organ support devices, timely consult to initiate therapy, early weaning from ECOS, including cardiopulmonary bypass and mechanical ventilation.

A thirty-seventh example embodiment focused on the identification and treatment of heart disease and may additionally or alternatively be used for kidney disease and/or a use of extracoporeal organ support (EGOS) is the method wherein IVM analysis of MC is used to determine necessity and success of implantation of organ support devices planted internally such as pacemakers, renal and heart assist devices, cardiac resynchronization leads. The input variable parameters in this IVM analysis include but not limited to those in the first embodiment. The classified output parameters of this IVM analysis include but not limited to success of functional organ support quantified in terms of renal function and heart function improvement.

A thirty-eighth example embodiment focused on the identification and treatment of infectious disease is the method wherein IVM analysis of MC is used for the identification of patients at risk of or having tropical diseases including but not limited to malaria, sickle cell disease, dengue, HIV, Ebola and parasite infections. In this way IVM analysis of MC will introduce blood-less diagnosis of these disease states. The input variable parameters in this IVM analysis include the detected and classified abnormal microcirculatory dynamics and detected blood born parasites directly or indirectly via altered MC variables. The classified output parameters of this IVM analysis including the identification of the number of patients in need of further invasive blood diagnosis out in the field, for the early treatment medication. i.e., successful identification of infected patients. Reduction in the need for invasive blood measurements, reduction in disease by early detection, furthermore is improvement of public health care reduction of costs associated with detection of infection in low resource countries, reduction in DALY and multimorbidity score.

A thirty-ninth example embodiment focused on the identification and treatment of thrombosis and haemostasis is the method wherein IVM analysis of the MC in relation to haemostasis is used to identify an occurrence of deep vein thrombosis. Identification of amount of medication and type of medication needed to achieve haemostasis. The input variable parameters in this IVM analysis include but not limited to those listed in the first embodiment. The classified output parameters of this IVM analysis include but not limited to Reduction or avoidance of the occurrence of stroke and thrombosis.

A fortieth example embodiment focused on the identification and treatment of kidney disease and/or a use of extracoporeal organ support (ECOS) is the method wherein IVM analysis of MC is used during the course of haemodialysis and blood purification (by use of filter or absorbers) processes to identify the moment of cessation because of the occurrence of hypotension or the need to adjust parameters. The input variable parameters in this IVM analysis include those related to the detection of hypovolemia and hypotension and those outlined in the first embodiment and the response to a challenge such as leg raising and input variables from bio impedance. The classified output parameters of this IVM analysis include but not limited to the avoidance of the need for a blood transfusion because of the development of hypovolemia because of too much haemodialysis. Avoidance of severe hypotension during a haemodialysis session. Reduction in the time to completion of a haemodialysis session. Improvement of renal functional parameters (BUN, creatinine, lactate)

A forty-first example embodiment, which may be aligned with the seventh example embodiment, is the method wherein IVM analysis of MC is used for a personal care device which will allow recipient to monitor one's own vascular health as a response to exercise or as a warning to developing disease. The input variable parameters in this IVM analysis include IVM related variables listed in the first embodiment. The classified output parameters of this IVM analysis include improvement of improvement in DALY score, frailty score, multi-morbidity score.

A forty-second example embodiment, which may be aligned with the seventh example embodiment, is the method wherein IVM analysis of MC of large populations of patients under different conditions of disease and therapy collected in a database is used to identify which therapies are most effective in treating such disease states. The input variable parameters in this IVM analysis include but not limited to those listed in the first embodiment Output variables: Learning data set for AI related identification and classification of disease and effectivity of therapy, DALY, SOFA, APACHE scores.

A forty-third example embodiment, may be aligned a testing of an efficacy of drugs or a combination of drugs, is the method wherein IVM analysis of MC alterations of states of disease is used to identify the specifications of as yet not existing or developed drugs or therapy or organ support devices which will have a best therapeutic benefit. Combination of therapy directed by AI analyzed MC measurement are described or identification or treatment of hypotension and hypovolemia. The input variable parameters in this IVM analysis include those listed in the first embodiment. The classified output parameters of this IVM analysis include but not limited to the development of new drugs and therapeutic modalities more effective in resolving the disease than previous medication. Quantification in morbidity, DALY, SOFA.

A forty-fourth example embodiment, may be aligned a testing of an efficacy of drugs, is the method wherein AI analysis of MC is used to identify whether a certain type of drug will improve outcome. The input variable parameters in this IVM analysis include those listed in the first embodiment. The classified output parameters of this IVM analysis include but not limited to Improved SOFA and APACHE score. Improvement in organ function to which the drug is targeted.

A forty-fifth example embodiment focused on the use of IVM during surgery where there is an impending hypotension and depth of anaesthesia may be identified, is the method wherein IVM analysis of MC of sublingual and organ surfaces is used as an anaesthesia tool to evaluate depth of anaesthesia as well as the need for hemodynamic support as well as for procedures, such as cardiopulmonary bypass, cell saver and procedures related to haemostasis associated with cardiac surgery. The input variable parameters in this IVM analysis include but not limited to those listed in the first embodiment. The classified output parameters of this AI analysis include the use of less aesthetic drugs than conventional assessment, shorter postoperative recovery, less need for drugs to stabilize hemodynamic (vasopressor, vasodilators) successful outcome with less complications.

A forty-sixth example embodiment focused on use of IVM during surgery where there is an impending hypotension and depth of anaesthesia may be identified is the method wherein AI analysis of MC is used as a surgical IVM tool during surgery to evaluate the danger of anastomotic leakage, identification of the resection boundary, the presence of unidentified metastatic tumours. Visual inspection of lesions boundaries, anastomose, histology or other conventional methodologies. The classified output parameters of this IVM analysis include but not limited to recurrence of tumour (see for methodologies the Eighth Embodiment), the occurrence of postoperative anastomotic leakage (reduction by use of AI assisted MC assessment).

A forty-seventh embodiment is the method wherein IVM analysis of MC is used by taking retinal microcirculation measurements as an input (currently in retinoscopy vessels >100 µm are being examined) to evaluate for identification of eye disease and also of impending neurological disorders and brain disease such as stroke and coma and subarachnoid haemorrhage. The input variable parameters in this IVM analysis include but not limited to microcirculatory images of the retina and variables listed in the first embodiment. The classified output parameters of this IVM analysis include non-invasive detection of brain disorder compared to MRI or other imaging methodologies, reduction in costs.

A forty-eighth example embodiment, which may be aligned with the forty-eighth example embodiment, is the method wherein IVM analysis of MC of retinal (also conjunctival) is used to identify the danger of stroke, depth of coma, subarachnoid haemorrhage as well as this brain and eye diseases. Input and output variables similar to those of the Forty-eighth Embodiment.

A forty-ninth example embodiment, which may be aligned with the sixth example embodiment, is the method wherein IVM analysis of MC is used as a resuscitation target in traumatic haemorrhage or stroke and identification of optimal strategy including decisions related to the use of blood transfusion vasoactive compounds and or fluids. The input variable parameters in this IVM analysis include but not limited to those listed in the First Embodiment plus other conventional clinical variables. The classified output parameters of this IVM analysis include but not limited to identifying survival, improved renal function (KDIGO) and organ function (SOFA scores) a reduction in the amount of fluids needed to resuscitate, a reduction the amount of blood needed, a reduction in the number of vasopressors needed.

A fiftieth example embodiment focused on use of IVM for end-of-life diagnosis or treatment is the method wherein IVM analysis of MC is used for making end of life decisions by predicting death in hospices and ICU. The input variable parameters in this IVM analysis include but not limited to those in the First Embodiment. The classified output parameters of this IVM analysis include but not limited to correct identification of time of death.

A fifty-first example embodiment focused on use of IVM for blood transfusions is the method wherein IVM analysis of MC is used to detect increased RBCs (Hb) in the MC of athletes to assess if doping has been used (e.g. blood transfusions or EPO meant as a means of increasing Hb availability for better oxygen delivery). The input variable parameters in this IVM analysis include those in the First Embodiment especially variables related to RBC availability, capillary hematocrit, FCD. The classified output parameters of this IVM analysis include correct identification of athletes having used blood transfusions or EPO.

A fifty-second example embodiment focused on use of IVM for brain stroke diagnosis and treatment. In this embodiment IVM analysis of MC of conjunctiva, retina and of this organ is used to identify and evaluate multiple sclerosis, critical illness, stroke, coma. Input and the classified output parameters of this IVM analysis include but not limited to same as the forty-eighth example embodiment.

A fifty-third example embodiment focused on the identification and treatment of kidney disease is the method wherein IVM analysis of MC is used to allow dialysis devices including personalized miniaturized artificial kidney devices to react to unexpected changes occurring during dialysis treatment. Those listed in embodiment 46 for input and output variables.

A fifty-fourth example embodiment focused on a general concept of applying IVM applications during surgery is the method wherein IVM analysis of MC is used in intraoperative decision making for resection of tumours for example are done by taking histological frozen sections and taken to this location for analysis to then continue with surgery after a clinical decision making. IVM analysis of the MC of the organ and area of suspicion can be made to categories the stage of tumour aiding in a decision to resect or not saving valuable operation time (during operation biopsy has to be evaluated while the surgeon waits). The input variable parameters in this IVM analysis include but not limited to histological analysis of biopsy and the input variable parameters of eighth embodiment. The classified output parameters of this AI analysis are similar to the eighth embodiment.

A fifty-fifth example embodiment focused on a general concept of applying IVM applications for oncology and endoscopy is the method wherein IVM analysis of MC of the cervix is used as a screening device for diagnosis of cervical cancer. Whereas currently biopsies are made and need to be histological analyzed during the surgery taking time and costs. The input variable parameters in this IVM analysis include histological analysis of biopsy and the input variable parameters of eighth embodiment. The classified output parameters of this IVM analysis are similar to the eighth embodiment.

A fifty-sixth example embodiment focused on a general concept of applying IVM applications for oncology and endoscopy is the method wherein IVM analysis of MC of the cervix and vaginal wall is used to assess the need for prolapse surgery and the success of wound healing following urogynaecology surgery and attachment of materials to the uterus wall. The input variable parameters in this IVM analysis include but not limited to histological analysis of biopsy, and the input variable parameters of eighth embodiment. The classified output parameters of this IVM analysis are similar to the eighth embodiment and identification of time for rejection of materials and resistance to wound healing.

A fifty-seventh example embodiment focused on a general concept of applying IVM applications for endoscopy is the method wherein IVM analysis of MC of the vaginal wall is used to diagnose vaginal atrophy and titrate hormone therapy for optimal length of treatment and doses of hormone treatment for vaginal atrophy. The input variable parameters in this IVM analysis include the morphology of the vaginal microcirculation network, amount of hormone treatment, clinical symptoms, the depth of focus of the vaginal microcirculation (in µm). Output parameter reduction of clinical symptoms associated with vaginal atrophy, reduction and efficacy of hormone treatment.

A fifty-eighth example embodiment focused on a general concept of applying IVM applications for endoscopy is the method wherein IVM analysis of endoscopic rectal sigmoid MC crypts is used to identify presence of inflammatory bowel disease (IBD). In this embodiment abnormal geometry of the crypts are associated with Crone and colitis. The input variable parameters in this IVM analysis include but not limited to first embodiment applied also to rectal microcirculation plus endoscopy results and biopsy results. The classified output parameters of this IVM analysis include but not limited to avoidance of the need to take a biopsy, increased diagnostic sensitivity in comparison to conventional endoscopy.

A fifty-ninth example embodiment focused on a general concept of applying IVM applications for diagnosis and treatment of infectious diseases is the method wherein IVM analysis of MC used to allow the detection of abnormal leucocyte dynamics or presence of a large amount of leucocytes indicating states of inflammation or the presence of leukaemia. Resolution of abnormal leucocyte kinetics with therapy. The input variable parameters in this IVM analysis include but not limited to First Embodiment especially those related to leukocyte identification, determination of systemic leucocyte amount and type, infection and inflammation parameters. The classified output parameters of this IVM analysis include but not limited to correct identification of blood borne cancers and infections.

A sixtieth example embodiment may use MC generated data with or without other variables related to health in data sets using AI learning to assess health, diagnose disease, identify the type and amount of therapy that will have a maximum therapeutic effect and identify an outcome. In this embodiment, IVM analysis of the MC may be used for routine monitoring by, for example by nurses or other paramedics in the ICU or other wards or in the field for routine screening of patients to detect if an abnormality is present. The input variable parameters in this IVM analysis include those listed in the first embodiment. The classified output parameters of this IVM analysis include early warning of an impending cardiovascular event, infection, sepsis or other pathological crises not detected by routine clinical monitoring.

A sixty-first example embodiment focused on a general concept of applying IVM applications for treatment of trauma and emergency medicine is the method wherein AI analysis of the MC in ambulance service is used to evaluate the cardiovascular status of the patient before and during transport and at the scene of trauma for guidance and timing of resuscitation procedures. The input variable parameters in this IVM analysis include those in the first embodiment. The classified output parameters of this IVM analysis include survival, SOFA score, APACHE score following hospitalization.

A sixty-second example embodiment focused on a general concept of applying IVM applications for identifying and/or reversal of shock is the method wherein IVM analysis of MC is used for identification of the type of shock present, presence of loss of hemodynamic coherence and identification of optimal resuscitation strategy based on the type of the MC alteration detected. The input variable parameters in this IVM analysis include but not limited to the First Embodiment plus systemic variables showing loss of hemodynamic coherence Output variables: Choice of optimal therapy resulting in less organ dysfunction (SOFA score), identification of the type of shock (see reference [11]]) reduced morbidity and mortality.

A sixty-third example embodiment uses MC generated data with or without other variables related to health in data sets using AI learning to assess health, diagnose disease, identify the type and amount of therapy that will have a maximum therapeutic effect and identify an outcome. In this embodiment, IVM analysis of MC may be used to assess if a MC measurement meets the requirements regarding quality of recording a measurement free of artefacts, in order to allow automatic analysis of the images by dedicated AI software, thereby allowing, say, point-of-care application of the measurement. The input variable parameters in this IVM analysis are included in the first embodiment, especially the identity of vessels, venule and capillary red blood cell. An example output variable is a successful MC image suitable for analysis. In this manner, improved, more accurate measurements may be obtained.

A sixty-fourth example embodiment is the method wherein IVM analysis of MC is used to identify whether a sickle cell crisis is imminent and evaluate the efficacy of administered therapy to treat it. The input variable parameters in this IVM analysis include those in the first embodiment. The output variable is the predication of impending crises and efficacy of treatment {e.g. by blood transfusions or haemoglobin-based oxygen carriers or other therapies).

A sixty-fifth example embodiment focused on a general concept of applying IVM applications for blood transfusion identification of anaemia or anaemic shock is the method wherein IVM analysis of the MC is used to diagnose anaemia, the need for blood transfusion and the efficacy of blood transfusion to improve red blood cell and oxygen delivery to the microcirculation such as can occur in anaemia and cardiac surgery. The input variable parameters in this IVM analysis include those in the first embodiment especially capillary Ht, discharge Ht, tissue RBC perfusion and FCD. The classified output parameters of this IVM analysis include promotion of blood saving procedures, treating anaemia with iron EPO or blood transfusion.

A sixty-sixth example embodiment focused on a general concept of applying IVM applications for diagnosis and treatment of sepsis is the method wherein IVM analysis of the MC is used to distinguish between inflammation and infection, and sepsis. Many MC studies using HVM have shown sepsis related microcirculatory alterations to have specific deviations from normal microcirculatory behaviour. The input variable parameters in this IVM analysis include but not limited to those in the first embodiment and the classification of alterations as defined in reference [11] where sepsis related MC alterations are described. Included in these input variables are sepsis related biomarkers as well as the clinical manifestation of sepsis. The classified output parameters of this IVM analysis include but not limited to successful identification of septic patients according to the sepsis guidelines.

A sixty-seventh example embodiment uses MC generated data with or without other variables related to health in data sets using AI learning to assess health, diagnose disease, identify the type and amount of therapy that will have a maximum therapeutic effect and identify an outcome. In this embodiment, IVM analysis of the MC may be used to calculate variables related to the presence of the glycocalys, including the so-called blood perfused boundary region of the capillaries, as marker of glycocalyx barrier function to diagnose health, disease and old age and identify therapeutic strategies aimed at restoration of the glycocalyx. The input variable parameters in this AI analysis include those listed in the First Embodiment The classified output parameters of this IVM analysis include but not limited to Correlation with biomarkers of glycocalyx degradation.

A sixty-eighth example embodiment uses MC generated data with or without other variables related to health in data sets using AI learning to assess health, diagnose disease, identify the type and amount of therapy that will have a maximum therapeutic effect and identify an outcome. In this embodiment, IVM may provide feedback to a user on the quality of images being recorded, values of the functional microcirculatory parameters related to the images being recorded, classifications of microcirculatory abnormalities being recorded, origin of the cause of microcirculatory abnormalities and potential therapeutic strategies expected to normalize microcirculatory abnormalities and resolve disease state (see FIG. 8).

A sixty-ninth example embodiment focused on a concept of applying AI outside of the IVM device is the method wherein an IVM device within which an AI based module can conduct conversations with a remote AI controlled cloud base dataset to allow AI conversational search methodology to be used to provide request for further required input variables needed for more in depth diagnosis and and/or suggestions for further diagnostic information regarding the condition of the patient and/or comparisons to other data sets for providing further insights in to the cause of disease therapeutic options expected to be most effective.

In some examples, prior to a surgical procedure, the IVM may be suitably altered to conform to a surgical setting, e.g. sterility, incorporation in an operating microscope or endoscope.

Thus, in contrast to the teaching of the known art of US2012269420, which identify whether to start or stop resuscitation, examples of the present invention classify and differentiate different types, alterations the IVM described herein identifies different types of resuscitation (e.g., type of fluid, vasopressor or not, blood transfusion etc.). In contrast to the teaching of the known art of US2012269420, which only measures the blood vessels being detected, examples of the present invention propose to also evaluate the maximal available vessels by providing a challenge (e.g., nitroglycerine) in order to determine the maximum recruitable vessels. In contrast to the teaching of the known art of US2012269420, examples of the present invention propose to measure leucocyte kinetics, and/or measure other parameters related to cell structure or subcellular structure (glycocalyx, cell to cell junctions, focal depth, mitochondria). In contrast to the teaching of the known art of US2012269420, which is limited to the the tongue surface examples of the present invention propose to measure on all organ surfaces, including the sublingual area, as well as identifying the benefits of analysing MC during surgery to facilitate real-time decisions during surgery. In contrast to the teaching of the known art of US2012269420, which only regards the measurement of FCD, PPV and TVD to describe the MC and classify red blood cell kinetics only as being sluggish intermittent or normal examples in the present invention include quantitative metrics of RBC kinetics, including RBC velocity and tissue RBC perfusion as well as a large number of other functional variables listed in the first embodiment. In contrast to the teaching of the known art of US2012269420, examples of the present invention propose to identify and extract at least one MC variable from a processed MC image of microvessels and at least one of: a quantification of a morphological parameter of the MC (e.g., morphometric analysis (e.g., tortoisity, fractals, bifurcations, etc.)) or at least one functional parameter of the MC.

Definition of Some Medical Terms Used Herein

Sepsis (definition taken from the recent consensus on the definition of sepsis) Singer et al The Third International Consensus Definitions for Sepsis and Septic Shock (Sepsis-3) JAMA. 2016; 315(8):801-810

Sepsis is a syndrome shaped by pathogen factors and host factors (e.g., sex, race and other genetic determinants, age, comorbidities, environment) with characteristics that evolve over time. What differentiates sepsis from infection is an aberrant or dysregulated host response and the presence of organ dysfunction. Sepsis-induced organ dysfunction may be occult; therefore, its presence should be considered in any patient presenting with infection. Conversely, unrecognized infection may be the cause of new-onset organ dysfunction. Any unexplained organ dysfunction should thus raise the possibility of underlying infection. The clinical and biological phenotype of sepsis can be modified by preexisting acute illness, long-standing comorbidities, medication, and interventions. Specific infections may result in local organ dysfunction without generating a dysregulated systemic host response.

Thrombosis is the occurrence of a blood clot in a blood vessel, causing obstruction of blood flow through the circulation resulting in a depletion of oxygen supply to the tissues and consequently causing organ injury.

Infectious diseases are the condition where a subject gets infected by microorganisms including bacterial, fungal, viral, protozoan, parasitic, and prion. Such infections can enter tissue cells and cause a host immune response both if left untreated can lead to organ injury and ultimately death.

Shock is the condition where there is an insufficiency of the cardiovascular system to support the circulation with sufficient amount of oxygen carrying red blood cells to meet the metabolic demand of the tissue cells. Thus in shock the tissue cells require more oxygen to survive and carry out their functional activity than is being supplied by the microcirculation. Five types of shock are described based on the underlying cause: low volume, cardiogenic, obstructive, anaemic and distributive shock.

Low volume or hypovolemic shock caused by such conditions as bleeding results in a too low volume in the circulation restricting the flow of oxygen carrying red blood cells in the microcirculation. It can be treated by administrating blood or fluids and fixing the underlying cause. Cardiogenic shock can be caused by a heart attack (myocardial infarction) or a contusion of the heart. Obstructive shock is caused by a restriction of the blood flow due to external pressure or obstruction of the circulation such as occurs in cardiac tamponade or a tension pneumothorax. Anaemic shock is the condition where the supply of oxygen by red blood cells becomes depleted due to an insufficient amount of red blood cell availability due to anaemia such as can occur in haematological conditions and cancer as well as during hospitalization where too much intravenous fluids are administered diluting the density of the RBC and thereby of haemoglobin in the circulation. Distributive shock is a defect in the distribution of the circulation resulting in areas between and within organs becoming depleted of oxygen carrying blood. It is a vascular regulatory defect caused by conditions as sepsis, anaphylaxis and overdoses of drugs.

Tissue RBC perfusion (tRBCp) is defined as the amount of RBC being perfused in a field of view of an IVM image sequence. It is derived by multiplying the whole blood volume with capillary haematocrit (e.g. cHct which is the ratio of volume of a blood vessel segment to the volume occupied by the RBCs residing in it) of in all detected capillary segments in an IVM image sequence for the calculation of tp, where s is the spatial displacement of blood within dt, V the volume of the vessel segment, n the number of visualized vessel segments, and FOV the field of view and d the depth of the tissue volume visualized by the IVM image sequence. From this value it is possible to evaluate the perfusion of the tissue by RBCs, the tRBCp, where s is the spatial displacement of blood within dt, V the volume of the vessel segment, cHct the capillary hematocrit, n the number of visualized vessel segments, and FOV the field of view and d the depth of the tissue volume visualized by the IVM image sequence, tRBCp, can be calculated by using an algorithm-based analysis of standard IVM image sequences (MicroTools (7) or via AI methodology and represents the combination of all determinants of microcirculatory diffusion and convection capacity measured by IVM an thus provides a better measure of tissue perfusion than tp alone.

Hemodynamic coherence ([10]) is the condition where following shock therapeutic correction of systemic hemodynamic variables of the circulation such as blood pressure cardiac output result in a parallel improvement in the circulation and delivery of blood of the individual organs and their microcirculation. Loss of hemodynamic coherence is when there is a disassociation between the systemic and microcirculation and despite correction of the systemic circulation the microcirculation remains altered and dysfunctional. This is the condition where monitoring the microcirculation is required because further therapeutic interventions aimed at the systemic circulation will be futile and specific microcirculatory guided therapy is required, which can be achieved by IVM monitoring such as described herein. Conditions where such a loss of hemodynamic occurs include microcirculatory heterogeneity such as occurs in sepsis, dilution of the microcirculatory red blood cell availability such as occurs during hemodilution and anaemic shock, microcirculatory tamponade such as occurs where there is too much arterial vasoconstriction induced by excessive administration of vasopressor agents and tissue oedema such as can occur in condition of inflammation, infectious disease and burns.

Wounds can occur due to a multiple causes. Wounds occur when the natural structure of tissue cells such as skin or internal organ tissue are disrupted due to injury, surgery, disease such as diabetes, burns, infection or trauma instigating a sequel of events whereby the body recruits inflammatory and cellular mediators to heal the wound and return it to its natural state. The healing process goes through different phases including haemostasis or blood clotting, inflammation, tissue growth to fix the wound and finally a maturation process where tissue remodelling occurs.

Diabetes is a metabolic disorder characterized by high blood sugar levels which persist over longer periods of time. Acute complications of diabetes can include a glycemic shock and death. Diabetes can result in cardiovascular and renal disease, foot ulcer wounds and neurological and eye disorders.

Oncology is the area of medicine related to cancer where there is an uncontrolled multiplication of cells. These abnormally growing cells can spread to other parts of the body. Treatment can involve surgery and/or chemo/radio and photodynamic therapy. Some examples of the invention described herein propose for the IVM device to help diagnose (during surgery or endoscopically such as the oral, cervix and skin), clinical decision making (definition of area of resection) as well as a recognition of malignancy due to abnormal morphology and/or blood flow kinetics. Organs that can be affected by cancer include almost all organs including skin, lung, cervix, ovaries, liver, kidney, pancreas, stomach, intestines, brain, ovaries, colon and rectum, head and neck, oral, testes, prostate, lung and bone.

Hypertension occurs when arterial blood pressure is sustained at a high level. It causes remodeling of the microcirculation is considered a risk factor leading to clinical complications. Long-term high blood pressure is a major risk factor for coronary artery disease, stroke, heart failure, atrial fibrillation, peripheral arterial disease, and chronic kidney disease, and dementia.

In the foregoing specification, an invention has been described with reference to specific illustrated examples. It will, however, be evident that various modifications and changes may be made therein without departing from the scope of the invention as set forth in the appended claims.

The connections as discussed herein may be any type of connections suitable to transfer signals from or to the respective nodes, units or devices, for example via intermediary components. Accordingly, unless implied or stated otherwise, the connections may for example be direct connections or indirect connections. The connections may be illustrated or described in reference to being a single connection, a plurality of connections, unidirectional connections or bidirectional connections. However, different illustrated examples may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Any arrangement of components to achieve the same functionality is effectively 'associated such that the desired functionality is achieved. Hence, any two components herein combined to achieve a particular functionality can be 'associated with' each other such that the desired functionality is achieved, irrespective of architectures or intermediary components. Likewise, two components so associated can also be viewed as being 'operably connected', or 'operably coupled' to each other to achieve the desired functionality.

Furthermore, those skilled in the art will recognise that boundaries between the above described operations are merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Furthermore, the illustrated examples may be implemented as circuitry located in a single integrated circuit or within the same device. Alternatively, the illustrated examples may be implemented as any number of separate integrated circuits or separate devices interconnected with each other in a suitable manner. However, other modifications, variations and alternatives are also possible. The specifications and drawings are, accordingly, to be regarded in an illustrative rather than in a restrictive sense.

It will be appreciated that, for clarity purposes, the above description has described embodiments of the invention with reference to different functional units and processors. However, it will be apparent that any suitable distribution of functionality between different functional units or processors, for example with respect to the equalizers, detectors, cyclic redundancy check circuits or components, etc., may be used without detracting from the invention. Hence, references to specific functional units are only to be seen as references to suitable means for providing the described functionality, rather than indicative of a strict logical or physical structure or organization.

Although the present invention has been described in connection with some embodiments, it is not intended to be limited to the specific form set forth herein. Rather, the scope of the present invention is limited only by the accompanying claims. Additionally, although a feature may appear to be described in connection with particular embodiments, one skilled in the art would recognize that various features of the described embodiments may be combined in accordance with the invention. In the claims, the term 'comprising' does not exclude the presence of other elements or steps.

Furthermore, although individually listed, a plurality of means, elements or method steps may be implemented by, for example, a single unit or processor. Additionally, although individual features may be included in different claims, these may possibly be advantageously combined, and the inclusion in different claims does not imply that a combination of features is not feasible and/or advantageous. Also, the inclusion of a feature in one category of claims does not imply a limitation to this category, but rather indicates that the feature is equally applicable to other claim categories, as appropriate.

Furthermore, the order of features in the claims does not imply any specific order in which the features must be performed and in particular the order of individual steps in a method claim does not imply that the steps must be performed in this order. Rather, the steps may be performed in any suitable order. In addition, singular references do not exclude a plurality. Thus, references to 'a', 'an', 'first', 'second', etc. do not preclude a plurality.

Thus, the inventors have provided an IVM device and associated medical diagnosis method that provides more relevant and more detailed information extracted from an MC in order to gain a deeper understanding of health, disease and therapy of these segmented microvascular structures. Furthermore, the IVM device and associated medical diagnosis method provides a significantly improved speed of accessing, and accurate processing of, MC image data, effectively real-time, in order to better advise clinicians of a health, disease and/or therapy of a patient, thereby substantially alleviating the aforementioned disadvantages with prior art arrangements.

LIST OF ABBREVIATIONS

AI artificial intelligence
ML machine learning
OPS orthogonal polarized spectroscopy
SDF side stream dark field imaging
IDF incident dark field imaging
IVM intelligent vital microscopy
RELU rectifier linear units
ECOS extracorporeal organ support
Ht hematocrit
HVM handheld vital microscopy
NTG nitro-glycerine
RPMP relevant physiological microcirculatory parameters (RPMP))
DALY Disability-Adjusted Life Year
APACHE scAcute Physiology, Age, Chronic Health Evaluation
SOFA Sequential Organ Failure Assessment
BP diastolic blood pressure
TPR total peripheral resistance
Hb haemoglobin
TVD capillary total vessel density
FCD functional capillary density
PPV proportion of perfused vessels
RBCv red blood cell velocity
PVD Proportion of perfused vessel density
RBC red blood cells
VD vessel diameters

REFERENCES

[1]. Klyscz T, Jünger M, Jung F, Zeintl H (1997) Cap Image—ein neuartiges computerunterstütztes Videobildanalysesystem für die dynamische Kapillarmikroskopie. Biomedizinische Technik, Band 42 Heft 6:168-175.

[2], Bezemer R, Dobbe J G, Bartels S A, Boerma E C, Christiaan Boerma E, Elbers P W G, Heger M, Ince C. Rapid automatic assessment of microvascular density in side stream dark field images. Med. Biol. Eng. Comput. 2011; 49: 1269-1278.

[3]. Bunyak F, Palaniappan K, Glinskii O, Glinskii V, Glinsky V, Huxley V. Epifluorescence-based quantitative microvasculature remodeling using geodesic level-sets and shape-based evolution, Conf Proc IEEE Eng Med Biol Soc. 2008; 2008:3134-7.

[4]. Demir S U, Hakimzadeh R, Hargraves R H, Ward K R, Myer E V, Najarian K. An automated method for analysis of microcirculation videos for accurate assessment of tissue perfusion. BMC Med. Imaging 2012; 12: 37,

[5]. Groner W, Winkelman J W, Harris A G, Ince C, Bouma G J, Messmer K, Nadeau R Orthogonal polarization spectral imaging: A new method for study of the microcirculation. Nature Medicine 1999 5(10):1209-12.

[6]. Goedhart P T, Khalilzada M, Bezemer R, Merza J, Ince C Sidestream dark field (SDF) imaging: a novel stroboscopic LED ring-based imaging modality for clinical assessment of the microcirculation. Opt Express 2007 15(23):15101-15114.

[7]. Hilty M P, Arend S, Van Assen M, Toraman F, Ince C. A software tool to quantify capillary blood volume and absolute red blood cell velocity in sublingual incident dark field microscopy video clips. Intensive Care Med Exp 2018; 6: 172-173.

[8]. Van Elteren, H. A., Ince, C., Tibboel, D., Reiss, I. K. M., & de Jonge, R. C. J. (2015). Cutaneous microcirculation in preterm neonates: comparison between sidestream dark field (SDF) and incident dark field (IDF) imaging. Journal of Clinical Monitoring and Computing, 29(5), 543-548. doi:10.1007/s10877-015-9708-5

[9]. Uz Z, van Gulik T M, Aydemirli M, Guerci P, Ince Y, Cuppen D V, Ergin B, Aksu U, de Mol B A, Ince C Identification and quantification of human microcirculatory leukocytes using handheld video microscopes at the bedside. J Appl Physiol, 2018 Mar. 8. doi: 10.1152, japplphysiol.00962.2017.

[10]. Ince C. Hemodynamic coherence and the rationale for monitoring the microcirculation. Crit Care. 2015; 19 Suppl 3:S8

[11]. Ince C, Boerma E C, Cecconi M, De Backer D, Shapiro N I, Duranteau J, Pinsky M R, Artigas A, Teboul J L, Reiss I K M, Aldecoa C, Hutchings S D, Donati A, Maggiorini M, Taccone F S, Hernandez G, Payen D, Tibboel D, Martin D S, Zarbock A, Monnet X, Dubin A, Bakker J, Vincent J L, Scheeren T W L Second consensus on the assessment of sublingual microcirculation in critically ill patients: Results from a task force of the European Society of Intensive CareMedicine. Intensive Care Med. 2018 018 March; 44(3):281-299.15.

[12] Liu C, Gomez H, Narasimhan 5, et al Real-time visual analysis of microvascular blood flow for critical care. In: 2015 IEEE Conference on Computer Vision and Pattern Recognition (CVPR). IEEE, Boston, Mass., USA, pp 2015 2217-2225.

[13]. Dobbe J G, Streekstra G J, Atasever B, van Zijderveld R, Ince C. Measurementof functional microcirculatory geometry and velocity distributions using automated image analysis. Med Biol Eng Comput 2008 46(7):659-70.

[14]. R Development Core Team (2011) R: A language and environment for statistical computing. R Foundation for Statistical Computing, Vienna, Austria

[15]. Chollet F, Allaire J J (2018) Deep Learning with R, 1 edition. Manning Publications, Shelter Island, N.Y.

[16]. Sachs M C (2017) plotROC: A Tool for Plotting ROC Curves. J Stat Softw 79: https://doi.org/10.18637/jss.v079.c02.

[17]. Wickham H (2010) ggplot2: Elegant Graphics for Data Analysis, 1st ed. 2009. Corr. 3rd printing 2010 edition. Springer, New York.

[18]. Kellum J A, Lameire N; KDIGO AKI Guideline Work Group. Diagnosis, evaluation, and management of acute kidney injury: a KDIGO summary (Part 1). Crit Care. 2013 Feb. 4; 17(1):204.

We claim:

1. An intelligent vital microscopy, IVM, device comprising:
a magnifying lens operably coupled to a focus mechanism and an illumination source for illuminating an organ surface;
a receiver operably coupled to the magnifying lens focus mechanism and illumination source and configured to receive at least one IVM image of a human microcirculation, MC, of the organ surface;
a learning processor coupled to the receiver and configured to:
process the at least one IVM image, identify single cellular oxygen transporting constituents of the MC embedded within flowing red blood cells, RBCs, of the at least one IVM image and extract at least one MC variable that describes oxygen transportation by RBCs in the MC, and identify from the extracted at least one MC variable that describes oxygen transportation by RBCs of the processed at least one IVM image, based on MC analysis of training data images previously input to the learning processor for analyzing oxygen transportation by RBCs in the MC, a disease diagnosis and identify an amount of therapy arranged to provide a therapeutic effect to the human of the at least one IVM image in response to the identified disease diagnosis; and perform at least one of:

identify hypovolemia, hypotension, overhydration and dehydration and a need for a therapeutic treatment that improves the transportation of oxygen in the human by at least one of: fill intravascular volume of the MC; provide hydration, provide blood transfusion, increase of cardiac output; increase perfusion pressure; start diuretic therapy or haemodialysis, halt haemodialysis, administration of vasopressure or vasodilatory agents;

identify when a treatment dose threshold is reached in tumour therapy in advance of an occurrence of complications;

identify when haemodialysis or continuous renal replacement therapy is recommended and output a clinical decision regarding duration and a need for supplemental therapy;

identify a need for blood purification;

identify during a blood purification process, a time for cessation of the blood purification process or a need to adjust at least one parameter of the blood purification process;

output an identification of whether an intended therapeutic intervention will provide a positive result;

provide feedback as to an efficacy of an intended therapeutic intervention once applied and identify an alternative dose adjustment if the efficacy is not as desired;

identify a diagnosis of at least one of: radiotherapy photodynamic chemotherapy surgery, and an output coupled to the learning processor and configured to output a clinical decision regarding a need for adjuvant therapy.

2. The IVM device of claim 1, wherein the extracted at least one MC variable that describes oxygen transportation by RBCs in the MC comprises at least one functional parameter of the oxygen transportation RBC of the MC that comprises one of: functional capillary density, FCD, tissue red blood cell perfusion, tRBCp; total vessel density, TVD; MC hemodynamic values; capillary; a venule; arteriolar blood flow and velocity; blood volume; an identification of at least one type of vessel; a proportion of perfused vessel density, PVD; a proportion of FCD of flowing red blood cells, RBC, that carry oxygen; a vessel diameter, VD; a proportion of perfused vessels, PPV, a microvascular flow index of a flow heterogeneity, MFIhet; rolling and sticking leukocytes, microscopic or fluorescence spectroscopy, identification of a number of platelets; microcirculatory RBC Hb saturation; a capillary tube and discharge haematocrit.

3. The IVM device of claim 2, wherein the at least one functional parameter is one of:

measured in steady state or as a result of a challenge, where the challenge is one of: metabolic, vasodilator, blood transfusion, exercise, focus quality, depth of focus, image movement and content of microcirculatory structures;

is output as feedback to a user as one or more of:
  a quality of at least one IVM image sequence of a human organ surface or sublingual microcirculation,
  a classification of identified MC abnormality,
  an origin of a cause of the identified MC abnormality,
  a recommended therapeutic strategy to normalize MC abnormalities and resolve a disease state.

4. The IVM device of claim 1, wherein the identified extracted at least one MC variable that describes oxygen transportation by RBCs in the MC comprises at least one of: a quantification of a morphological parameter of the MC, at least one functional parameter of the MC, and the identified at least one morphological parameter comprises at least one of: functional microcirculatory structure, a total vessel density, TVD; a tortuosity; one or more fractal dimension; bifurcations of MC vessels.

5. The IVM device of claim 1, wherein the identified extracted at least one MC variable that describes oxygen transportation by RBCs in the MC comprises a functional microcirculatory structure comprising at least one of: sputum glands, orifices, vessel loops, rectal crypts, cell to cell junctions, one or more cell dimensions, mitochondria, properties of nuclei, microcirculatory units related to organ function, intestinal villi, renal tubular structures, liver lobule, alveoli, glycocalyx dimensions.

6. The IVM device of claim 1, wherein the identified extracted at least one MC variable that describes oxygen transportation by RBCs in the MC comprises at least one of: a portion or an entirety of properties and structure of a trained neuronal network, incorporated in the IVM device and trained for outputting one or more of: (i) a quality of the at least one IVM image of a human organ surface or sublingual microcirculation, (ii) a classification of identified MC abnormality, (iii) an origin of a cause of the identified MC abnormality, (iv) a recommended therapeutic strategy to normalize the identified MC abnormality and resolve a disease state.

7. The IVM device of claim 1, wherein the learning processor is configured to process the at least one IVM image and identify at least one of:

at least one of: a type of disease, inflammation, wound surface or type of pathology;

at least one of: a type of disease, inflammation or type of pathology and an amount of therapy arranged to provide a therapeutic effect to the human of the IVM image in response to the identified type of disease, inflammation or type of pathology;

a change over time, in at least one of: an identified disease type, an amount of therapy arranged to provide a therapeutic effect to the human of the IVM image sequence;

a type of shock a patient is suffering from and identify at least one of: a resuscitation strategy based on a type of fluid, vasopressor agent or blood, a futility of resuscitation, an area of the MC that requires resuscitating; a target for titration of intravenous fluids, vasopressor agent and blood; and an early detection of at least one of: cancer, osteo-radio necrosis decubitus, peripheral vascular disease.

8. The IVM device of claim 1, wherein the learning processor is configured to process the at least one IVM image and identify a type of pathology that comprises detecting a presence of at least one of: an abnormal number or abnormal flow of blood cells; anaemia; abnormal tumour cells; abnormal sickle cells; parasites, viruses, bacteria or detecting a presence of abnormal sickle cells and evaluate and output an efficacy of administered therapy to treat the pathology.

9. The IVM device of claim 1, wherein the identified disease is one of:
- a presence of sepsis and the learning processor is configured to distinguish between inflammation and infection from early sepsis or septic shock based on a nature of a microcirculatory alteration;
- a presence of at least one organ at risk of failure based on MC alteration;
- diabetes and an identified development of hyperglycaemia and heart failure and an identified medication or treatment to reduce a risk of heart failure;
- a presence or risk of a cardiovascular accident and/or stroke;
- a presence of cardiovascular compromised as a result of trauma;
- a presence or progress and severity of kidney disease;
- presence of cardiovascular compromised in patients on extracorporeal organ support;
- a risk of and/or having a tropical disease;
- a risk of associated complications from hypertension or diabetes;
- a presence of retinal or conjunctival disease;
- a risk of a coma, or delirium;
- a presence or risk of subarachnoid haemorrhage;
- a presence or risk of cervical cancer following analysis and detection of an abnormal MC of the cervix surface;
- identify a risk or presence of inflammatory bowel disease following an analysis of endoscopic rectal sigmoid MC crypts;
- identify a risk or presence in the human of at least one of: cardiac tamponade, thrombosis, arrhythmias; pulmonary hypertension, myocardial infarction;
- identify a state of inflammation, infection to indicate leukaemia of the human;
- a development of dementia and Alzheimer;
- identify impending complications during surgery and provide advice preceding the occurrence of a complication;
- identify a presence of brain disease by examination of conjunctive or retinal microcirculation;
- identify a presence and/or origin of tropical disease;
- identify a presence and action of a pathogen.

10. The IVM device of claim 1, wherein the learning processor comprises a trained two-dimensional convolutional neuronal network, trained using at least IVM image sequences of healthy or diseased humans, recorded either before or after local vasodilation, which creates a prediction model, wherein the prediction model is arranged to identify a need for a resuscitation procedure.

11. The IVM device of claim 1, wherein the learning processor is further configured to identify a medical state of the human and comprises the learning processor being configured to:
- analyse the MC to use as a resuscitation target in at least one of the following applications: traumatic haemorrhage, myocardial infarction, stroke; and
- identify a clinical strategy, in response to the analysis, related to a use of one or more of: blood transfusion vasoactive compounds, extracorporeal organ support, ECOS, including renal cardiac, liver and lung ventilation support, an internal organ support or replacement device, a fluid to be applied to the human;
- analyse the MC of the pelvic area, cervix and vaginal wall of the human and determine and output a need for at least one of: prolapse surgery, hormone therapy; chemotherapy; laser therapy;
- analyse the MC of the cervix and vaginal wall of the human and determine and output a diagnosis for wound healing following urogynaecology surgery or attachment of materials to an uterus wall;
- analyse the MC of a depth of focus of a vaginal wall of the human, diagnose vaginal atrophy to titrate hormone therapy measure increase in vaginal and determine and output an optimal length of treatment and dosage;
- analyse a paediatric MC or a neonatal MC and identify a treatment and severity of a disease;
- analyse a MC in an ICU and detect an abnormality that represents an early warning of an impending cardiovascular event or infection;
- analyse a MC in an ambulance service and evaluate a cardiovascular status of the human;
- analyse a MC and diagnose anaemia and output at least one of: a need for blood transfusion, an efficacy of blood transfusion, a quality of transfused blood to improve red blood cell and oxygen delivery to the MC;
- analyse a MC and detect changes in a red blood perfused boundary region measured as a marker of glycocalyx barrier function and identify a therapeutic strategy that restores the glycocalyx.

12. The IVM device of claim 1, configured to be used in surgery, wherein the learning processor is configured to perform at least one of:
- analyse an MC of an organ to be transplanted and a recipient organ during an organ transplantation and determine therefrom additional medical support that is needed during surgery;
- measure MC on organ surfaces during surgery and provide clinical decision making data that would affect an identified outcome of the surgery;
- determine a presence of micro metasis during surgery due to abnormalities in vessel structures for intraoperative treatment;
- evaluate at least one of: a risk of anastomotic leakage, an identification of a resection boundary, a presence of one or more unidentified metastatic tumour;
- analyse an MC of at least one patient and output an indication for implantation of an organ support device to be planted internally;
- analyse an MC of at least one patient and evaluate how long an organ has been ischemic in a non-heart beating donor and an identification of a usability of organs harvested from non-heart beating donors
- analyse an MC of at least one patient and output an identification following attaching at least one of: a cardiac assist device, a renal assist device, a recommendation to adjust a cardiac assist device or cardiopulmonary bypass device parameter, a recommendation to adjust a renal assist device parameter, an adjuvant therapy to be used when applying a cardiac assist device or renal assist device;
- analyse an MC of at least one patient surgery and determine therefrom a sublingual or organ surface to be used as an anaesthesia tool and evaluate and output a depth of anaesthesia, impending hypertension and an indication of a need for hemodynamic support;
- analyse an MC of tumour surfaces of the patient for intraoperative decision making for resection of tumours;

analyse during surgery an MC of at least one of a patient's: lungs, brain, liver, kidney; and output a pathology evaluation.

13. The IVM device of claim 1, wherein the learning processor is configured to analyse an MC of at least one patient prior to surgery and perform at least one of:
and output an identification for implantation of an organ support device to be planted internally;
analyse an MC of at least one patient and evaluate how long an organ has been ischemic in a non-heart beating donor and an identification of a usability of organs harvested from non-heart beating donors;
analyse an MC of at least one patient and output an identification following attaching at least one of: a cardiac assist device, a renal assist device, a recommendation to adjust a cardiac assist device parameter or cardiopulmonary bypass device parameter, a recommendation to adjust a renal assist device or haemodialysis parameter, an adjuvant therapy to be used when applying a cardiac assist device or renal assist device;
analyse an MC of at least one patient and determine therefrom a sublingual or organ surface to be used as an anaesthesia tool and evaluate and output a depth of anaesthesia and an indication of a need for hemodynamic support.

14. The IVM device of claim 1, wherein the learning processor is configured to process the at least one IVM image sequence, identify a wound surface and analyse a nature of the wound that comprises at least one of: a burn, decubitus, surgical, trauma, venous ulcers, radiotherapy, dermatological disorders, melanoma; wherein the learning processor is configured to:
evaluate a severity of a patient's wounds based on the analysis and, in response thereto:
identify a wound healing of scar formation; and
output a recommended fluid resuscitation strategy that reduces edema formation, medication to promote wound healing and reduces scar formation or cure dermatological disorders.

15. The IVM device of claim 1, wherein the learning processor configured to identify from the extracted at least one MC variable that describes oxygen transportation by RBCs in the MC of the at least one IVM image an intervention, the learning processor being configured to analyse the extracted at least one MC variable of the at least one IVM image during use of one of:
a dialysis device and react to a change occurring during dialysis treatment and output a clinical decision based thereon;
a haemodialysis device and react to a detected change in an analysed progress of haemodialysis and adjust at least one parameter in the haemodialysis device in response thereto.

16. The IVM device of claim 1, wherein the learning processor is configured to process the at least one IVM image and identify a type of shock that the human is suffering from, wherein the type of shock comprises one of:
determining a presence of loss of hemodynamic coherence and outputting a type and dose of therapeutic drugs for resuscitation comprising one or more of: fluids, blood products, vasopressor agents, vasodilators, antibiotics, or anti-inflammatories based on a differential diagnosis of the type of detected shock;
determining a presence of a lack of tissue perfusion and outputting a resuscitation strategy in response to a determined septic or shock condition of the human.

17. The IVM device of claim 1, wherein the learning processor being configured to identify from the extracted at least one MC variable of the at least one IVM image a disease diagnosis or an intervention during cardiac surgery comprises at least one of: identify a need for an ablation; identify a placing of at least one stent; output a recommendation for carrying out an intervention output a recommendation for a surgical placement of cardiac surgical materials or treatment, output a recommendation for a bridge to treat a procedure or support device; identify an anaesthesiological procedure; identify a parameters related to a cardiopulmonary bypass, CPB, pump to be used during cardiac surgery.

18. The IVM device of claim 1, further comprising a memory operably coupled to the learning processor and arranged to store at least one of: patient data of a state of vascular or micro-vascular health output from the analysis; determined impending disease based on risk; recommendation for pre-operative boosting of cardiovascular health that reduces post-operative or therapeutic complications.

19. The IVM device of claim 1, further comprising an AI based communication circuit configured to communicate with a remote AI controlled cloud base dataset, wherein the AI based communication circuit is configured to perform at least one of:
a search on the remote AI controlled cloud base dataset;
a request of at least one further input MC variable to supplement the at least one MC variable of the at least one IVM image and perform an in depth diagnosis of a condition of the patient
compare an identified at least one of: an intervention, a disease state, a disease diagnosis, with data stored in the remote AI controlled cloud base dataset to determine a cause of an identified disease and advice for a therapeutic option.

20. A medical method comprising:
illuminating an organ surface using a magnifying lens operably coupled to a focus mechanism and an illumination source;
a receiver operably coupled to the magnifying lens focus mechanism and illumination source and
receiving at least one intelligent vital microscopy, IVM, image of a human microcirculation, MC, of the organ surface;
processing the at least one IVM image of a human MC by a learning processor;
identifying single cellular oxygen transporting constituents of the MC embedded within flowing red blood cells, RBCs, of the at least one IVM image;
extracting at least one MC variable that describes oxygen transportation by RBCs in the MC from the processed at least one IVM image;
identifying from the extracted at least one MC variable that describes oxygen transportation by RBCs of the processed at least one IVM image, based on MC analysis of training data images previously input to the learning processor for analyzing oxygen transportation by RBCs in the MC, at least one of: a disease diagnosis and identify an amount of therapy arranged to provide a therapeutic effect to the human of the at least one IVM image in response to the identified disease diagnosis; and
performing at least one of:
identifying hypovolemia, hypotension, overhydration and dehydration and a need for a therapeutic treatment that improves the transportation of oxygen in the human by at least one of: fill intravascular volume of the MC; provide hydration, provide blood transfusion, increase of cardiac output; increase perfusion pressure; start diuretic therapy or haemodialysis, halt haemodialysis, administration of vasopressure or vasodilatory agents;

identifying when a treatment dose threshold is reached in tumour therapy in advance of an occurrence of complications;

identifying when haemodialysis or continuous renal replacement therapy is recommended and output a clinical decision regarding duration and a need for supplemental therapy;

identifying a need for blood purification;

identifying during a blood purification process, a time for cessation of the blood purification process or a need to adjust at least one parameter of the blood purification process outputting an identification of whether an intended therapeutic intervention will provide a positive result;

providing feedback as to an efficacy of an intended therapeutic intervention once applied and identify an alternative dose adjustment if the efficacy is not as desired;

identifying a diagnosis of at least one of: radiotherapy photodynamic chemotherapy surgery; and outputting a clinical decision regarding a need for adjuvant therapy.

21. The IVM device of claim 1, wherein the extracted at least one MC variable that describes oxygen transportation by RBCs in the MC of the processed at least one IVM image comprises a quantification of a morphological parameter of at least one oxygen transportation RBC in the MC.

* * * * *